United States Patent [19]

Reed, III, deceased

[11] Patent Number: 4,675,186

[45] Date of Patent: Jun. 23, 1987

[54] 6-(1-ACYL-1-HYDROXYMETHYL)PENICIL-LANIC ACID DERIVATIVES

[75] Inventor: Lawrence A. Reed, III, deceased, late of Pawcatuck, Conn., by Anne Reed, administrator

[73] Assignee: Pfizer Inc., New York, N.Y.

[21] Appl. No.: 839,834

[22] Filed: Mar. 11, 1986

Related U.S. Application Data

[63] Continuation-in-part of Ser. No. 724,857, Apr. 18, 1985, abandoned.

[51] Int. Cl.$^4$ .................. C07D 499/00; A61K 31/415
[52] U.S. Cl. .................... 424/114; 540/304; 540/306; 514/195; 514/192
[58] Field of Search ...................... 540/195, 304, 306; 424/114; 514/195

[56] References Cited

U.S. PATENT DOCUMENTS

| | | | |
|---|---|---|---|
| 4,207,323 | 8/1980 | Beattie et al. | 424/270 |
| 4,282,149 | 8/1981 | Sheehan et al. | 260/245.2 R |
| 4,287,181 | 9/1981 | Kellogg | 424/114 |
| 4,342,768 | 8/1982 | Kellogg | 424/250 |
| 4,590,073 | 5/1986 | Barth | 424/114 |

FOREIGN PATENT DOCUMENTS 2053220 7/1980 United Kingdom .

Primary Examiner—Nicholas S. Rizzo
Attorney, Agent, or Firm—Charles J. Knuth; Albert E. Frost; Robert K. Blackwood

[57] ABSTRACT 6-(1-Acyl-1-hydroxymethyl)penicillanic acid derivatives are useful as antibacterials and/or beta-lactamase inhibitors.

56 Claims, No Drawings

6-(1-ACYL-1-HYDROXYMETHYL)PENICILLANIC ACID DERIVATIVES

CROSS REFERENCE TO RELATED APPLICATION

This application is a continuation-in-part of copending U.S. application Ser. No. 724,857, filed Apr. 18, 1985, now abandoned.

BACKGROUND OF THE INVENTION 6-(1-Acyl-1-hydroxymethyl)penicillanic acid derivatives, having the partial structure

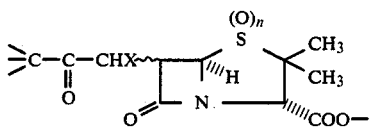

wherein n is 0, 1 or 2, and X is hydroxy or an acyloxy group, are generally useful as antibacterials and/or beta-lactamase inhibitor. Some of these compounds possess excellent antibacterial activity per se, and so are valuable as industrial or medicinal antibacterial agents in their own right. Additionally, and more generally, they have particular value as beta-lactamase inhibitors; as such, they are useful in combination with conventional beta-lactam antibiotics (penicillins and cephalosporins) against microorganisms resistant or partially resistant to beta-lactam antibiotics through production of beta-lactamase enzymes.

beta-Lactamase inhibiting 6-(1-hydroxyalkyl)penicillanic acid 1,1-dioxides (sulfones) and 3carboxylate esters thereof have been reported by Kellogg (U.S. Pat. Nos. 4,287,181; 4,342,768; European Patent Publication No. 83977), while 6-(aminoacyloxymethyl)penicillanic acid 1,1-dioxides have been reported by Barth (U.S. Pat. No. 4,503,040). Antibacterial 6-(1-hydroxyalkyl)penicillanic acids and their 1-oxides (sulfoxides) have been very broadly reported by Beattie et al., (U.S. Pat. No. 4,207,323). While the claimed genus of Beattie et al. might possibly be construed to include some of the present compounds in a non-specific manner, this reference does not even generally (let alone specifically) disclose any compounds containing the 6-(1-acyl-1-hydroxyalkyl)substituent which represents an essential feature of the present invention.

U.K. Patent Application No. 2,053,220 broadly discloses beta-lactamase inhibiting compounds of the formula

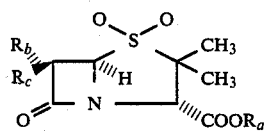

The definitions of $R_a$, $R_b$ and $R_c$ define literally an infinite number of compounds. Said infinity of compounds proposed might be construed to encompass some of the 1,1-dioxide compounds of the present invention. However, there is no specific mention of or preparative method provided for any compounds of the type of the present invention, let alone any hint or suggestion that the present compounds represent preferred compounds, having potent antibacterial and/or betalactamase inhibitory activity.

SUMMARY OF THE INVENTION

The present invention is concerned with antibacterials, beta-lactamase inhibitors and/or intermediates containing the following partial structure:

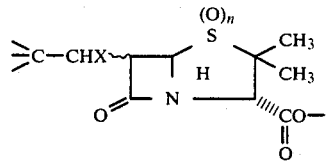

wherein n is 0, 1 or 2, and X is hydroxy or an acyloxy group. Because of their relative ease of preparation and excellent activity, the present invention is particularly concerned with antibacterial and/or beta-lactamase inhibitory compounds having the formula

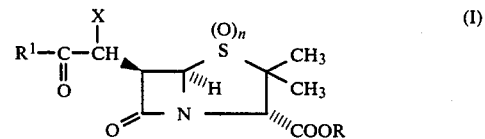

wherein
n is 0, 1 or 2;
X is OH or $OCOR^2$, wherein $R^2$ is hydrogen or $(C_1-C_4)$alkyl;
R is hydrogen, a radical group forming an ester hydrolyzable under physiological conditions, or an acyloxymethyl or 1-(acyloxy)ethyl radical derived from a conventional beta-lactam antibiotic; and
$R^1$ is $(C_1-C_7)$alkyl, $(C_5-C_7)$cycloalkyl, $(C_6-C_{12})$cycloalkylalkyl, $(C_6-C_{12})$alkylcycloalkyl, adamantyl, phenyl, $(C_7-C_{12})$phenylalkyl, $(C_7-C_{12})$alkylphenyl, $(C_7-C_{12})$phenoxyalkyl, naphthyl, furyl $(C_5-C_{10})$-furylalkyl, benzofuranyl, benzofuranylmethyl, thienyl, $(C_5-C_{10})$thienylalkyl, benzothienyl, benzothienylmethyl, $(C_5-C_8)$-N-alkylpyrrolyl, N-phenylpyrrolyl, $(C_{11}-C_{12})$-N-(phenylalkyl)pyrrolyl, $(C_6-C_{12})$-N-alkylpyrrolylalkyl, $(C_9-C_{12})$-N-alkylindolyl, $(C_9-C_{12})$-N-alkylindolylmethyl, $(C_9-C_{12})$-N-alkylisoindolyl, $(C_9-C_{12})$-N-alkylisoindolylmethyl, $(C_9-C_{12})$-N-alkylisoindolylmethyl, indolizinyl, indolizinylmethyl, oxazolyl, $(C_4-C_9)$oxazolylalkyl, benzoxazolyl, benzoxazolylmethyl, isoxazolyl, $(C_4-C_9)$isoxazolylalkyl, benzisoxazolyl, benzisoxazolylmethyl, thiazolyl, $(C_4-C_9)$-thiazolylalkyl, benzothiazolyl, benzothiazolylmethyl, isothiazolyl, $(C_4-C_9)$isothiazolylalkyl, benzothiazolyl, benzothiazolylmethyl, $(C_4-C_7)$-N-alkylpyrazolyl, $(C_5-C_{11})$-N-alkylpyrazolylalkyl, $(C_8-C_{11})$-N-alkylindazolyl, $(C_8-C_{11})$-N-alkylindazolylmethyl, $(C_4-C_7)$-N-alkylimidazolyl, $(C_5-C_{11})$-N-alkylimidazolylalkyl, $(C_8-C_{11})$-N-alkylbenzimidazolyl, $(C_8-C_{11})$-N-alkylbenzimidazolmethyl, pyridyl, $(C_6-C_{11})$-pyridylalkyl, quinolyl, quinolylmethyl, isoquinolyl, isoquinolylmethyl, pyrazinyl, $(C_5-C_{10})$pyrazinylalkyl, quinoxalinyl, quinoxalinylmethyl, pyrimidinyl, $(C_5-C_{10})$-pyrimidinylalkyl, quinazolinyl, quinazolinylmethyl, pyridazinyl, $(C_5-C_{10})$pyridazinylalkyl, phthalazinyl, phthalazinylmethyl, cinnolinyl or cinnolinylmethyl; or one of said groups mono- or disubstituted on aliphatic, aromatic or heterocyclic carbon with fluoro, chloro, bromo, $(C_1-C$-

4)alkyl, phenyl, hydroxy, (C$_1$–C$_4$)alkoxy, phenoxy, benzyloxy, (C$_2$–C$_5$)alkoxycarbonyloxy, (C$_2$–C$_4$)alkenyloxy, formyloxy, (C$_2$–C$_5$)-alkanoyloxy, (C$_2$–C$_5$)alkoxycarbonyl, (C$_1$–C$_4$)alkanesulfonamido, cyano, carbamoyl, (C$_2$–C$_5$)alkylcarbamoyl, di[(C$_1$–C$_4$)alkylcarbamoyl, aminosulfonyl, (C$_1$–C$_4$)alkylaminosulfonyl or di[(C$_1$–C$_4$)alkyl]aminosulfonyl, or

where

R$^{10}$ and R$^{11}$ are taken separately and

R$^{10}$ is hydrogen, (C$_1$–C$_4$)alkyl, phenyl or benzyl, and R$^{11}$ is hydrogen, (C$_1$–C$_4$)alkyl, phenyl, benzyl, formyl, (C$_2$–C$_5$)alkanoyl, benzoyl, phenoxyacetyl, phenylacetyl or phenylacetyl substituted on aromatic carbon with hydroxy or amino; or R$^{10}$ and R$^{11}$ are taken together with the nitrogen to which they are attached to form a pyrrolidine, piperidine, perhydroazepine, morpholine, piperazine, N-[(C$_1$–C$_4$)alkyl]piperazine or N-[(C$_2$–C$_5$)alkanoyl]-piperazine ring; where said disubstituents may be the same or different; with the provisos that no tetrahedral carbon is simultaneously bonded to a nitrogen or oxygen atom and a fluoro, chloro, bromo or second nitrogen or oxygen atom; and that no nitrogen is quaternary;

a pharmaceutically acceptable cationic salt when the compound contains a carboxylic acid group;

a pharmaceutically acceptable acid addition salt when the compound contains a basic nitrogen atom.

Preferred compounds have X as hydroxy and R$^1$ as alkyl, aminoalkyl, benzyloxyalkyl, cycloalkyl, adamantyl, phenyl, alkylphenyl, hydroxyalkylphenyl, chloroalkylphenyl, alkoxyphenyl, alkoxycarbonylphenyl, cyanophenyl, fluorophenyl, alkenyloxyphenyl, hydroxyphenyl, aminophenyl, dialkylaminophenyl, naphthyl, alkoxynaphthyl, furyl, thienyl, benzothienyl, benzyl, thenyl, furfuryl, phenylthiazolyl, N-alkylimidazolyl, quinolinyl, isoquinolinyl, N-(phenylalkyl)pyrrolyl, N-alkylpyrrolyl, or N-alkylindolyl. More preferred compounds have n as 0 and R$^1$ as methyl, t-butyl, 1-benzyloxy-1-methylethyl, 1-methylcyclohexyl, 1-adamantyl, 1-amino-1-methylethyl, phenyl, 4-methylphenyl, 4-(hydroxymethyl)phenyl, 4-(1-hydroxy-1methylethyl)phenyl, 4-(chloromethyl)phenyl, 4-methoxyphenyl, 2-methoxyphenyl, 4-propenyloxyphenyl, 4-methoxycarbonylphenyl, 4-cyanophenyl, 4-fluorophenyl, 3-hydroxyphenyl, 4-hydroxyphenyl, 4-aminophenyl 4-(dimethylamino)phenyl, 1-naphthyl, 2-ethoxy-1-naphthyl, 2-naphthyl, 2-furyl, 2-thienyl, 3-thienyl, 2-benzothienyl, benzyl, 2-thenyl, 3-methyl-2-imidazolyl, 2-phenyl-4-thiazolyl, N-methyl-2pyrrolyl, N-benzyl-2-pyrrolyl, N-methyl-2-indolyl, N-methyl-3-indolyl, 3-quinolinyl, or 1-isoquinolyl. The most preferred compounds further have the X-substituted carbon of the side chain in the S-configuration:

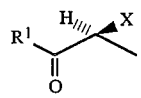

Pharmaceutically-acceptable acid addition salts include, but are not limited to, those with hydrochloric acid, sulfuric acid, nitric acid, phosphoric acid, citric acid, maleic acid, succinic acid, benzenesulfonic acid, p-toluenesulfonic acid, 2-naphthalenesulfonic acid and methanesulfonic acid. Pharmaceutically-acceptable cationic salts include, but are not limited to, those of sodium, potassium, calcium, N,N'-dibenzylethylenediamine, N-methylglucamine (meglumine) and diethanolamine. The preferred cationic salts are those of potassium and sodium.

The reference to esters which are hydrolyzable under physiological conditions refers to those esters frequently referred to as "pro-drugs". Such esters are now as well-known and common in the penicillin art as pharmaceutically-acceptable salts. Such esters are generally used to enhance oral absorption, but in any event are readily hydrolyzed in vivo to the parent acid. The more preferred ester forming radicals are those wherein R is: (5-methyl-1,3-dioxol-2-on-4-yl)methyl; 1H-isobenzofuran-3-on-1-yl; gamma-butyrolacton-4-yl; —CHR$^3$OCOR$^4$; or —CHR$^3$OCOOR$^5$; wherein R$^3$ is hydrogen or methyl; R$^4$ is (C$_1$–C$_6$)alkyl, (C$_1$–C$_6$) carboxyalkyl, carboxycyclohexyl or carboxyphenyl; and R$^5$ is (C$_1$–C$_6$)alkyl. The most preferred radicals are pivaloyloxymethyl and 1-(ethoxycarbonyloxy)ethyl.

The reference to an acyloxymethyl or 1-(acyloxy)ethyl derived from a conventional beta-lactam antibiotic refers to a mixed methanediol ester of the formula (I) wherein R is derived from one of the standard, well known beta-lactam antibiotics containing a carboxylic acid group on the carbon alpha to the beta-lactam ring:

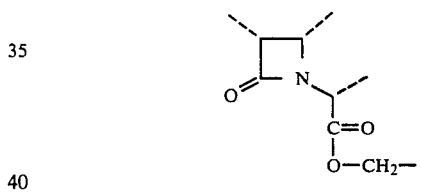

Preferred esters of this class are those wherein R is:

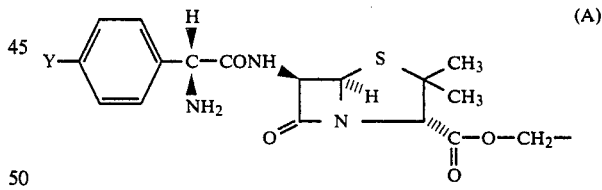

wherein Y is hydrogen, hydroxy, (C$_2$–C$_7$)alkanoyloxy, (C$_2$–C$_7$)alkoxycarbonyloxy, benzoyloxy monosubstituted with (C$_1$–C$_4$)alkyl, (C$_1$–C$_4$)alkoxy or halo. More preferred are those wherein Y is hydroxy or hydrogen, particularly the latter.

The present invention also encompasses a pharmceutical composition for treating bacterial infections which comprises in a weight ratio of 10:1 to 1:3 a conventional beta-lactam antibiotic and a compound of the formula (I) wherein R$^1$ is hydrogen or a radical group forming an ester which is hydrolyzable under physiological conditions. For this composition, preferred compounds of the formula (I) are defined above. Preferred beta-lactam antibiotics are penicillins or cephalosporins of established clinical utility, viz., amoxicillin, ampicillin, apalcillin, azlocillin, azthreonam, bacampicillin, carbenicillin, carbenicillin indanyl, carbenicillin phenyl, cefaclor, cefadroxil, cefaloram, cefamandole, cefamandole nafate, cefaparole, cefatrizine, cefazolin, cefbuperazone, cefmenoxime, cefonicid, cefodizime, cefoperazone, ceforanide, cefotaxime, cefotiam cefoxitin, cefpimazole, cefpiramide, cefpirome, cefsulodin, ceftazidime, ceftizoxime, ceftriaxone, cefuroxime, cephacetrile, cephalexin, cephaloglycin, cephaloridine, cephalothin, cephapirin, cephradine, cyclacillin, epicillin, furazlocillin, hetacillin, lenampicillin, levopropylcillin, mecillinam, mezlocillin, penicillin G, penicillin V, phenethicillin, piperacillin, pivampicillin, sarmoxicillin, sarpicillin, suncillin, talampicillin and ticarcillin, including the pharmaceutically acceptable salts thereof. The names employed for these beta-lactams are generally USAN, i.e., United States Adopted Names.

Also preferred are combinations of the betalactamase inhibitors of the invention with 7-[D-(2-[4-carboxy-5-imidazolecarboxamido])-2-phenylacetamido]-3[4-(2-sulfonatoethyl)pyridinium]-3-cephem-4-carboxylic acid.

The present invention further encompasses a method of treating a bacterial infection in a mammal by topical, oral or parenteral administration of an antibacterially effective amount of a pharmaceutical composition of the preceding paragraphs; a pharmaceutical composition comprising an antibacterially effective amount of a compound of the formula (I) per se, and a method of treating bacterial infections with a antibacterially effective amount of a compound of the formula (I) per se.

Finally, the present invention encompasses intermediate compounds as follows:

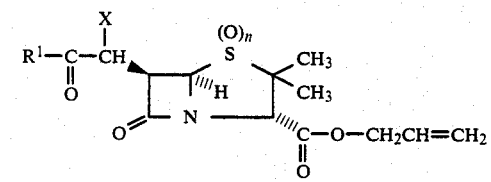
(II)

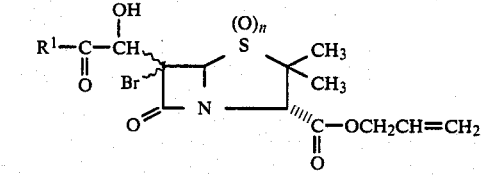
(III)

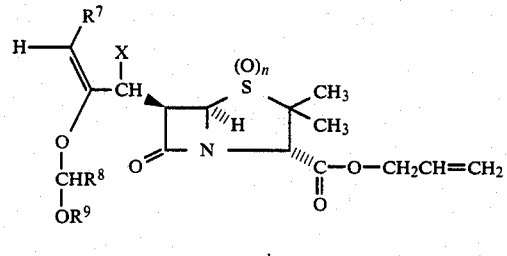
(IV)

and

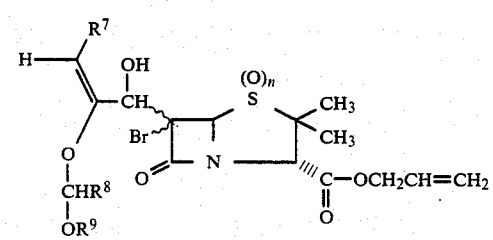
(V)

wherein $n$, $X$ and $R^1$ are as defined above; except that hydroxy groups are optionally protected by dimethyl-t-butylsilyl groups and primary and secondary amino groups are protected by benzyloxycarbonyl groups;

$R^7$ is phenyl, naphthyl, furyl, benzothienyl, $(C_8-C_{11})$-N-alkylindolyl, pyridyl, quinolyl, isoquinolyl or quinoxalinyl;

or one of said groups $R^7$ optionally substituted on aromatic or heterocyclic carbon with fluoro, chloro, bromo, $(C_1-C_4)$alkyl, phenyl, $(C_1-C_4)$alkoxy, di[($C_1-C_4$)alkyl]amino, where said disubstituents may be on the same or different, with the provisos that no tetrahedral carbon is simultaneously bonded to a nitrogen or oxygen atom and a fluoro, chloro, bromo or second nitrogen or oxygen atom; and that no nitrogen is quaternary;

$R^8$ is hydrogen or methyl; and
$R^9$ is methyl or ethyl.

In the compounds (II) and (III) the preferred values of $R^1$ are generally as those defined above for the compound (I). In the compounds (IV) and (V) the preferred values are $R^7$ as phenyl or thienyl, $R^8$ as methyl and $R^9$ as ethyl. The hydroxy substituted carbon of the side chain is preferably in the configuration:

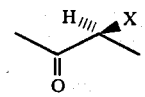

designated as the S-configuration when there is no Br at C.6 and designated as the R-configuration when there is a Br substituent at C.6.

DETAILED DESCRIPTION OF THE INVENTION

The compounds of the formula (I) are most generally prepared by the following synthetic route:

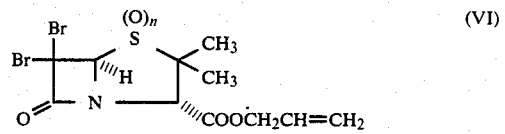
(VI)

| | |
|---|---|
| Method A | (1) CH₃MgBr<br>(2) R¹COCHO (with primary and secondary amino groups protected and hydroxy groups optionally protected) |

↓

(III)

| | |
|---|---|
| Methods B,C,F and G | (1) (n-C₄H₉)₃SnH (Method B)<br>(2) Optional deprotection of hydroxy groups (Method G)<br>(3) Optional mono- or dioxidation of sulfur if not already oxidized (Method F)<br>(4) Optional acylation (Method C) |

↓

(II)

| | |
|---|---|
| Methods D and E | (1) Cleavage of allyl esters (Method D) or of benzyl esters (Method E)<br>(2) Deprotection of any primary and secondary amino groups (Method E) |

↓

(I)

In the first stage of the above synthetic route, the dibromo compound (VI) is dissolved in a dry, reaction-inert solvent such as tetrahydrofuran, toluene, methylene chloride, or combination thereof, which will remain liquid at the reaction temperature, cooled to $-50°$ to $-100°$ C., and reacted with substantially one molar equivalent of a Grignard reagent such as methylmagnesium bromide in an ethereal solvent such as diethyl ether (said reagent formed by standard methods in the laboratory, or purchased commercially), generally added portionwise over a 5-15 minutes while maintaining the same low reaction temperature. After stirring for 10-30 minutes to allow complete reaction and equilibration, the glyoxal $$R^1-\overset{O}{\underset{\|}{C}}-\overset{O}{\underset{\|}{C}}-H \quad (X)$$

is added, optionally dissolved in the same or another reaction inert solvent, in like manner. After stirring 10 minutes-1 hour at the same low temperature, the reaction mixture is quenched into a weak acid such as acetic acid or an acidic salt such as ammonium chloride, and the intermediate of the formula (III) isolated by standard methods such as evaporation, extraction and chromatography, including chromatographic separation of epimers corresponding to R- and S- side chain configurations:

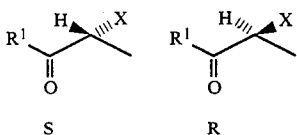

where stability and differences in polarity permit. In this reaction step, the R-epimer generally predominates, particularly when the solvent is toluene.

As used here and hereinafter, the expression "reaction-inert solvent" refers to any solvent which does not interact with starting materials, reagents, intermediates or products in a manner which significantly reduces the yield of the desired product.

The starting dibromo compound is readily prepared from the corresponding penicillanic acid salt and allyl bromide, such as by the method exemplified in the preparation of allyl 6,6-dibromopenicillanate, specifically described below.

The required glyoxals of the formula (X) are preferably freshly prepared or freshly purified. Their preparation is as extensively exemplified below. One general method for preparation of the required glyoxals is via the following synthetic route:

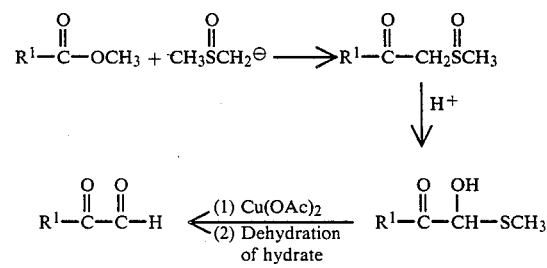

Another method employs acylation with N-(dimethoxyacetyl)morpholine, e.g.,

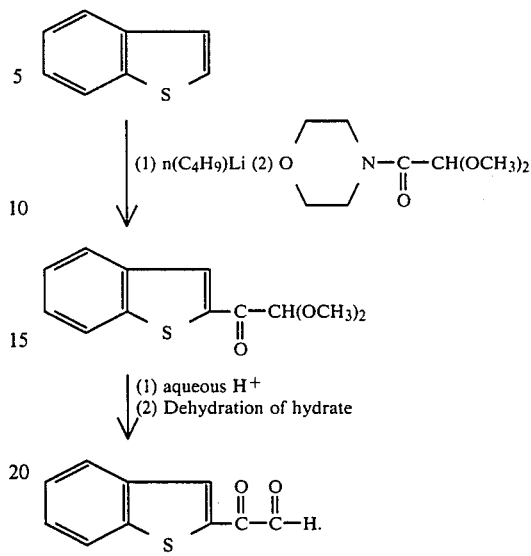

Another, older general method is:

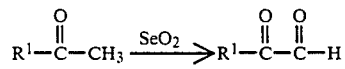

(see Wagner and Zook, Synthetic Organic Chemistry, John Wiley and sons, Inc., 1953, pp. 288-9, 381-2).

The C.6 stereochemistry of the intermediate of the formula (III) has not been specified. However, C.6 stereochemistry is set as 6-beta in the tributyltin hydride debromination step, regardless of stereochemistry at the 6-position in compound (III). This debromination step is optionally carried out in the presence of small amounts of a free radical initiator such as 2,2'-azobisisobutyronitrile (AIBN), in a reaction inert solvent as benzene or toluene. The temperature is usually elevated (e.g., 60°-100° C.), such that reaction occurs in a reasonable period of time, but not so high as to cause undue thermal degradation. Products are once again recovered and purified by standard methods, as noted above, with chromatographic separation of R- and S-sidechain epimers most often carried out at this stage.

If 1-oxide or 1,1-dioxide are desired, and sulfur is not already in the desired oxidation state, the sulfur is oxidized at this stage in the synthetic sequence. In order to avoid unduly complex mixtures when the 1-oxides (sulfoxides) are desired, said oxidation is preferably carried out on separated R- or S-sidechain epimers. To form a mixture of the 1-alpha-oxide (S⃞O) and 1-beta-oxide (S→O) of the formula (II) wherein n is 1, the corresponding sulfides (II, n=0) are oxidized with substantially 1-molar equivalent of a peracid, conveniently m-chloroperbenzoic acid, in a reaction-inert solvent such as methylene chloride or ethyl acetate, at 0°-50° C., conveniently at ambient temperatures. The resulting mixture is isolated by standard methods such as extraction, evaporation, crystallization and chromatography, including chromatographic separation of the 1-alpha- and 1-beta-oxides at this or a later stage of the synthetic sequence, as desired. To form the 1,1-dioxide (sulfone) of the formula (II) wherein n=2, the sulfide is oxidized with at least two molar equivalents of the peracid, otherwise under conditions and with isolation as described above for sulfoxides.

If the desired end product contains X as $OCOR^2$, acylation is also preferably carried out at this stage of the synthesis. Standard methods of acylation are employed, such as the appropriate anhydride (or acetoformic acid reagent for formylation) in the presence of pyridine. Likewise, propenyl groups protecting hydroxyl groups are preferably removed at this stage of the synthesis, conveniently by mild acid or $HgCl_2/HgO$ catalyzed hydrolysis at ambient temperature.

In the final stage of the synthesis of the compounds (I) wherein R is hydrogen, the allyl protecting group is removed, usually with simultaneous formation and isolation of the product as a sodium or potassium salt. This transformation is conveniently carried out by reaction with substantially one molar equivalent of sodium or potassium ethylhexanoate (or other lipophilic carboxylate salt) in the presence of catalytic amounts of tetrakis(triphenylphosphine)palladium (typically 5 mole %) and triphenylphosphine (typically 20-25 mole %) in a reaction inert solvent, preferably one in which the reactants are soluble and the alkali metal salt of the desired product is relatively insoluble. Particularly well suited in the present instance is the potassium salt of 2-ethylhexanoate in ethyl acetate as solvent. If the salt does not precipitate, it can be precipitated by addition of a further non-solvent such as ether; or alternatively extracted into water and recovered by freeze drying. Even when the product precipitates or is precipitated from the reaction mixture, it is usually taken up in water, impurities filtered or extracted away and reisolated by freeze drying. Temperature is not critical in this deprotection step, e.g., 0°-50° C. is usually satisfactory. Most conveniently, ambient temperature is employed.

If desired, the salt is converted to the free acid form, during or after isolation, by standard methods, e.g., acidification of an aqueous solution of the salt, with extraction of the free acid into a water immiscible organic solvent.

Other pharmaceutically-acceptable cationic salts of the present invention are also readily prepared by standard methods. For example, an equivalent of the corresponding cationic hydroxide, carbonate or bicarbonate or of an amine, is combined with the carboxylic acid in an organic or aqueous solvent, preferably at reduced temperature (e.g., 0°-5° C.), with vigorous agitation and slow addition of the base. The salt is isolated by concentration and/or the addition of a non-solvent.

Likewise pharmaceutically-acceptable acid addition salts of the present invention are readily prepared by standard methods. For example, an equivalent of the acid is combined with the free amine form of the compound in an organic or aqueous organic solvent. The salt is isolated by concentration and/or the addition of a non-solvent. As noted above, the salt is alternatively isolated directly from a reaction mixture, i.e., without isolation of the free amine, otherwise using similar techniques of concentration and/or addition of a non-solvent.

When benzyl is used in place of allyl as a protecting group, or primary or secondary amino groups are protected by benzyloxycarbonyl groups, said protecting groups are removed by hydrogenolysis over a noble metal catalyst in a reaction inert solvent, using methods generally well known in the art. The preferred noble metal catalyst is palladium, most preferably palladium on a support such as carbon or diatomaceous earth. Temperature and pressure are not critical; but are preferably mild (e.g. 0°-50° C., conveniently ambient temperature and 1 to 8 atmospheres), minimizing side reactions.

Intermediate compounds of the formula (II) wherein $R^1$ contains —$CH_2$— adjacent to the carbonyl group are preferably prepared by the following route:

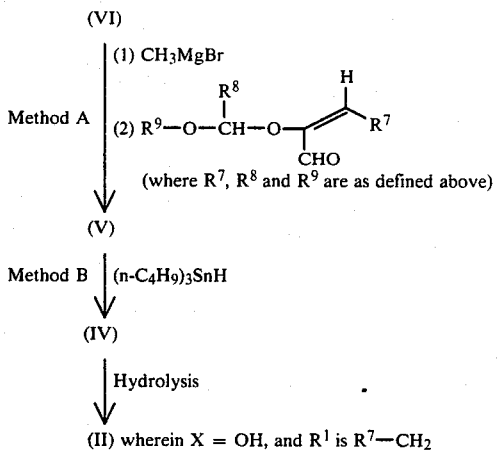

The Grignard reaction and tributyltin hydride debrominations are carried out in the manner described above. Hydrolysis is accomplished under mild conditions. This process is most preferred when $R^7$ is phenyl or thienyl.

The starting aldehyde required for this synthesis is readily prepared by base catalyzed condensation of an aromatic or heterocyclic aldehyde with a 2-[1-(alkoxy)alkoxy]acetaldehyde, with concurrent dehydration:

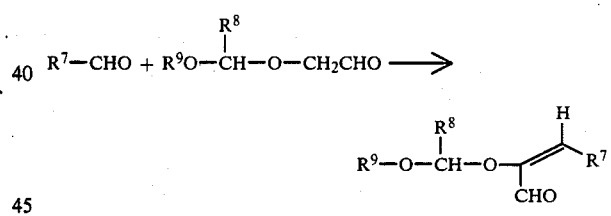

The compounds of the formula (I) wherein R represents an in vivo hydrolyzable ester are prepared from the corresponding free acids or cationic salts according to known methods, readily identified by those skilled in the penicillin art (see for example U.S. Pat. Nos. 3,951,954; 4,234,579; 4,287,181; 4,342,693; 4,452,796; 4,342,693; 4,348,264; 4,416,891; and 4,457,924). Preferred methods of preparation are exemplified below. If desired, an ester containing a basic amine or carboxylic acid function is converted to an acid addition salt or cationic salt, respectively, according to the methods of the immediately preceding paragraphs.

Conjugate esters of the above formula (I) wherein R is an acylmethyl radical derived from a conventional penicillin are conveniently made from a salt (preferably the tetrabutylammonium salt) of the corresponding compound of the formula (I) wherein R is hydrogen, and the halomethyl ester (preferably the iodomethyl ester) of the penicillin, in protected form when the penicillin contains primary or secondary amino or carboxylic acid functionality. The preferred protecting groups are removed by facile hydrolysis, rather than hydrogenolysis, particularly when $R^1$ is aromatic, heteroaromatic or otherwise contains a double bond in conjugation with the side chain carbonyl group. Exemplary are enamines (e.g., acetoacetate derivatives) and phenyl esters. Exemplary is the preparative route for compounds of the formula (II) wherein R is in the form of the preferred radical of the formula (A) defined above. If not already in hand, the requisite ampicillin is first converted to a cationic salt. The salt can be an inorganic salt such as that of an alkali or alkaline earth metal, or an organic salt such as that of a tertiary amine or a quaternary ammonium salt. The latter type salt is preferred, the tetrabutylammonium salt being most preferred. The required cationic salts are readily prepared by methods standard in the art. For example, the tetrabutylammonium salt is conveniently prepared by combining equivalent amounts of the acid form of the penicillin derivative and tetrabutylammonium hydroxide in a mixture of water and a reaction inert immiscible organic solvent such as chloroform. The organic layer is separated, dried (with a drying agent or azeotropically) and the salt recovered by evaporation to dryness.

The above salts are then reacted with at least one equivalent of a ($C_1$-$C_3$) alkyl acetoacetate, conveniently methyl acetoacetate, in a reaction inert solvent at 10°-70° C. It is preferred to use an excess of the acetoacetate ester, in order to facilitate complete reaction, and indeed the ester itself can serve as solvent for the reaction. In this manner, there is obtained an intermediate enamine compound of the formula:

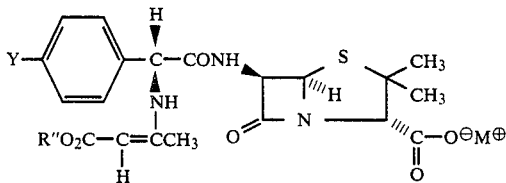

wherein Y is as defined above, R" is ($C_1$-$C_3$)alkyl and M+ is a cation as noted in the preceding paragraph. Water formed in the process is generally removed either by use of a drying agent or by azeotropic distillation, e.g., with benzene, and the product recovered by evaporation.

The above enamine, still as the salt (preferably the tetrabutylammonium salt) is then reacted under typical nucleophilic displacement conditions with at least one equivalent of chloromethyl iodide.

When the salt is a quaternary salt such as the tetrabutylammonium salt, the nucleophilic displacement occurs rapidly under mild conditions, e.g., at 0°-50° C., conveniently at ambient temperature, in a reaction inert solvent such as acetone.

Although a chloromethyl ester can be used directly in the next step, it is preferred to first convert the chloromethyl ester to the corresponding iodomethyl ester. Contact of the chloromethyl ester with sodium iodide in acetone at 0°-50° until reaction is substantially complete represents conditions particularly well-suited to this purpose. The iodomethylester is then reacted, in a reaction inert solvent at 0°-50° C., with a salt of the desired compound of the formula (I) wherein R is hydrogen, prepared as described above. Again, the preferred salt is the tetrabutylammonium salt.

Finally the above enamine esters are hydrolyzed under mildly acidic conditions in an aqueous solvent, comprising simply water or water and a water miscible or immiscible reaction inert organic solvent; at 0°-50° C., conveniently at ambient temperature. The two phase system of water and ethyl acetate at ambient temperature represents particularly suitable conditions. Conveniently, one equivalent of a strong acid such as HCl or a sulfonate salt is used, and the product is isolated in the form of that acid addition salt.

As indicated above, some of the compounds of the formula (I), generally those wherein R is hydrogen, have in vitro antibacterial activity. Such activity is demonstrated by measuring the minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta. Pathologica et Microbiologia Scandinav*, Supp. 217, Section B: 64-68 [1971]), and employs brain heart infusion (BHI) agar and an inocula replicating device. Overnight growth tubes are diluted 100 fold for use as the standard inoculum (20,000-10,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye.

Those compounds of the formula (I) having said in vitro antibacterial activity are thus useful as industrial antimicrobials, for example in water treatment, slime control, paint preservation and wood preservation, as well as for topical application in mammals. In the case of use of these compounds for topical application, it is often convenient to admix the active ingredient with a non-toxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

As also indicated above, the compounds of the formula (I) are generally of sufficient antibacterial activity to be useful as systemic antibacterial agents, particularly when the sidechain is in the preferred S-configuration. In determining such in vivo activity, acute experimental infections are produced in mice by the intraperitoneal inoculation of the mice with a standardized culture of the test organism suspended in 5 percent hog gastric mucin. Infection severity is standardized so that the mice receive a lethal dose of the organism (the lethal dose is the minimum inoculum of organism required to consistently kill 100 percent of the infected, non-treated control mice). The test compound of the formula (I) is administered at various dosage levels, p.o. or i.p., to groups of infected mice. At the end of the test, the activity of the mixture is assessed by counting the number of survivors among treated animals at a given dose. Activity is expressed as the percentage of animals which survive at a given dose, or calculated as $PD_{50}$ (dose which protects 50% of the animals from infection).

Even more generally, the compounds of the formula (I) are of special value as potent inhibitors of microbial beta-lactamases. By this mechanism they increase their own antibacterial effectiveness or the antibacterial effectiveness of a conventional beta-lactam antibiotic (penicillin or cephalosporin) against many microorganisms, particularly those which produce a beta-lactamase. Thus the ability of the said compounds of the formula (I) in vitro is also evaluated by the ability of the compounds (I) wherein R is H to inhibit the hydrolysis of certain beta-lactam antibiotics by beta-lactamase enzymes. For example, the hydrolysis of ampicillin and penicillin G is determined by the microiodometric method of Novick (Biochem. J. 83, 236 (1962)], while cephaloridine hydrolysis is measured by following the decrease in ultraviolet absorbance at 255 nm [O'Callaghan et al., Antimicrob. Agents Chemother. 1968, pp. 57-63 (1969)]. Conditions for both assays are identical: 0.5M potassium phosphate, pH 6.5 and 37° C. Reactions are initiated by the addition of the cell-free beta-lactamase, except in the case of preincubation experiments in which the inhibitor and enzyme were incubated together in the assay mixture for 10 minutes before initiation of the reaction by addition of substrate. With the cell-free extracts of Staphylococcus aureus, Escherichia coli, Klebsiella pneumoniae and Pseudomonas aeruginosa, the substrate is ampicillin at 33 micro M (13 microg./ml.). Typical specific activities of the beta-lactamase preparations are, respectively, 6,019, 88,970, 260 and 76 micromol/hr. per mg. of protein. Penicillin G (33 micromol) is the substrate used with the Enterobacter cloacae beta-lactamase, which shows a typical specific activity of 10,080 micromol/hr. per mg. of protein.

Cell-free extracts are prepared by sonic treatment (using three 30-s bursts at 4° C. except for S. aureus, which is broken with a French press) of cultures grown in brain heart infusion on a rotary shaker incubator. For the S. aureus, P. aeruginosa, and E. cloacae strains, de novo synthesis of beta-lactamase is induced by growing a log-phase culture in the presence of a sublethal concentration of penicillin G at 100, 1,000, and 300 microg./ml., respectively, for 2.5 hours.

The ability of compounds of the formula (I) to increase the effectiveness of a beta-lactam antibiotic can be appreciated by reference to experiments in which the MIC values of the antibiotic alone, and a compound of the formula (I) (having R as hydrogen) alone, are determined. These MIC's are then compared with the MIC values obtained with a combination of the given antibiotic and the compound of the formula (I), wherein R is hydrogen. When the antibacterial potency of the combination is significantly greater than would have been predicted from the potencies of the individual compounds, this is considered to constitute enhancement of activity. The MIC values of combination are measured using the method described by Barry and Sabath in "Manual of Clinical Microbiology", edited by Lenette, Spaulding and Truant, 2nd Edition, 1974, American Society for Microbiology.

The compounds of the formula (I) also generally enhance the antibacterial effectiveness of beta-lactam antibiotics in vivo. That is, they lower the amount of the antibiotic which is needed to protect mice against an otherwise lethal inoculum of certain beta-lactamase producing bacteria. Such in vivo tests are carried out in the manner described above for single agents, but in this case the mice are dosed with a combination of the test compound (I) wherein R is hydrogen or an in vivo hydrolyzable ester and the beta-lactam antibiotic under study.

In determining whether a particular strain of bacteria is sensitive to a particular compound of the formula (I) wherein R is an acyloxymethyl group derived from a beta-lactam antibiotic, it is not necessary to carry out an in vivo test. Instead, the MIC of a 1:1 molar mixture of a compound of the formula (I) wherein R is hydrogen, and the appropriate beta-lactam antibiotic is measured according to methods described above.

The ability of the compounds of formula (I), wherein R is hydrogen or a in vivo hydrolyzable ester, to enhance the effectiveness of a beta-lactam antibiotic against beta-lactamase producing bacteria makes them valuable for co-administration with beta-lactam antibiotics in the treatment of bacterial infections in mammals, particularly man. In the treatment of a bacterial infection, the compound of the formula (I) can be comingled with the beta-lactam antibiotic, and the two agents thereby administered simultaneously. Alternatively, the compound of the formula (I) can be administered as a separate agent during a course of treatment with a beta-lactam antibiotic. In some instances it will be advantageous to pre-dose the subject with the compound of the formula (I) before initiating treatment with a beta-lactam antibiotic.

When simultaneously administering a compound of formula (I) and a beta-lactam antibiotic, it is preferred to administer a mixture of (I) and the beta-lactam antibiotic in a single formulation. Such a pharmaceutical composition will normally comprise the beta-lactam antibiotic, the compound of formula (I) and from about 5 to about 80 percent of a pharmaceutically acceptable carrier or diluent by weight. Said carrier or diluent is chosen on the basis of the intended mode of administration. For oral administration, tablets, capsules, lozenges, troches, powders, syrups, elixirs, aqueous solutions and suspension, and the like are used, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying or suspending agents. If desired, certain sweetening and/or flavoring agents can be added. For parenteral administration, which includes intramuscular, intraperitoneal, subcutaneous, and intravenous injection, sterile solutions of the active ingredient are usually prepared, and the pH of the solutions are suitably adjusted and buffered. For intravenous use, the total concentration of solutes should be controlled to render the preparation isotonic. When dosed separately, compounds of the formula (I) are formulated in like manner.

When using the compounds of formula (I) in combination with another beta-lactam antibiotic, said compounds are administered orally or parenterally, i.e., intramuscularly, subcutaneously or intraperitoneally. Although the prescribing physician will ultimately decide the dosage to be used in a human subject, the ratio of the daily dosages of the compounds of formula (I)

and the beta-lactam antibiotic will normally be in the range from about 1:10 to 3:1 by weight. Additionally, when using the compounds of formula (I) in combination with another beta-lactam antibiotic, the daily oral dosage of each component will normally be in the range from about 10 to about 200 mg. per kilogram of body weight and the daily parenteral dosage of each component will normally be about 5 to about 50 mg. per kilogram of body weight. These daily doses will usually be divided. In some instances, the prescribing physician will determine that dosage outside these limits are necessary.

As will be appreciated by one skilled in the art, some beta-lactam compounds are effective when administered orally or parenterally, while others are effective only when administered by the parenteral route. When a compound of formula (I) is to be used simultaneously (i.e. comingled) with a beta-lactam antibiotic which is effective only on parenteral administration, a combination formulation suitable for parenteral use will be required. When a compound of formula (I) is to be used simultaneously (comingled) with a beta-lactam antibiotic which is effective orally or parenterally, combination suitable for either oral or parenteral administration can be prepared. Additionally, it is possible to administer preparations of the compounds of formula (I) orally, while at the same time administering a further beta-lactam antibiotic parenterally, and it is also possible to administer preparation of the compounds of formula (I) parenterally, while at the same time administering the further beta-lactam antibiotic orally.

It is the capacity of compounds of the formula (I), wherein R is an acyloxymethyl derivative of a beta-lactam antibiotic, to hydrolyze and provide both the compounds of the formula (I) where R is hydrogen and the beta-lactam antibiotic which enhances the activity and broadens the antibacterial spectrum of these compounds relative to the use of an equivalent amount of beta-lactam antibiotic alone.

When using one of the present antibacterial compounds of the formula (I) alone for control of bacterial infections in a mammal, particularly man, the compound is administered alone, or mixed with pharmaceutically acceptable carriers or diluents, in the manner described above.

When using the more active compounds of the formula (I) alone to control bacterial infections, the daily dosage will be similar to those of other clinically useful beta-lactam antibiotics. Although the prescribing physician will ultimately decide the dosage to be used in a human subject, these compounds will normally be used orally at dosages in the range from about 20 to about 100 mg. per kilogram of body weight per day, and parenterally at dosages from about 10 to about 100 mg. per kilogram of body weight per day, usually in divided doses. In some instances, the prescribing physician will determine that dosages outside these limits are needed.

The present invention is illustrated by the following examples. However, it should be understood that the invention is not limited to the specific details of these examples. Abbreviations are used as follows: THF for tetrahydrofuran; AIBN for azo-bis-isobutyronitrile; DMAP for 4-dimethylaminopyridine; DMF for dimethylformamide; DMSO for dimethylsulfoxide; tlc for thin-layer chromatography on silica gel plates, with detection by u.v. and/or KMnO$_4$ spray; $^1$H-nmr for proton nuclear magnetic resonance spectra, delta in ppm in CDCl$_3$ at 60 MHz, unless otherwise specified.

Unless otherwise specified, all operations were carried out at ambient temperature; specified temperatures are in °C.; all solutions were dried over Na$_2$SO$_4$; all solvents were stripped in vacuo; and pH adjustments were with dilute NaOH or dilute HCl, as necessary to achieve the desired pH.

METHOD A—GRIGNARD REACTIONS

EXAMPLE A1

Allyl 6-Bromo-6-[1-hydroxy-2-oxo-2-(phenyl)ethyl]penicillanate

Under N$_2$, allyl 6,6-dibromopenicillanate (23.4 g., 0.059 mol) was dissolved in 200 ml. THF and cooled to −78°. By syringe, methylmagnesium bromide (19 ml. of 3.1M in ether, 0.059 mol) was added over 10 minutes, maintaining the −78° temperature as the mixture was stirred for an additional 15 minutes. Meanwhile, freshly prepared phenylglyoxal (9 g., 0.067 mol) was separately dissolved in 100 ml. THF and cooled to −78°. The cold Grignard solution was transferred to the glyoxal solution via cannula over 10–15 minutes and the mixture stirred 30 minutes at −78°. To quench, the reaction, it was poured into an equal volume of saturated NH$_4$Cl and extracted 3×500 ml. ether. The ether extracts were combined, washed with 500 ml. H$_2$O and then 500 ml. brine, dried, and evaporated to an oil (28 g.) which was flash chromatographed on 700 g. of silica gel using 1:1 ether:hexane as eluant and monitoring by tlc. Product fractions were combined and evaporated to yield title product as an oil, 12.0 g. (45%); tlc Rf 0.6 (1:1 ethyl acetate:hexane), 0.4 (1:2 ethyl acetate:hexane). It is understood that this product is a mixture of R- and S-sidechain diastereoisomers of unspecified C.6 stereochemistry.

EXAMPLE A2

Benzyl 6-Bromo-6-[1-hydroxy-2-oxo-2-(phenyl)ethyl]penicillanate

According to the method of Example A1, except to use ethyl acetate in place of ether for extraction, benzyl 6,6-dibromopenicillanate (8.35 g., 0.021 mol) and phenylglyoxal (3.0 g., 0.024 mol) were converted to title product which was purified by "flash" chromatography on a shallow bed of silica gel using 4:1 hexane:ethyl acetate as eluant to yield 1.8 g.; tlc Rf 0.5 (2:1 hexane:ethyl acetate); understood to be a 2:1 mixture of R- and S-sidechain diastereoisomers of unspecified C.6 stereochemistry; $^1$H-nmr: 1.36 and 1.59 (2s, 3H), 1.59 (s, 3H); 4.14 and 4.36 (2d, 1H), 4.43 and 4.53 (2s, 1H), 5.22 (s, 2H), 5.48 and 5.81 (2s, 1H); 5.59 and 5.65 (2d, 1H); 7.32–7.93 (m, 10H).

EXAMPLE A3

Allyl 6-Bromo-6-(R- and S-1-hydroxy-2-oxopropyl)penicillanate

According to the method of Example A1, except to use ethyl acetate in place of ether for extraction from the NH$_4$Cl quench, allyl 6,6-dibromopenicillanate (2.7 g., 0.0069 mol) and methyl glyoxal (0.5 g., 0.0069 mol) were converted to crude title product as an oil (2.6 g.) which was flash chromatographed on silica gel with 3:1 hexane:ethyl acetate as eluant and monitoring by tlc to provide title product in two isomeric forms; less polar (lp), the sidechain R-epimer; and more polar (mp), the sidechain S-epimer; both of unestablished C.6 stereochemistry.

R-epimer (lp); 180 mg; tlc Rf 0.75 (1:1 ethyl acetate:hexane); 1H-nmr 1.49 (s, 3H), 1.67 (s, 3H), 2.46 (s, 3H), 4.19 (d, 1H, J=5.7Hz), 4.58 (s, 1H), 4.67 (m, 3H), 5.37 (m, 2H); 5.63 (s, 1H); 5.91 (m, 1H); ir (CHCl$_3$) cm$^{-1}$; 3490 (b), 3950 (w), 1795 (s), 1750 (s), 1735 (s), 1380 (m), 1265 (m), 1205 (m).

S-epimer (mp); 115 mg.; tlc Rf 0.65 (1:1 ethyl acetate:hexane); $^1$H-nmr 1.49 (s, 3H), 1.67 (s, 3H), 2.39 (s, 3H), 4.12 (m, 1H), 2.58 (s, 1H), 2.68 (m, 3H), 5.36 (m, 2H), 5.68 (s, 1H), 5.93 (m, 1H); ir (CHCl$_3$) cm$^{-1}$ 3550 (b), 2990 (w), 1795 (s), 1750 (s), 1380 (m,), 1310 (m), 1250 (m), 1100 (m).

EXAMPLE A4

Allyl 6-Bromo-6-[1-hydroxy-2-oxo-2-(2-furyl)ethyl]penicillanate

According to the method of the preceding Example, except to use 2:1 hexane:ethyl acetate as eluant, allyl, 6,6-dibromopenicillanate (10.0 g., 0.025 mol) and freshly prepared 2-furylglyoxal (3.5 g., 0.028 mol) were converted to instant title product as a mixture of diastereoisomers, 60 mg.; tlc Rf 0.5 (1:1 ethyl acetate:hexane); $^1$H-nmr 1.42 (s, 3H), 1.63 (s, 3H), 4.49 and 4.52 (2s, 1H), 4.68 (m, 3H), 5.36 (m, 3H), 5.89 (d, 1H), 5.92 (m, 1H), 6.59 (m, 1H), 7.41 (m, 1H), 7.63 (m, 1H); ir (CDCl$_3$) cm$^{-1}$ 3500 (b), 2940 (w), 1795 (s), 1750 (s), 1680 (s), 1575 (w), 1470 (m), 1380 (m), 1310 (m), 1090 (m), 1035 (m).

EXAMPLE A5

Allyl 6-Bromo-6-[1-hydroxy-2-oxo-2-(4-methoxyphenyl)ethyl]penicillanate

Except that 4-methoxyphenylglyoxal monohydrate (6.5 g.) in THF was rendered anhydrous by stirring for 3 hours with 20 g. of 3A type molecular sieves at ambient temperature prior to treatment with the Grignard solution, and to use ethyl acetate in place of ether for extraction of the quenched reaction mixture, the method of Example A1 was employed to convert allyl 6,6-dibromopenicillanate (20 g.) to crude title product, 17.2 g., as an oil. A portion (10 g.) was flash chromatographed on 400 g. of silica gel, using 1:1 ether:hexane as eluant to yield title product as a mixture of diastereoisomers, 1.57 g., $^1$H-nmr 1.41 and 1.45 (2s, 3H), 1.61 and 1.62 (2s, 3H), 3.85 (m, 5H), 4.38 and 4.55 (2s, 1H), 4.65 (m, 2H), 5.35 (m, 2H), 5.55 and 5.82 (2s, 1H), 5.91 (m, 1H), 6.97 and 8.01 (2m, 4H).

EXAMPLE A6

Allyl 6-Bromo-6-[R- and S-1-hydroxy-2-oxo-2-(2-thienyl)ethyl]penicillanate

Using 4A type molecular sieve in the method of the preceding Example, freshly distilled (2-thienyl)glyoxal (1.9 g., 0.0136 mol) and allyl 6,6-dibromopenicillanate (5.2 g., 0.013 mol) were converted to crude products (4 g.), flash chromatographed on silica gel with 2:1 hexane:ethyl acetate as eluant to yield title products as a mixture of diastereoisomers as an oil, 1.3 g.; tlc Rf 0.7 (1:1 ethyl acetate:hexane); $^1$H-nmr 1.45 and 1.46 (2s, 3H), 1.62 (s, 3H), 4.44 and 4.52 (2s, 1H), 4.45 (b, 1H), 4.5–4.7 (m, 2H), 5.24–5.50 (m, 2H), 5.6 and 5.84 (2s, 1H), 5.90 (m, 1H), 7.18 (m, 1H), 7.80 (m, 1H), 7.9 (m, 1H); ir (CHCl$_3$) cm$^{-1}$: 3550 (b), 2995 (w), 1795 (s), 1750 (s), 1670 (s), 1610 (w), 1410 (m), 1360 (m), 1275 (s), 1050 (m).

This preparation was repeated using 6.0 g. (0.042 mol) of (2-thienyl)glyoxal and 16 g. (0.04 mol) of allyl 6,6-dibromopenicillanate to yield crude title products (16 g.) which was more carefully chromatographed using 3:2 ether:hexane as eluant to yield R- and S-epimers, of unspecified C.6 stereochemistry, as follows:

S-epimer (lp), 1.3 g.; tlc Rf 0.6 (3:2 ether:hexane), 0.7 (1:1 ethyl acetate:hexane).

Mixed epimers, 1.5 g.

R-epimer (mp) 2.8 g.; tlc 0.5 (3:2 ether:hexane), 0.7 (1:1 ethyl acetate:hexane)

EXAMPLE A7

Allyl 6-Bromo-6-[1-hydroxy-2-oxo-2-(1-naphthyl)ethyl]penicillanate

By the procedure of Example A2, (1-naphthyl)glyoxal (4.25 g., 0.023 mol) and allyl 6,6-dibromopenicillanate (9.21 g., 0.023 mol) were converted to instant title product, initially isolated as a dry foam which was chromatographed on 400 g. of silica gel with 1:1 ether:hexane as eluant to produce purified title product as a mixture of isomers, 5.38 g.; tlc Rf 0.3 (1:1 hexane:ether); $^1$H-nmr 1.33, 1.41 and 1.51 (3s, 6H), 4.40 and 4.49 (2s, 1H), 4.65 (m, 3H), 5.55 (m, 2H), 5.46 and 5.85 (2s, 1H), 5.95 (m, 1H), 7.40–8.78 (m, 7H).

EXAMPLE A8

Allyl 6-Bromo-6-[R-2-(1-(ethoxy)ethoxy)-1-hydroxy-3-(phenyl)prop-2-enyl]penicillanate With stirring under N$_2$, allyl 6,6-dibromopenicillanate (4.25 g., 0.0106 mol) was dissolved in 100 ml. toluene and cooled to −78°. Methylmagnesium bromide (34.1 ml. of 3.1M in ether, 0.106 mol) was added as in Example A1. 2-[1-(Ethoxy)ethoxy]-3-phenylpropenal (2.13 g., 0.0097 mol) in 10 ml. toluene was added dropwise and stirring continued at −78° for 1.5 hours. The mixture was poured into excess NH$_4$Cl, diluted with 200 ml. ether, and the layers separated. The aqueous layer was extracted 2×100 ml. fresh ether. The three organic layers were combined, washed with 100 ml. saturated NaHCO$_3$, dried over MgSO$_4$ and stripped to yield title product as an oil, 5.95 g.; tlc Rfs 0.32 and 0.38 (1:1 ether:hexane). The product is essentially sidechain R diastereoisomer with R- and S-epimers in the 1-(ethoxy)ethoxy sidechain and of unspecified C.6 stereochemistry.

EXAMPLE A9

Allyl 6-Bromo-6-[R-2-(1-(ethoxy)ethoxy)-1-hydroxy-3-(2-thienyl)prop-2-enyl]penicillanate By the method of the preceding Example, allyl 6,6-dibromopenicillanate (2.06 g., 0.0052 mol) and 2-[1-ethoxy)]-3-(2-thienyl)propenal (1.17 g., 0.0052 mol) were converted to instant title product as an oil, 3.1 g., essentially all sidechain R-diastereoisomer(s) which are of unspecified C.6 stereochemistry; tlc Rf 0.28 (1:1 ether:hexane); $^1$H-nmr 1.22 (m, 3H), 1.47 (s, 3H), 1.60 (d, 3H), 1.69 (s, 3H), 3.70 (m, 2H), 4.34 (m, 1H), 4.61 (s, 2H), 4.74 (m, 3H), 5.44 (m, 2H), 5.94 (m, 1H), 6.04 (s, 1H), 6.45 (ABq, 1H), 7.17 (m, 3H).

EXAMPLE A10

Allyl 6-Bromo-6-[1-hydroxy-2-oxo-2-(4-dimethylaminophenyl)ethyl]penicillanate (4-Dimethylaminophenyl)glyoxal monohydrate (3.5 g., 0.018 mol), prepared according to Preparation 22 below, was dissolved in 150 ml. benzene and refluxed for 18 hours (employing a Dean-Stark trap to remove water), stripped to solids, taken up in 50 ml. dry THF, further dried over molecular sieves, and filtered to yield anhydrous (4-dimethylaminophenyl)glyoxal, 0.18 mol, in 50 ml. THF. The latter was reacted with allyl 6,6-dibromopenicillanate (7.82 g., 0.019 mol) and methylmagnesium bromide according to the method of Example A2 to yield chromatographed title product as mixture of diastereoisomers (R and S in the sidechain, unspecified at the 6-position), oil, 2.15 g.; $^1$H-nmr 1.42 and 1.50 (2s, 3H), 1.63 (s, 3H), 3.11 (s, 6H), 4.05 (m, 1H), 4.40 and 4.60 (2s, 1H), 4.72 (m, 2H), 5.50 (m, 3H), 5.87 (s, 1H), 5.95 (m, 1H), 6.70 (m, 2H), 7.95 (m, 2H).

EXAMPLE A11

Allyl 6-Bromo-6-[1-hydroxy-2-oxo-2-(4-fluorophenyl)ethyl]-penicillanate (Toluene Solution)

Allyl 6,6-dibromopenicillanate (13.0 g., 0.0326 mol), methylmagnesium bromide (12.34 ml. of 2.9M in ether, 0.0358 mol) and (4-fluorophenyl)glyoxal (4.95 g., 0.0326 mol) were reacted in THF according to the method of Example A1. The reaction was quenched with 4 ml. of acetic acid in 40 ml. THF, warmed to ambient temperature, stripped of THF, diluted with 300 ml. toluene, washed with 200 ml. water, layered with 200 ml. of fresh water and the pH adjusted to 8.0 with dilute NaOH. The organic layer was separated, washed 1×200 ml. brine, dried, and the resulting solution of title product, a mixture of diastereoisomers, utilized directly in the next step; tlc Rf 0.4 (9:1 toluene:ether).

EXAMPLE A12

Allyl 6-Bromo-6-[R- and S-1-hydroxy-2-oxo-2-(4-(propenyloxy)phenyl)ethyl]penicillanate Using 3:2 hexane:ether as eluant, but otherwise by the method of Example A2, allyl 6,6-dibromopenicillanate (5.83 g., 0.015 mol), methylmagnesium bromide (4.48 ml. of 3.1 in ether, 0.015 mol) and freshly distilled [4-propenyloxy)phenyl]glyoxal (2.78 g., 0.015 mol) were converted to instant title products 7.78 g. initially isolated as a mixture of isomers without chromatography; $^1$H-nmr 1.46 and 1.52 (2s, 3H), 1.68 (s, 3H), 1.75 (dd, 3H), 4.45 and 4.61 (2s, 1H), 4.73 (m, 2H), 5.15 (m, 1H), 5.3-5.8 (m, 1H), 5.60 and 5.90 (2s, 1H), 6.0 (m, 1H), 6.51 (m, 1H), 7.15 (m, 2H), 8.1 (m, 2H). On chromatography these were separated into a R-and S-epimers of unspecified C.6 stereochemistry:

S-epimer (lp), 1.01 g.; tlc Rf 0.32 (1:1 hexane:ether);
R-epimer (mp), 1.13 g.; tlc Rf 0.28 (1:1 hexane:ether).

EXAMPLE A13

Allyl 6-Bromo-6-[R-2-(3-thienyl)-2-oxo-1-hydroxyethyl]-penicillanate

Under N$_2$, allyl 6,6-dibromopenicillanate (9.10 g., 0.0228 mol) was dissolved in 100 ml. dry toluene and cooled to −78°. CH$_3$MgBr (7.35 ml. of 3.10M in ether, 0.0228 mol) was added via syringe over 15 minutes, followed after 12 minutes by (3-thienyl)glyoxal (freshly distilled, 3.20 g., 0.0228 mol) in 15 ml. toluene over 10 minutes, while maintaining temperature with an acetone-dry ice bath. After a further 45 minutes at −78°, the reaction was poured into 200 ml. saturated NH$_4$Cl and extracted 3×150 ml. ether. The combined organic layers were washed 2×100 ml. H$_2$O and the 1×200 ml. brine, dried over Na$_2$SO$_4$ and stripped to an oil (11.5 g.). The desired R-epimer of unspecified C.6 stereochemistry was isolated by chromatography on silica gel, monitoring by tlc and eluting with 1:1 hexane:ether, 6 g.; tlc Rf 0.3 (3:2 ether:hexane).

EXAMPLE A14

Allyl 6-Bromo-6-[2-(1-Methyl-2-pyrrolyl)-2-oxo-1-hydroxyethyl]penicillanate

According to the preceding Example, allyl 6,6-dibromopenicillanate (5.90 g., 0.015 mol) and (1-methyl-2-pyrrolyl)glyoxal (2.03 g., 0.015 mol) were reacted to form title product. After reacting 1 hour at −78°, the acetic acid (1.26 ml., 0.023 mol) in 10 ml. THF was added and the mixture warmed to ambient temperature, diluted with equal volumes each of toluene and water, the pH adjusted to 8.5 with dilute NaOH, and the aqueous phase separated and washed with 40 ml. fresh toluene. The organic layers were combined, washed 1×40 ml. brine, dried over Na$_2$SO$_4$ and stripped to yield title product as mixed R- and S-sidechain epimers of unspecified C.6 stereochemistry, tlc Rf 0.8 (11:1 CH$_2$Cl$_2$:ethyl acetate), the entire batch of product being used directly in the next step (Example B17).

EXAMPLE A15

Allyl 6-Bromo-6-[2-(1-benzyl-2-pyrrolyl)-2-oxo-1-hydroxyethyl]penicillanate

By the method of Example A14, allyl 6,6-dibromopenicillanate (12.8 g., 0.0321 mol) and (1-benzyl-2-pyrrolyl)glyoxal (6.84 g., 0.0321 mol) were converted to instant title product, isolated as a solution in 400 ml. of toluene, used directly in the next step (Example B18); tlc Rf 0.85 (9:1 toluene:ethyl acetate).

EXAMPLE A16

Allyl 6-Bromo-6-[2-(2-methoxyphenyl)-1-hydroxy-2-oxoethyl]penicillanate

By the procedure of Example A13, allyl 6,6-dibromopenicillanate (12.2 g., 0.031 mol) and (2-methoxyphenyl)glyoxal (5.00 g., 0.031 mol) were converted, without chromatography, to title product as an isomer mixture, 15.3 g.; oil; tlc Rf 0.16 (3:2 hexane:ethyl acetate).

EXAMPLE A17

Allyl 6-Bromo-6-(1-hydroxy-3,3-dimethyl-2-oxobutyl)-penicillanate

By the method of Example A1, allyl 6,6-dibromopenicillanate (15.96 g., 0.04 mol) and (t-butyl)-glyoxal (4.57 g., 0.04 mol) were reacted to form title product. After 30 minutes at −78°, the mixture was quenched by the rapid addition of CH$_3$COOH (4.56 ml., 0.08 mol), then warmed to 0°, diluted with equal volumes each of toluene and water, the pH adjusted to 7.5, and the organic layer separated, washed 1×200 ml. H₂O and 1×200 ml. brine and dried to yield a solution of title product (a mixture of side chain epimers), all of which was used directly in the next step (Example B20); tlc Rf 0.35 and 0.65 (9:1 toluene:ethyl acetate), Rf 0.65 and 0.95 (9:1 CH₂Cl₂:ethyl acetate).

EXAMPLE A18

Allyl 6-Bromo-6-[1-hydroxy-2-(N-methyl-2-indolyl)-2-oxoethyl]penicillanate

The method of the preceding Example was used to react allyl 6,6-dibromopenicillanate (22.38 g., 0.056 mol) with (N-methyl-2-indolyl)glyoxal (10.5 g., 0.056 mol). After quenching with CH₃COOH and warming to 0°, the mixture was poured into 200 ml. each of H₂O and ethyl acetate, and the pH adjusted to 3.0. The aqueous phase was separated and extracted with fresh ethyl acetate. The organic layers were combined, extracted with 1×200 ml. H₂O, 1×200 ml. H₂O with the pH adjusted to 8.5, 1×200 ml. H₂O and 1×200 ml. brine, dried and stripped to yield title product as an oil, all of which was used in the next step (Example B21).

EXAMPLE A19

Allyl 6-Bromo-6-[1-hydroxy-2-(1-methyl-2-imidazolyl)-2-oxoethyl]penicillanate

By the method of Example A17, allyl 6,6-dibromopenicillanate (0.52 g., 0.0013 mol) and (1-methyl-2-imidazolyl)glyoxal (0.18 g., 0.0013 mol) were converted to a toluene solution of title product; tlc Rf 0.9 (1:1 CH₂Cl₂:ethyl acetate). The entire solution was used in the next step (Example B22).

EXAMPLE A20

Allyl 6-Bromo-6-[2-(2-benzothienyl)-1-hydroxy-2-oxoethyl]penicillanate

By the method of Example A14 allyl 6,6-dibromopenicillanate (8.39 g., 0.021 mol) and (2-benzothienyl)glyoxal (4.0 g., 0.021 mol) were converted to present title product. After about 30 minutes at −78°, the reaction mixture was quenched by pouring into 250 ml. saturated NH₄Cl. The aqueous layer was extracted 3×200 ml. ether. The organic layers were combined, washed 1×200 ml. H₂O and 1×200 ml. brine, dried and stripped to produce title product as 12 g. of oil, still containing toluene, all of which was used directly in the next step (Example B23); tlc Rf 0.32 and 0.41 (2:1 hexane:ethyl acetate), reflecting side chain epimers.

EXAMPLE A21

Allyl 6-Bromo-6-[1-hydroxy-2-oxo-2-(2-phenyl-4-thiazolyl)ethyl]penicillanate

By the methods of the preceding Example, allyl 6,6-dibromopenicillanate (7.35 g., 0.018 mol) and (2-phenyl-4-thiazolyl)glyoxal (4.0 g., 0.018 mol) were converted to present title product, 10.6 g., all of which was used directly in the next step (Example B24); tlc (3:1 hexane) showed three products having Rf values 0.30, 0.24 and 0.18, the heaviest at Rf 0.24.

EXAMPLE A22

Allyl 6-Bromo-6-[1-hydroxy-2-(4-methylphenyl)-2-oxoethyl]penicillanate (4-Methylphenyl)glyoxal hydrate (3.5 g.) was distilled in a Kugelrohr apparatus (105°, 0.75 mm) to yield 2.0 g. (0.0135 mol) of (4-methylphenyl)glyoxal which was immediately dissolved in 25 ml. of toluene and reacted with allyl 6,6-dibromopenicillanate (5.38 g., 0.0135 mol) concurrently converted to the Grignard according to Example A14. After 1.5 hours at −78°, the reaction was quenched and product isolated according to Example A20 to yield crude title product as an oil, tlc Rf 0.27 and 0.32 (4:1 hexane:ethyl acetate), reflecting side chain epimers.

EXAMPLE A23

Allyl 6-Bromo-6-[1-hydroxy-2-(4-methoxycarbonylphenyl)-2-oxoethyl]penicillanate

By the methods of preceding Example [distilling 6 g. of (4-methoxycarbonylphenyl)glyoxal from 7 g. of the hydrate at 115°/1 mm], allyl 6,6-dibromopenicillanate (12 g., 0.03 mol) was converted to present title product, ultimately concentrated to 200 ml. of a toluene solution used directly in the next step (Example B26); tlc showed three products at Rf values 0.43, 0.35 and 0.29 (2:1 hexane:ethyl acetate).

EXAMPLE A24

Allyl 6-Bromo-6-[1-(4-cyanophenyl)-1-hydroxy-2-oxoethyl]penicillanate

By the method of Example A22 [distilling 6 g. of (4-cyanocarbonylphenyl)glyoxal from 7 g. of the hydrate], allyl 6,6-dibromopenicillanate (14.7 g., 0.037 mol) was converted to present title product, isolated as an oil, 15.8 g.; tlc Rf 0.24, 0.30, 0.35 (2:1 hexane:ethyl acetate).

EXAMPLE A25

Allyl 6-Bromo-6-(1-hydroxy-2-oxo-3-methyl-3-phenoxybutyl)penicillanate

By the method of Example A22, freshly distilled (1-benzyloxy-1-methylethyl)glyoxal (1.5 g., 6.9 mmol) and allyl 6,6-dibromopenicillanate (2.75 g., 6.9 mmol) were converted to present title product, 3.0 g.; tlc Rf 0.30, 0.40 and 0.49 (3:1 hexane:ethyl acetate).

EXAMPLE A26

Allyl 6-Bromo-6-[1-hydroxy-2-oxo-3,3-(spirocyclohexyl)-butyl]penicillanic

By the method of the preceding Example, (1-methylcyclohexyl)glyoxal (12 g., 0.03 mol) was converted to present title product, 12 g.; tlc Rf 0.39 and 0.43 (4:1 hexane:ethyl acetate).

EXAMPLE A27

Allyl 6-Bromo-6-[1-hydroxy-2-oxo-2-(1-adamantyl)ethyl]-penicillanate

By the method of Example A28 below, (1-adamantyl)glyoxal (3.0 g., 0.021 mol) was converted to title product as a foam, 10.7 g.; tlc Rf 0.26 (4:1 hexane: ethyl acetate).

EXAMPLE A28

Allyl 6-bromo-6-[1-hydroxy-2-oxo-2-(4-(t-butyl dimethylsiloxymethyl)phenyl)ethyl]penicillanate Allyl 6,6-dibromopenicillanate (10.0 g., 0.025 mol) was dissolved in 200 ml. $CH_2Cl_2$ and cooled to $-78°$. Keeping the temperature below $-70°$, methylmagnesium bromide (8.37 ml. of 3M in ether, 0.025 mol) was added slowly, and the mixture stirred 1 hour at $-75°$. 4-(t-Butyldimethylsiloxymethylphenyl)glyoxal (freshly distilled from 7 g. of hydrate, in 75 ml. $CH_2Cl_2$) was then added slowly and the mixture stirred a further 1.5 hours at $-75°$, poured into an equal volume of saturated $NH_4Cl$. The aqueous layer was separated and extracted $3\times100$ ml. $CH_2Cl_2$. The four organic layers were combined, washed $1\times200$ ml. $H_2O$ and $2\times200$ ml. brine, dried over $MgSO_4$ and stripped to yield title product as an oil, 12.4 g., tlc Rf 0.45 and 0.49 (2:1 hexane:ethyl acetate).

EXAMPLE A29

Allyl 6-Bromo-6-[1-hydroxy-2-oxo-2-(4-(1-hydroxy-1-methylethyl)phenyl)ethyl]penicillanate By the method of the preceding Example [4-(1-hydroxy-1-methylethyl)phenyl]glyoxal (1.0 g., 5.2 mmol) was converted to present title product as an oil, 2.6 g.; tlc Rf 0.26, 0.30 (1:1 hexane:ethyl acetate).

EXAMPLE A30

Allyl 6-Bromo-6-[1-hydroxy-2-oxo-2-(4-(chloromethyl)-phenyl)ethyl]penicillanate

By the method of Example A28, [4-(chloromethyl)-phenyl]glyoxal (4.0 g., 0.022 mol) was converted to present title product, initially as an oil, 9.7 g., which was chromatographed on silica gel using 7:4 hexane:ethyl acetate as eluant to yield three isomers as follows: 0.49 g., tlc Rf 0.51 (1:1 hexane:ethyl acetate); 0.61 g., tlc Rf 0.42 (1:1 hexane:ethyl acetate); and 0.64 g., tlc Rf 0.37 (1:1 hexane:ethyl acetate), the least polar isomer having S-sidechain stereochemistry and the two more polar isomers having the preferred R-sidechain stereochemistry, one the 6-alpha-bromo isomer and the other the 6-beta-bromo isomer.

EXAMPLE A31

Allyl 6-Bromo-6-[1-hydroxy-2-(N-methyl-3-indolyl)-2-oxoethyl]penicillanate

By the method of Example A18, (N-methyl-3-indolyl)glyoxal (8.0 g., 0.043 mol) was converted to title product, isolated as an oil in like manner, all of which was used in the next step (Example B34); tlc Rf 0.05, 0.15 (9:1 toluene:ethyl acetate).

EXAMPLE A32

Allyl 6-Bromo-6-[3-(benzyloxycarbonylamino)-1-hydroxy-3-methyl-2-oxobutyl]penicillanate By the method of Example A8, [1-(benzyloxycarbonylamino)-1-methylethyl]glyoxal (4.41 g., 0.018 mol) was converted to present title product isolated as an oil, 9.48 g.; tlc Rf 0.42 (2:3 ethyl acetate: hexane).

EXAMPLE A33

Allyl 6-Bromo-6-[1-hydroxy-2-oxo-2-(4-(benzyloxycarbonylamino)phenyl)ethyl]penicillanate By the method of Example A13, except to use 1:19 acetone:CHCl3 as eluant on chromatography, [4-(benzyloxycarbonylamino)phenyl]glyoxal (5.0 g., 0.0176 mol) was converted to title product, isolated as a mixture of isomers, 3.43 g.; tlc Rf 0.28, 0.35 (1:19 acetone: $CHCl_3$).

EXAMPLE A34

Allyl 6-Bromo-6-[1-hydroxy-2-oxo-2-(2-ethoxy-1-naphthyl)ethyl]penicillanate

By the method of Example A8, (2-ethoxy-1-naphthyl)glyoxal (4.50 g., 1.97 mmol) was converted to present title product as a thick oil, 11.02 g.; tlc Rf 0.35, 0.50 (2:1 hexane:ethyl acetate); all of which was used in the next step (Example B37).

EXAMPLE A35

Allyl 6-Bromo-6-[1-hydroxy-2-oxo-(3-hydroxyphenyl)ethyl]-penicillanate

By the method of Example A2, using 1:1 hexane: ethyl acetate as eluant, (3-hydroxyphenyl)glyoxal (3.0 g., 0.019 mol) was converted to chromatographed title product, 0.59 g.; $^1$H-nmr 1.35 (s, 3H), 1.52 (s, 3H), 4.50 (m, 3H), 5.20 (m, 3H), 5.44 (m, 2H), 5.71 (m, 1H), 6.95 (d, 1H, J=4Hz), 7.13 (t, 1H, J=4Hz), 7.28 (m, 2H), 7.63 (br s, 1H).

EXAMPLE A36

Allyl 6-Bromo-6-[R-1-Hydroxy-2-oxo-2-(3-quinolyl)ethyl]-penicillanate

By the method of Example A8, chromatographing the crude product using 1:1 hexane:ethyl acetate as eluant, (3-quinolyl)glyoxal (freshly dehydrated from 1.4 g. of the hydrate solubilized in toluene by the addition of one-half volume of THF) was converted to present title product, 0.25 g.; tlc Rf 0.3 (1:1 hexane:ethyl acetate).

EXAMPLE A37

Allyl 6-Bromo-6-[R-1-Hydroxy-2-oxo-2-(4-hydroxyphenyl)ethyl]penicillanate

By the method of the preceding Example, using 2:1 hexane:ethyl acetate as eluant on chromatography, (4-hydroxyphenyl)glyoxal (0.22 g. freshly distilled from 1.5 g. of the hydrate) was converted to present title product, 0.16 g.; tlc Rf (1:1 hexane:ethyl acetate); $^1$H-nmr 1.49 (s, 3H), 1.64 (s, 3H), 4.54 (s, 1H), 4.72 (m, 1H), 5.40 (m, 4H), 5.59 (s, 1H), 5.81 (s, 1H), 5.92 (m, 1H), 6.87 (d, 2H, J=6Hz), 7.87 (d, 2H, J=6Hz).

EXAMPLE A38

Allyl 6-Bromo-6-[R-1-Hydroxy-2-oxo-2-(2-naphthyl)ethyl]-penicillanate

By the method of Example A8, (2-naphthyl)glyoxal (3.3 g., 0.02 mol) was converted to crude title product, 11.6 g., which was chromatographed on silica gel to yield a mixture of 6-alpha-bromo and 6-betabromo isomers have R-side chain stereochemistry, 2.11 g.; tlc Rf 0.37, 0.42 (2:1 hexane:ethyl acetate).

METHOD B—DEBROMINATION

EXAMPLE B1

Allyl 6-beta-[R- and S-1-Hydroxy-2-oxo-2-(phenyl)ethyl]penicillanate

Title product of Example A1 (6.0 g., 0.0132 mol) in 100 ml. of benzene was dried and filtered into a flask. Under $N_2$, tributyltin hydride (3.6 ml. 0.0132 mol) was added and the mixture heated to reflux for 1.75 hours, monitoring by tlc. More of the hydride (1.8 ml., 0.0066 mol) was added and reflux continued an additional hour, by which time tlc indicated some starting material still present. AIBN (10 mg.) was then added and reflux continued 1 hour. The mixture was cooled and stripped, the residue taken up in 100 ml. $CH_3CN$ and washed 3×100 ml. hexane, and the $CH_3CN$ stripped to yield a crude mixture of the title products as an oil (6.0 g.). Title products were separated and purified by chromatography on 600 g. fine mesh silica gel, eluting with 1:1 ether:hexane. The more polar (mp) component is the S-epimer, and the less polar the R-epimer.

S-epimer (mp); 1.29 g.; tlc Rf 0.3 (1:1 ethyl acetate:hexane); $^1$H-nmr 1.46 (s, 3H), 1.68 (s, 3H), 3.90 (b, s, 1H), 4.03 (dd, 1H, J=4.8, 9Hz), 4.48 (s,1H), 4.65 (d, 1H, J=9Hz), 5.27–5.47 (m, 2H), 5.57 (d, 1H, J=4.8Hz), 5.94 (m, 1H), 7.45–8.04 (m, 5H, Ar); ir (CHCl$_3$) cm$^1$: 3551 (b), 2965 (m), 1769 (s), 1759 (s), 1690 (s), 1601 (m), 1450 (m), 1270 (s), 980 (m); exact mass: calculated 375.1141; found, 375.1115; the stereochemistry of the S-epimer was proven by X-ray crystallographic analysis.

R-epimer (lp); 0.74 g.; tlc Rf 0.2 (1:1 ethyl acetate:hexane); $^1$H-nmr 1.47 (s, 3H), 1.70 (s, 3H), 3.98 (dd,1H, J=4.5, 6.2Hz), 4.23 (s, 1H), 4.63 (d, 1H, J=6.2Hz), 5.23–5.44 (m, 3H), 5.98 (m, 1H), 7.30–8.01 (m, 5H); ir (CHCl$_3$) cm$^{-1}$ 3472 (b), 2968 (m), 1785 (s), 1749 (s), 1689 (s), 1602 (m), 1450 (m), 1274 (s), 985 (m); exact mass: calculated, 375.1141; found, 375.1149.

A center-cut (0.64 g.) consisting of a mixture of these two isomers, suitable for recycling, was also obtained from the present chromatography.

EXAMPLE B2

Benzyl 6-beta-[R- and S-1-Hydroxy-2-oxo-2-(phenyl)ethyl]penicillanate

By the method of the preceding Example, except to use 2:1 hexane:ethyl acetate in silica gel chromatography, title product of Example A2 (0.65 g., 0.0013 mol) was converted to present title products, resulting in less polar R-epimer, 60 mg., tlc Rf 0.35 (2:1 hexane:ethyl acetate); mixed epimers, 200 mg.; and more polar S-epimer, 160 mg., tlc Rf 0.25 (2:1 hexane:ethyl acetate). The R-epimer showed $^1$H-nmr 1.35 (s, 3H), 1.68 (s, 3H), 3.97 (m, 2H), 4.48 (s, 1H), 5.15 (s, 2H), 5.45 (d, 1H, J=4.5Hz), 5.55 (dd, 1H, J=6, 9.5Hz), 7.25–8.10 (m, 10H).

EXAMPLE B3

Allyl 6-beta-(S-1-Hydroxy-2-oxo-propyl)penicillanate

Less polar (R) title product of Example A3 (0.18 g., 0.00046 mol) was dissolved in 3 ml. benzene, dried and filtered into a flask. Tributyltin hydride (0.14 ml., 0.00052 mol) was added and the mixture refluxed 1.5 hours, cooled, stripped to an oil and chromatographed on fine mesh silica gel to yield title product, 43 mg.; tlc Rf 0.4 (1:1 ethyl acetate:hexane); $^1$H-nmr 1.50 (s, 3H), 1.71 (s, 3H), 2.32 (s, 3H), 3.82 (dd, 1H, J=4.5, 8.5Hz), 4.50 (s, 1H), 5.35 (m, 2H), 5.56 (d, 1H, J=4.5Hz), 5.92 (m, 1H); ir (CHCl$_3$) cm$^{-1}$: 3495 (b), 2985 (w), 1775 (s), 1750 (s), 1730 (s), 1370 (m), 1270 (m), 1155 (m), 980 (m).

EXAMPLE B4

Allyl 6-beta-(R-1-Hydroxy-2-oxopropyl)penicillanate

More polar (S) title product of Example A3 (700 mg., 0.0018 ml.) in 25 ml. benzene was treated with tributyltin hydride (0.53 ml. 0.0020 mol), refluxed 3.5 hours, treated with additional hydride (0.3 ml.) and AIBN (5 mg.), refluxed for an additional 3 hours, cooled and stripped. The residue was chromatographed on fine mesh silica gel with 3:1 hexane:ethyl acetate as eluant to yield purified title product, 160 mg.; tlc Rf 0.75 (1:1 ethyl acetate:hexane); $^1$H-nmr 1.52 (s, 3H), 1.74 (s, 3H), 2.46 (s, 2H), 3.66 (m, 2H), 4.49 (s, 1H), 4.60 (dd, 1H, J=6.0, 10.0Hz), 4.7 (m, 2H), 5.38 (m, 2H), 5.46 (d, 1H, J=4.5Hz), 5.92 (m, 1H); ir (CHCl$_3$) cm 3450 (b), 2950 (w,) 1785 (s), 1755 (s), 1730 (s), 1380 (m), 1310 (m), 1160 (m).

EXAMPLE B5

Allyl 6-beta-[R- and S-1-Hydroxy-2-oxo-2-(2-furyl)ethyl]penicillanate

Title product of Example A4 (1.3 g., 0.0030 mol) in 30 ml. benzene was treated with tributyltin hydride (1.58 ml., 1.71 g., 0.0059 mol). After refluxing 2 hours, a like quantity of tributyltin hydride and 5 mg. AIBN were added and refluxing continued 5 hours more. The reaction mixture was evaporated, taken into 10 ml. acetonitrile, washed 3×5 ml. hexane, reevaporated and flash chromatographed using 2:1 hexane:ethyl acetate as eluant to yield title products:

R-epimer (mp), 220 mg.; tlc Rf 0.5 (1:1 ethyl acetate:hexane); $^1$H-nmr 1 43 (s, 3H), 1.73 (s, 3H), 4.01 (m, 2H), 4.45 (s, 1H), 4.63 (m, 2H), 5.27 (m, 2H), 5.45 (d, 1H), 5.92 (m, 1H), 6.58 (m, 1H), 7.41 (m, 1H), 7.62 (m, 1H); ir (CHCl$_3$) cm$^{-1}$: 3495 (b); 2980 (w), 1790 (s), 1755 (s), 1580 (w), 1470 (m), 1480 (m), 1305 (s), 155 (m), 1090 (m), 1020 (m), 990 (m).

Mixed epimers, 90 mg.

S-epimer (mp) 420 mg.; tlc Rf 0.4 (1:1 ethyl acetate:hexane); $^1$H-nmr 1.42 (s, 3H), 1.61 (s, 3H), 3.82 (b, 1H), 4.01 (dd, 1H), 4.46 (s, 1H), 4.65 (m, H), 5.27 (m, 2H), 5.53 (d, 1H), 5.91 (m, 1H), 6.53 (m, H), 7.45 (m, 1H), 7.60 (m, 1H),; ir (CHCl$_3$) cm$^{-1}$: 500 (b), 2980 (w), 1780 (s), 1755 (s), 1685 (s), 1625 (m), 1580 (w); 1470 (m), 1295 (m), 1160 (m), 1020 (m), 990 (m).

EXAMPLE B6

Allyl 6-beta-[R- and S-1-Hydroxy-2-oxo-2-(4-methoxyphenyl)ethyl]penicillanate

Title product of Example A5 (1.57 g., 0.00324 mol) in 30 ml. benzene was refluxed with tributyltin hydride (1.414 ml., 0.0049 mol) for 4 hours. The reaction mixture was cooled, diluted with acetonitrile (50 ml.), extracted 4 35 ml. hexane and evaporated to an oil (1.21 g.) which was chromatographed according to the preceding Example to yield title products as follows:

S-epimer (mp), 221 mg.; tlc Rf 0.2 (2:1 hexane:ethyl acetate); $^1$H-nmr: 1.46 (s, 3H), 1.69 (s, 3H), 3.48 (s, b, 1H), 3.90 (s, 3H), 4.40 {dd, 1H), 4.48 (s, 1H), 4.68 (m, 2H), 5.35 (m, 2H), 5.58 (d, 1H), 5.92 (m, 1H), 6.98 (d, 2H), 8.03 (d, 2H).

R-epimer (lp), 124 mg.; tlc Rf 0.15 (2:1 hexane:ethyl acetate); $^1$H-nmr 1.50 (s, 3H), 1.75 (s, 3H), 3.88 (s, 3H), 3.92 (m, 2H), 4.48 (s, 1H), 4.65 (m, 2H), 5.40 (m, 2H), 5.42 (d, 1H), 5.92 (m, 1H), 6.98 (d, 2H), 8.01 (d, 2H).

This procedure was repeated on 1.5 g. of title product of Example A4, except to use 1:1 ether:hexane as eluant on chromatography, to yield 248 mg. of lp R-epimer and 329 mg. of mp S-epimer.

EXAMPLE B7

6-beta-[S-1-Hydroxy-2-oxo-2-(2-thienyl)ethyl]penicillanate

By the procedure of Example B5, the R-epimer of Example A6 (2.8 g.) was converted to chromatographed title product, initially as an oil (600 mg.) which crystallized by scratching with ether, 202 mg.; tlc Rf 0.7 (1:1 ethyl acetate:hexane); ir (CHCl$_3$) cm$^{-1}$: 3530 (b), 2985 (w), 1780 (s), 1755 (s), 1670 (s), 1410 (m), $^1$H-nmr 1.48 (s, 3H), 1.67 (s, 3H), 3.55 (s, 1H), 4.03 (dd, 1H), 4.49 (s, 1H), 4.65 (m, H), 5.30 (m, 3H), 5.58 (d, 1H), 5.91 (m, 1H), 7.18 (dd, 1H), 7.74 (m, 1H), 8.09 (dd, 1H).

EXAMPLE B8

Allyl 6-beta-[R-1-Hydroxy-2-oxo-2-(2-thienyl)ethyl]penicillanate

By the procedure of Example B5, the S-epimer of Example A6 (1.2 g.) was converted to chromatographed title product as an oil, 0.37 g.; tlc Rf 0.6 (1:1 ethyl acetate:hexane); ir (CHCl$_3$) cm (s), 1755 (s), 1670 (s), 1410 (m), 1310 (m), 1270 H-nmr 1.51 (s, 3H), 1.74 (s, 3H), 3.97 (dd, 1H), 4.04 (d, 1H), 4.48 (s, 1H), 4.66 (m, 2H), 5.35 (m, 2H), 5.50 (d, 1H), 5.90 (m, 1H), 7.19 (dd, 1H), 7.74 (m, H), 7.92 (dd, 1H).

EXAMPLE B9 Allyl 6-beta-[R- and S-1-Hydroxy-2-oxo-2-(1-naphthyl)ethyl]penicillanate By the method of Example B4, using 2:5 hexane:ethyl acetate as eluant, title product of Example A7 (5.30 g., 0.011 mol) was converted to title products, yielding:

Mixed title isomers, 1.17 g., suitable for further chromatographic separation; tlc Rf 0.18 and 0.25 (2:5 hexane:ethyl acetate);

Pure title S-epimer (the more polar, Rf 0.18), 0.63 g.; $^1$H-nmr 1 45 (s, 3H), 1.69 (s, 3H), 3.90 (s, b, 1H, OH), 4.04 (dd, 1H), 4.55 (s, 1H), 4.70 (m, 2H), 4.50 (m, 4H), 5.95 (m, 1H), 7.5-8.6 (m, 7H, Ar); ir (CHCl$_3$) cm$^{-1}$: 3480 (b), 2980 (w), 17 1685 (s), 1495 (m), 1210 (s), 1050 (m), 950 (m).

EXAMPLE B10

Allyl 6-beta-[S-2-(R- and S-1-(Ethoxy)ethoxy)-1-hydroxy-3-(phenyl)prop-2enyl]penicillanate Title product of Example A8 (5.95 g., 0.011 mole), tributyltin hydride (4.4 ml., 4.8 g., 0.0165 mol) and AIBN (20 mg.) were combined in 80 ml. benzene and refluxed 18 hours. The mixture was cooled, diluted with 200 ml. hexane and 200 ml. acetonitrile and the layers separated. The acetonitrile layer was washed 4×100 ml. fresh hexane and stripped to an oil (4.77 g.) which was chromatographed on 475 g. silica gel with 1:1 hexane:ether as eluant to yield a mixture of title products, 800 mg. These isomers were unnecessarily separated on 80 g. of fresh silica gel using 1:3 acetone:CHCl$_3$ as eluant to yield separated title products, each of unspecified stereochemistry in the 1-(ethoxy)ethoxy sidechain:

lp epimer, 0.22 g.; $^1$H-nmr 1.15 (t, 3H), 1.38 (d, 3H), 1.44 (s, 3H), 1.69 (s, 3H), 3.6 (m, 2H), 4.14 (m, 3H), 4.50 (s, 1H), 4.70 (d, 2H), 5.05 (q, 1H), 5.44 (m, 3H), 5.94 (m, 1H), 6.12 (s, 1H), 7.36 (m, 3H), 7.59 (m, 2H).

mp epimer, 0.16 g.; $^1$H-nmr 1 14 (t, 3H), 1.45 (s, 3H), 1.69 (s, 3H), 3.63 (m, 3H), 4.07 (m, 2H), 4.50 (s, 1H), 4.70 (m, 3H), 5.42 (m, 3H), 5.92 (m, 1H), 6.02 (s, 1H), 7.36 (m, 3H), 7.69 (m, 2H).

EXAMPLE B11

Allyl 6-beta-[S-2-(1-(Ethoxy)ethoxy)-1-hydroxy-3-(2-thienyl)prop-2-enyl]penicillanate By the method of the preceding Example, title product of Example A9 (3.1 g., 0.0057 mol) was converted to present chromatographed title product as an oil, 0.77 g., a mixture of 1-(ethoxy)ethoxy sidechain epimers; tlc Rfs 0.15 and 0.2 (1:1 ether;Hexane); $^1$H-nmr 1.23 (t, 3H), 1.44 (s, 3H), 1.46 (d, 3H), 1.70 (s, 3H), 3.91 (m, 3H), 4.09 (dd, 1H), 4.50 (s, 1H), 4.73 (m, 3H), 5.49 (m, 4H), 6.01 (m, 1H), 6.34 (s, 1H), 7.06 (m, 2H), 7.34 (m, 1H).

EXAMPLE B12

Allyl 6-beta-[R- and S-1-Hydroxy-2-oxo-2-(4-dimethylamnopheny)ethyl]penicillanate Using a reaction time of 6 hours at reflux and 48 hours at ambient temperature, and 1:1 ether:hexane as eluant, the method of Example B10 was employed to convert title product of Example A10 (2.15 g., 0.0040 mol) to present title products:

R-epimer (lp), 396 mg.; $^1$H-nmr 1.50 (s, 3H), 1.78 (s, 3H), 3.10 (s, 6H), 3.90 (dd, 1H), 4.02 (d, 1H), 4.45 (s, 1H), 4.64 (m, 2H), 5.41 (m, 4H), 5.90 (m, 1H), 6.68 (d, 2H), 7.90 (d, 2H); ir (KBr) cm$^{-1}$: 3485 (b), 2980 (m), 1760 (s), 1665 (s), 1615 (s), 1380 (s), 1300 (s), 1190 (s).

S-epimer (mp), 570 mg.; 1.46 (s, 3H), 1.70 (s, 3H), 3.07 (s, 6H), 3.56 (d, 1H), 4.01 (dd, 1H), 4.48 (s, 1H), 4.64 (d, 2H), 5.35 (m, 3H); 5.52 (d, 1H), 5.91 (m, 1H), 6.66 (d, 2H), 7.91 (d, 2H); (KBr) cm$^{-1}$ 3481 (b), 2975 (w), 2930 (w), 1775 (s), 1743 (s), 1649 (m), 1605 (s), 1288 (s), 1193 (s).

EXAMPLE B13

Allyl 6-beta-R-[R- and S-1-Hydroxy-2-oxo-2-(4-fluorophenyl)ethyl]penicillanate To the entire product (toluene solution) of Example A11 (0.0326 mol, assuming quantitative conversion) was treated with tributyltin hydride (12 ml., 0.037 mol) and the mixture stirred for 60 hours, then refluxed 2 hours. The reaction mixture was cooled, stripped of solvent and the residue flash chromatographed on silica gel initially with $CH_2Cl_2$ to remove tin derivatives and then with 8:1 $CH_2Cl_2$:ethyl acetate. The latter eluant was stripped to yield 9.19 g. crude product which was chromatographed on 650 g. silica gel, using 9:1 toluene-:ethyl acetate as eluant, to yield a mixture of title epimers (containing the 1p R-epimer as a major component) 1.94 g. and pure s-epimora (mp), 2.16 g.; $^1$H-nmr 1.46 (s, 3H), 1.68 (s, 3H), 3.49 (bd, IH), 4.06 (dd, J=4 and 9.1, 1H), 4.47 (s, 1H), 4.66 (d, 2H), 5.35 (m, 3H), 5.58 (d, J=4, 1H), 5.92 (m, IH), 7.16 (m, 2H), 8.11 (m, 2H).

The mixed epimers were twice chromatographed, once with 3:2 ether:toluene as eluant, once with 10:2 toluene:ethyl acetate as eluant to yield purified r-epimer (lp), 0.7 g.; $^1$H-nmr 1.49 (s, 3H), 1.74 (s, 3H), 3.94 (m, 1H), 4.46 (s, 1H), 4.64 (m, 2H), 5.34 (m, 2H), 5.48 (d, 1H), 5.91 (m, 1H), 7.18 (m, 2H), 8.05 (m, 2H).

EXAMPLE B14

Allyl 6-beta-[S-1-Hydroxy-2-oxo-2-(4-(propenyloxy)phenyl)ethyl]penicillanate Using a reflux time of 18 hours and 3:2 ether: hexane as eluant the more polar R-epimeric title product of Example A12 (1.13 g., 0.0022 mol) was converted to instant title product, 473 mg.; tlc Rf 0.25 (3:2 ether:hexane); $^1$H-nmr 1.49 (s, 3H), 1.70 (s, H), 1.74 (dd, 3H), 3.41 (d, 1H, OH), 4.03 (dd, 1H), 4.50 (s, 1H), 4.68 (m, 2H), 5.05 (m, 1H), 5.35 (m, 3H), 5.58 (d, 1H), 5.92 (m, 1H), 6.45 (m, 1H), 7.06 (d, 2H), 8.05 (d, 2H); ir ($CHCl_3$) $cm^{-1}$: 3498 (b), 2940 (m), 1770 (s), 1680 (s), 1600 (s), 1250 (s), 980 (s).

EXAMPLE B15

Allyl 6-beta-[R-1-Hydroxy-2-oxo-(4-(propenyloxy)phenyl)ethyl]penicillanate

Using a reflux time of 18 hours, less polar S-epimeric title product of Example A12 (1.01 g., 0.0020 mol) was converted to instant chromatographed title product, 297 mg.; tlc Rf 0.33 (3:2 ether:hexane); $^1$H-nmr 1 51 (s, 3H), 1.72 (dd, 3H), 1.75 (s, 3H), 3.92 (dd, 1H), 3.97 (d, 1H), 4.47 (s, 1H), 4.65 (m, 2H), 5.07 (m, 1H), 5.40 (m, 3H), 5.43 (d, 1H), 5.91 (m, 1H), 6.45 (m, 1H), 7.08 (d, 2H), 8.02 (d, 2H); ir ($CHCl_3$) $cm^{-1}$ 3485 (b), 2940 (m), 1785 (s), 1755 (s), 1605 (s), 1260 (s), 1170 (s), 980 (s).

EXAMPLE B16

Allyl 6-beta-[S-2-(3-thienyl)-2-oxo-1-hydroxyethyl]penicillanate

Title product of Example A13 (6.0 g., 0.013 mol) in 100 ml. benzene was treated with tributyltin hydride (10.5 ml. 11.4 g., 0.039 mol) and refluxed 8 hours, at which time tlc (2:1 hexane:ethyl acetate) indicated heavy product (Rf 0.26) and medium-light starting material (Rf 0.35). Additional tributyltin hydride (1.5 ml.) and about 10 mg. of AIBN were added and the mixture refluxed an additional 2 hours by which time tlc indicated no starting material. The reaction mixture was stripped, taken up in 250 ml. $CH_3CN$, washed 3×100 ml. hexane, restripped to an oil and crystallized by stirring the residue with ether, 1.50 g.; mp 94°–96°; $^1$H-nmr ($CDCl_3$) delta (300 MHz): 1.5 (s, 3H), 1.7 (s, 3H), 3.5 (d, 1H), 4.0 (q, 1H), 4.5 (s, 1H), 4.7 (d, 2H), 5.3 (q, 1H), 5.3–5.45 (dd, 2H), 5.6 (d, 2H), 5.9–6.0 (multiplet, 1H), 7.4 (q, 1H), 7.7 (d, 1H), 8.5 (d, 1H).

EXAMPLE B17

Allyl 6-beta-[R- and S-2-(1-Methyl-2-pyrrolyl)-2-oxo-1-hydroxyethyl]penicillanate The entire batch of product of Example A14 (0.015 mol assumed) was reacted with tributyltin hydride (5.17 ml., 0.019 mol) in 100 ml. toluene for 3.5 days. The solvent was stripped and the residue chromatographed on 600 g. silica gel, initially using $CH_2Cl_2$ and then 11:1 $CH_2Cl_2$:ethyl acetate as eluant, separating title R- and S-epimers as follows:

R-epimer (less polar), 1.21 g.; tlc Rf 0.55 (11:1 $CH_2Cl_2$:ethyl acetate); $^1$H-nmr ($CDCl_3$) delta: 1.49 (s, 3H), 1.74 (s, 3H), 3.92 (dd, 1H, J=4 Hz, 7 Hz), 3.97 (s, 3H), 4.46 (s, 1H), 4.65 (m, 2H), 5.34 (m, 3H), 5.44 (d, 1H, J=7 Hz), 5.92 (m, 1H), 6.19 (m, 1H), 6.94 (br s, 1H), 7.08 (m, 1H).

S-epimer (more polar), 1.15 g.; tlc Rf 0.35 (11:1 $CH_2Cl_2$:ethyl acetate); $^1$H-nmr ($CDCl_3$) delta: 1.47 (s, 3H), 1.70 (s, 3H), 3.95 (s, 3H), 4.03 (dd, 1H, J=4 Hz, 8 Hz), 4.47 (s, 1H), 4.65 (m, 2H), 5.19 (d, 1H, J=8 Hz), 5.34 (m, 2H), 5.50 (d, 1H, J=4 Hz), 5.93 (m, 1H), 6.19 (m, 1H), 6.90 (m, 1H), 7.16 (m, 1H).

EXAMPLE B18

Allyl 6-beta-[R- and S-2-(1-Benzyl-2-pyrrolyl)-2-oxo-1-hydroxyethyl]penicillanate To the entire product of Example A15 in 400 ml. of toluene was added tributyltin hydride (10 ml.). After stirring overnight, additional hydride (1 ml.) was added and the mixture refluxed 2 hours, cooled, stripped and triturated with pentane to yield 12.5 g. of crude product. The pentane triturate was stripped and chromatographed on silica gel, eluting tributyl tin residues with $CH_2Cl_2$ and then an additional 3.0 g. crude product with 10:1 $CH_2Cl_2$ ethyl acetate. The combined crude products (15.5 g.) were chromatographed on silica gel. A less polar impurity and then R-title product were eluted with 8:1 toluene:ethyl acetate, 2.11 g.; tlc Rf 0.35 (9:1 toluene:ethyl acetate); $^1$H-nmr 1.44 (s, 3H), 1.71 (s, 3H), 3.76 (m, 1H), 4.42 (s, 1H), 4.64 (m, 2H), 5.08 (d, 1H), 5.36 (m, 3H), 5.62 (ABq, 2H), 5.92 (m, 1H), 6.27 (m, 1H), 7.16 (m, 7H); followed by the more polar S- title product, eluted with 7:1 toluene:ethyl acetate, 2.68 g.; tlc Rf 0.2 (9:1 toluene:ethyl acetate); $^1$H-nmr ($CDCl_3$) delta: 1.45 (s, 3H), 1.68 (s, 3H), 3.83 (dd, 1H, J=4.3, 7.5 Hz), 4.45 (s, 1H), 4.64 (m, 2H, J=7.5 Hz), 5.18 (d, 1H), 5.27 (d, 1H, J=4.3 Hz), 5.56 (Abq, 2H, J=14.6 Hz), 5.93 (m, 1H), 6.26 (m, 1H), 7.17 (m, 7H).

EXAMPLE B19

Allyl 6-beta-[R- and S-2-(2-Methoxyphenyl)-1-hydroxy-2-oxoethyl]penicillanate

The entire product of Example A16 (0.031 mol assumed), tributyltin hydride (24.6 ml., 26.6 g., 0.092 mol) and about 100 mg. of AIBN were combined in 225 ml. benzene, refluxed 16 hours, stripped to an oil, diluted with 500 ml. $CH_3CN$, washed 4×200 ml. hexane, restripped to an oil and chromatographed on silica gel (8 cm. diameter×30 cm. depth) with 3:1 ether:hexane as eluant collecting 75 ml. fractions. Fractions 21–27 were combined and stripped to yield R-title product as a gelatenous oil, 1.23 g.; $^1$H-nmr 1.5 (s, 3H), 1.75 (s, 3H), 4.0 (s, 3H), 4.0–4.1 (q, 1H), 4.5 (s, 1H), 4.7 (dd, 2H), 5.3–5.4 (m, 3H), 5.6 (d, 1H), 5.9–6.0 (m, 1H), 7.1 (d, 1H), 7.15 (t, 1H), 7.6 (t, 1H), 7.9 (dd, 1H); tlc Rf 0.26 (3:1 ether:hexane). Fractions 31–42 were combined and stripped to yield S-title product as a gelatenous solid, 3.50 g.; $^1$H-nmr 1.5 (s, 3H), 1.7 (s, 3H), 3.95 (s, 3H), 4.0–4.5 (m, 1H), 4.45 (s, 1H), 4.65 (d, 2H), 5.65 (t, 1H), 5.85–5.95 (m, 1H), 7.0 (d, 1H), 7.1 (t, 1H), 7.6 (t, 1H), 7.8 (dd, 1H); tlc Rf 0.14 (3:1 ether:hexane).

EXAMPLE B20

Allyl 6-beta-R- and S-(1-Hydroxy-3,3-dimethyl-2-oxo-butyl)penicillanate

The entire batch of title product of Example A17 (0.04 mol assumed) as a toluene solution was stirred as tributyltin hydride (20 ml., 0.074 mol) was added. After stirring 16 hours, the mixture was refluxed for 5 hours, then cooled, stripped, the residue taken up in 20 ml. $CHCl_3$ and chromatographed on 1 kg. silica gel using 9:1 $CH_2Cl_2$:ethyl acetate as eluant, monitoring by tlc to recover 2.61 g. of less polar (R) epimer of title product, 2.61 g.; tlc Rf 0.3 (9:1 toluene:ethyl acetate, 0.6 (9:1 $CH_2Cl_2$:ethyl acetate); $^1$H-nmr 1.22 (d, 9H), 1.49 (s, 3H), 1.70 (s, 3H), 3.55 (d, 1H, J=10.6), 3.89 (dd, 1H, J=6.28, 4.48), 4.46 (s, 1H), 4.65 (m, 2H), 5.01 (dd, 1H, J=10.6, 6.28), 5.34 (m, 2H), 5.48 (d, 1H, J=4.48), 5.92 (m, 1H); and 2.84 g. of more polar (S) epimer of title product; tlc Rf 0.2 (9:1 toluene:ethyl acetate), 0.5 (9:1 $CH_2Cl_2$:ethyl acetate); $^1$H-nmr 1.25 (s, 9H), 1.46 (s, 3H), 1.66 (s, 3H), 3.89 (dd, 1H, J=9.33, 4.45), 4.43 (s, 1H), 4.66 (m, 2H), 4.98 (d, 1H, J=9.33), 5.34 (m, 2H), 5.49 (d, 1H, J=4.45), 5.92 (m, 1H).

EXAMPLE B21

Allyl 6-beta-[R- and S-1-Hydroxy-2-(N-methyl-2-indolyl-2-oxoethyl]penicillanate

Except to use a reaction time of 1 hour at reflux, the entire batch of title product of Example A18 (0.056 mol assumed) was debrominated and purified according to the preceding Example to yield a less polar fraction containing R-title product contaminated with a slightly, but even less polar impurity, and preferred more polar, S-title product, 5.54 g.; tlc Rf 0.25 (9:1 toluene:ethyl acetate); $^1$H-nmr (250 MHz), 1.47 (s, 3H), 1.70 (s, 3H), 3.58 (br s, 1H), 4.06 (s, 3H), 4.09 (dd, 1H), 4.49 (s, 1H), 4.69 (m, 2H), 5.29 (m, 3H), 5.54 (d, 1H), 5.89 (m, 1H), 7.46 (m, 5H). The less polar fraction was rechromatographed using 9:1 toluene:ethyl acetate as eluant to yield purified, less polar title product, 1.25 g.; tlc Rf 0.35 (9:1 toluene:ethyl acetate); $^1$H-nmr (250 MHz) 1.50 (s, 3H), 1.76 (s, 3H), 3.88 (d, 1H), 4.05 (dd, 1H), 4.08 (s, 3H), 4.47 (s, 1H), 4.63 (m, 2H), 5.42 (m, 2H), 5.47 (d, 1H), 5.92 (m, 1H), 7.45 (m, 5H).

EXAMPLE B22

Allyl 6-beta-[S-1-Hydroxy-2-(1-methyl-2-imidazolyl)-oxoethyl]penicillanate

By the method of Example B20, using a reaction time of 1 hour at 100°, 4:3 $CH_2Cl_2$:ethyl acetate as eluant in chromatography, and recovering only the more polar product fraction, the entire batch of toluene solution product of Example A19 (0.0013 mol assumed) was converted to present title product, 39 mg.; tlc Rf 0.5 (1:1 $CH_2CL_2$:ethyl acetate); $^1$H-nmr (300 MHz) 1.49 (s, 3H), 1.66 (s, 3H), 3.99 (s, 3H), 4.03 (dd, 1H, J=4.8, 9.0), 4.50 (s, 1H), 4.63 (m, 2H), 5.31 (m, 3H), 5.61 (d, 1H, J=4.8), 5.90 (m, 1H), 7.07 (s, 1H), 7.15 (s, 1H).

EXAMPLE B23

Allyl 6-beta-[S-2-(2-Benzothienyl)-1-hydroxy-2-oxoethyl]-penicillanate

By the method of Example B1, using 3:1 hexane:ethyl acetate as eluant on chromatography and recovering only the more polar product fraction, the entire toluene containing product of Example A20 (0.021 mol presumed) as converted to present title product, 0.92 g.; tlc Rf 0.12 (3:1 hexane:ethyl acetate); $^1$H-nmr (300 MHz) 1.45 (s, 3H), 1.7 (s, 3H), 3.65 (br s, 1H), 4.1 (q, 1H), 4.5 (s, 1H), 4.65 (d, 2H), 5.3–5.45 (m, 3H), 5.6 (d, 1H), 5.85–6.0 (m, 1H), 7.4–7.55 (m, 2H), 7.9–8.0 (dd, 2H), 8.4 (s, 1H).

EXAMPLE B24

Allyl 6-beta-[S-1-Hydroxy-2-oxo-2-(2-phenyl-4-thiazolyl)ethyl]penicillanate

The entire batch of product from Example A21 (0.018 mol presumed) was reacted and product isolated according to Example B10, except to use a reflux time of 3 hours, to use 2:1 hexane:ethyl acetate as eluant on chromatography and to recover mainly the desired S-epimer on chromatography, to yield 1.6 g. of partially purified title product. The latter was rechromatographed with 5:2 hexane:ethyl acetate as eluant to yield purified title product as a foamy solid, 0.78 g.; tlc Rf 0.23 (2:1 hexane:ethyl acetate), 0.12 (5:2 hexane:ethyl acetate); $^1$H-nmr 1.5 (s, 3H), 1.7 (s, 3H), 4.15 (q, 1H), 4.55 (s, 1H), 4.65 (m, 2H), 5.3–5.5 (m, 3H), 5.7 (d, 1H), 5.9 (m, 1H), 7.5 (m, 3H), 8.0 (m, 2H), 8.3 (s, 1H).

EXAMPLE B25

Allyl 6-[S-1-Hydroxy-2-(4-methylphenyl)-2-oxoethyl]penicillanate

Except to use a reaction time of 4 hours at 80°, 3:1 hexane:ethyl acetate as eluant on chromatography, and to recover only of the predominant, more polar S-epimer the method of Example B1 was employed to convert the product of Example A22 (6.0 g., 0.013 mol) to present title product, 1.06 g.; tlc Rf 0.13 (3:1 hexane:ethyl acetate: $^1$H-nmr (300 MHz) 1.5 (s, 3H), 1.7 (s, 3H), 2.45 (s, 3H), 3.65 (br s, 1H), 4.0–4.05 (q, 1H), 4.5 (s, 1H), 4.7 (d, 2H), 5.3–5.4 (m, 2H), 5.4–5.5 (m, 1H), 5.6 (d, 1H), 5.9–6.0 (m, 1H), 7.3–7.4 (d, 2H), 7.9–8.0 (d, 2H).

EXAMPLE B26

Allyl 6-beta-[S-1-Hydroxy-2-(4-methoxycarbonylphenyl)-2-oxoethyl]penicillanate

The entire batch of title product of Example A23 (0.026 mol assumed) as a solution in 200 ml. of toluene was reacted and isolated according to Example B24. 5:2 Hexane:ethyl acetate was employed as eluant on the initial chromatography, and 5:4 ether:hexane for the second chromatography to obtain purified, more polar, more abundant title product, 0.39 g.; tlc Rf 0.16 (2:1 hexane:ethyl acetate).

EXAMPLE B27

Allyl 6-beta-[S-2-(4-cyanophenyl)-1-hydroxy-2-oxoethyl]-penicillanate

The entire batch of product from Example A24 (15.8 g., 0.033 mol assumed) was reacted and crude product isolated according to Example B24. Following initial chromatography with 3:1 hexane:ethyl acetate as eluant, the concentrate of title product (containing about 1 part in 6 of the R-epimer) was fully purified by recrystallization from hot methanol, 0.77 g.; tlc Rf 0.15 (3:1 hexane:ethyl acetate), 0.20 (2:1 hexane:ethyl acetate); 1H-nmr (300 MHz), 1.45 (s, 3H), 1.65 (s, 3H), 3.7 (d,1H), 4.0 (q, 1H), 4.45 (s, 1H), 4.65 (d, 2H), 5.3–5.4 (m, 3H), 5.6 (d, 1H), 5.85–5.95 (m, 1H), 7.7–7.8 (d, 2H), 8.1–8.2 (d, 2H).

EXAMPLE B28

Allyl 6-beta-(S-1-Hydroxy-2-oxo-3-methyl-3-phenoxybutyl)-penicillanate

By the method of Example B24, except to use toluene as solvent, the entire batch of product from Example A25 (3.0 g., 5.7 mmol) was converted to present title product, using 3:1 hexane:ethyl acetate as eluant on chromatography to produce purified title product as an oil, 1.2 g.; tlc Rf 0.23 (3:1 hexane:ethyl acetate).

1H-NMR (CDCl$_3$) delta (ppm): 1.45 (s, 3H), 1.5 (s, 3H), 1.55 (s, 3H), 1.65 (s, 3H), 3.8 (br d, 1H, OH), 3.9 (q, 1H), 4.45 (s, 1H), 4.55 (s, 2H), 4.65 (d, 2H), 5.1 (q, 1H), 5.25–5.4 (dd, 2H), 5.45 (d, 1H), 5.8–6.0 (m, 1H), 7.3–7.4 (m, 5H).

EXAMPLE B29

Allyl 6-beta-[S-1-Hydroxy-2-oxo-3,3-(spirocyclohexyl)-butyl]penicillanate

By the method of the preceding Example, the entire batch of product from Example A26 (12 g., 0.025 mol) was converted to present title product, initially chromatographed with 5:1 hexane:ethyl acetate as eluant and rechromatographed with 32:1 CH$_2$Cl$_2$:acetone as eluant to yield less polar R-isomer, 0.50 g., tlc Rf 0.26 (5:1 hexane:ethyl acetate), 0.38 (32:1 CH$_2$Cl$_2$:ethyl acetate) and title product, the preferred, more polar S-isomer, 1.59 g.; tlc Rf 0.26 (5:1 hexane:ethyl acetate, 0.29 (32:1 CH$_2$Cl$_2$:acetone).

EXAMPLE B30

Allyl 6-beta-[S-1-Hydroxy-2-oxo-2-(1-adamantyl)ethyl]-penicillanate

By the method of Example B28, the product of Example A27 (10.7 g., 0.021 mol) was converted to present title product, chromatographed with 7:1 hexane:ethyl acetate as eluant and triturating the resulting white solids with hexane to remove a small portion of the less desired, less polar R-isomer. The yield was 2.28 g.; tlc Rf 0.18 (3:1 hexane:ethyl acetate: 1H-nmr (300 MHz) 1.5 (s, 3H), 1.7 (s, 3H), 1.75–2.1 (multiplets, 15H), 3.0 (br d, 1H), 3.9 (q, 1H), 4.4 (s, 1H), 4.65 (d, 2H), 4.95 (dd, 1H), 5.25–5.4 (dd, 2H), 5.45 (d, 1H), 5.85–5.95 (m, 1H).

EXAMPLE B31

Allyl 6-beta-[S-1-Hydroxy-2-oxo-2-(4-(t-butyldimethylsiloxymethyl)phenyl)ethyl]penicillanate By the method of Example B28, the product of Example A28 (12 g., 0.020 mol) was converted to present title product, chromatographing with 4:1 hexane:ethyl acetate as eluant to yield less polar R-isomer, 0.03 g., tlc Rf 0.20 (4:1 hexane:ethyl acetate) and preferred, more polar, S-title product, 0.87 g.; tlc Rf 0.15 (4:1 hexane:ethyl acetate); 1H-nmr (300 MHz) 0.1 (s), 0.9 (s), 1.45 (s), 1.65 (s), 3.4 (d), 4.0 (q), 4.45 (s), 4.65 (d), 4.8 (s), 5.25–5.45 (m), 5.55 (d), 5.8–6.0 (m), 7.4 (d), 7.95 (d).

EXAMPLE B32

Allyl 6-beta-[S-1-Hydroxy-2-oxo-2-(4-(1-hydroxy-1-methylethyl)phenyl)ethyl]penicillanate By the method of Example B28, using 4:5 hexane:ethyl acetate as eluant, the product of Example A29 (2.6 g., 5.2 mmol) was converted to present title product, the more polar S-isomer, 0.40 g.; tlc Rf 0.28 (1:1 hexane:ethyl acetate); 1H-nmr (300 MHz) includes 1.45 (s), 1.6 (s), 1.65 (s), 4.0 (q), 4.45 (s).

EXAMPLE B33

Allyl 6-beta-[S-1-Hydroxy-2-oxo-2-(4-(chloromethyl)phenyl)ethyl]penicillanate

By the method of Example B28, using 5:2 hexane:ethyl acetate as eluant on chromatography, the second isomer to elute in the chromatographic separation of Example A30 (0.61 g., 1.21 mmol) was converted to present title product, 0.13 g.; tlc Rf 0.24 (5:2 hexane:ethyl acetate), 0.29 (1:1 hexane:ethyl acetate). Obtained as a by-product was the corresponding dechlorinated material, allyl 6-beta-[S-1-hydroxy-2-oxo-2-(4-methylphenyl)ethyl]penicillanate, 0.13 g.; tlc Rf 0.30 (5:2 hexane:ethyl acetate), 0.34 (2:1 hexane:ethyl acetate).

In like manner, the most polar isomer of Example A30 was converted to present title product, and the least polar isomer was converted to the corresponding 6-beta-(R-isomer).

EXAMPLE B34

Allyl 6-beta-[R- and S-1-Hydroxy-2-(N-methyl-3-indolyl)-2-oxoethyl]penicillanate The entire product from Example A31 (0.043 mol assumed) was taken up in 100 ml. toluene, tributyltin hydride (17.35 ml., 0.0645 mol) added, the mixture refluxed 1 hour, stripped to an oil (14.7 g.) which was chromatographed using 7:1 $CH_2Cl_2$:ethyl acetate as eluant. Fractions containing the less polar isomer were combined and rechromatographed to yield title R-isomer, 3.65 g.; $^1$H-nmr 1.49 (s, 3H), 1.76 (s, 3H), 3.87 (s, 3H), 3.98 (dd, 1H, J=4.73, 7.88 Hz), 4.45 (s, 1H), 4.65 (m, 2H), 5.28 (m, 3H), 5.45 (d, 1H, J=4.73 Hz), 5.93 (m, 1H), 7.35 (m, 3H), 8.08 (s, 1H), 8.38 (m, 1H). Fractions containing the preferred, more polar isomer were combined and rechromatographed to yield title S-isomer, 3.37 g.; tlc Rf 0.3 (7:1 $CH_2Cl_2$:ethyl acetate); $^1$H-nmr 1.47 (s, 3H), 1.69 (s, 3H), 3.86 (s, 3H), 4.06 (dd, 1H, J=4.33, 8.66 Hz), 4.48 (s, 1H), 4.72 (m, 2H), 5.34 (m, 3H), 5.59 (d, 1H, J=4.33 Hz), 5.94 (m, 1H), 7.36 (m, 3H), 8.25 (m, 1H), 8.39 (m, 1H).

EXAMPLE B35

Allyl 6-beta-[S-3-(Benzyloxycarbonylamino)-1-hydroxy-3-methyl-2-oxobutyl]penicillanate By the method of Example B28, using 3:2 hexane:ethyl acetate as eluant on chromatography, the product of Example A32 (4.58 g., 8.2 mmol) was converted to present title product, 0.91 g.; $^1$H-nmr 1.43 (s, 3H), 1.50 (s, 3H), 1.51 (s, 3H), 1.60 (s, 3H), 3.62 (d, 1H, 4 Hz), 3.89 (dd, 1H, J=4 Hz, 4 Hz), 4.40 (s, 1H), 4.62 (d, 2H, 4 Hz), 4.93 (m, 1H), 5.06 (s, 2H), 5.22–5.48 (m, 4H), 5.89 (m, 1H), 7.30 (s, 5H).

EXAMPLE B36

Allyl 6-beta-[S-1-Hydroxy-2-oxo-2-(4-(benzyloxycarbonylamino)phenyl)ethyl]penicillanate By the method of Example B28, using 1:7 ethyl acetate:$CHCl_3$ as eluant on chromatography, the product of Example A33 (2.81 g., 4.65 mmol) was converted to present, less polar, R-isomer of title product, 0.68 g.; and the preferred, more polar title product, 0.94 g.; $^1$H-nmr 1.44 (s, 3H), 1.66 (s, 3H), 3.69 (d, 1H, J=4 Hz), 3.96 (dd, 1H, J=4 Hz, 4 Hz), 4.45 (d, 2H, J=4 Hz), 5.18 (s, 2H), 5.30 (m, 3H), 5.50 (d, 1H, J=3 Hz), 5.89 (m, 1H), 7.35 (s, 5H), 7.46 (d, J=6 Hz), 7.95 (d, 2H, J=6 Hz).

EXAMPLE B37

Allyl 6-beta-6-[S-1-Hydroxy-2-oxo-2-(2-ethoxy-1-naphthyl)ethyl]penicillanate By the method of Example B28, using 1:9 ethyl acetate:$CHCl_3$ as eluant, entire product of Example A34 (11.0 g., 0.02 mol) was converted to present title product, 2.82; $^1$H-nmr 1.27 (s, 3H), 1.40 (t, 3H, J=4 Hz), 1.59 (s, 3H), 3.76 (d, 1H, J=4 Hz), 3.80 (dd, 1H, J=4 Hz, 4 Hz), 4.19 (q, 2H, J=4 Hz), 4.39 (s, 1H), 4.52 (d, 2H, J=4 Hz), 4.89 (d, 1H, J=3 Hz), 5.26 (m, 4H), 5.80 (m, 1H), 7.19 (d, 1H, J=8 Hz), 7.32 (t, 1H, J=4 Hz), 7.43 (t, 1H, J=4 Hz), 7.57 (d, 1H, J=4 Hz), 7.73 (d, 1H, J=4 Hz), 7.87 (d, 1H, J=6 Hz).

EXAMPLE B38

Allyl 6-beta-[S-1-Hydroxy-2-oxo-2-(3-hydroxyphenyl)ethyl]penicillanate

By the method of Example B28, using 1:1 ethyl acetate:hexane as eluant, the product of Example A35 (0.59 g., 1.25 mmol) was converted to present title product, 0.14 g.; oil; $^1$H-nmr 1.39 (s, 3H), 1.59 (s, 3H), 3.94 (dd, 1H, J=4 Hz, 4 Hz), 4.38 (s, 1H), 4.57 (d, 2H, J=4 Hz), 5.25 (m, 3H), 5.45 (d, 1H, J=4 Hz), 5.81 (m, 1H), 6.98 (d, 2H, J=4 Hz), 7.21 (m, 2H), 7.39 (s, 2H).

EXAMPLE B39

Allyl 6-beta-[S-1-Hydroxy-2-oxo-2-(3-quinolyl)ethyl]penicillanate

By the method of Example B10, using a reaction time of 6 hours at 55° and recovering only the preferred S-epimer on chromatography with 1:1 hexane:ethyl acetate as eluant, the product of Example A36 (0.25 g., 0.5 mmol) was converted to present title product, 41 mg.; tlc Rf 0.4 (2:1 ethyl acetate:hexane); $^1$H-nmr 1.44 s, 3H), 1.64 (s, 3H), 4.11 (dd, 1H, J=3 and 4 Hz), 4.48 (s, 1H), 4.63 (d, 3H, J=4 Hz), 5.30 (m, 2H), 5.54 (d, 1H, J=8 Hz), 5.61 (d, 1H, J=3 Hz), 7.56 (t, 1H, J-4 Hz), 7.76 (t, 1H, J=4 Hz), 7.87 (d, 1H, J=4 Hz), 8.05 (d, 1H, J=4 Hz), 8.90 (s, 1H), 9.41 (s, 1H).

EXAMPLE B40

Allyl 6-beta-[S-1-Hydroxy-2-oxo-2-(4-hydroxyphenyl)ethyl]penicillanate

By the method of Example B28, without chromatography, the product of Example A37 (0.16 g., 0.34 mmol) was converted to present title product, 0.11 g.; tlc Rf 0.25 (1:1 ethyl acetate:hexane); $^1$H-nmr 1.47 (s, 3H), 1.70 (s, 3H), 4.04 (dd, 1H, J=4 and 5 Hz), 4.50 (s, 1H), 4.69 (d, 3H, J=4 Hz), 5.38 (m, 4H), 5.57 (d, 1H, J=4 Hz), 5.95 (m, 1H), 6.80 (br d, 2H), 7.94 (d, 2H, J=8 Hz).

EXAMPLE B41

Allyl 6-beta-[S-1-Hydroxy-2-oxo-2-(2-naphthyl)ethyl]penicillanate

By the method of Example B10, without chromatography, the purified product of Example A38 (2.11 g., 4.2 mmol) was converted to present title product, 1.08 g., tlc Rf 0.31 (2:1 hexane:ethyl acetate), $^1$H-nmr 1.46 (s, 3H), 1.71 (s, 3H), 3.74 (d, 1H, J=6 Hz), 4.1 (dd, 1H, J=4 Hz, 4 Hz), 4.50 (s, 1H), 4.66 (d, 1H, J=6 Hz), 5.34 (m, 2H), 5.60 (m, 2H), 5.94 (m, 1H), 7.60 (m, 2H), 7.97 (m, 4H), 8.64 (s, 1H).

METHOD C—ACYLATION

EXAMPLE C1

Allyl 6-beta-[S-1-Acetoxy-2-oxo-2-(phenyl)ethyl]penicillanate

At 0°, the major, more polar (S) title product of Example B1 (100 mg., 0.0027 mol) in 3 ml. of pyridine was treated with 1 ml. of acetic anhydride. The mixture was allowed to warm and after 3 hours was poured into 3 ml. saturated $NaHCO_3$ and extracted with 2×5 ml. ether. The organic layer was stripped to yield title product as an oil, 110 mg., tlc Rf 0.75 (1:1 ether:hexane); $^1$H-nmr 1.48 (s, 3H), 1.76 (s, 3H), 2.12 (s, 3H), 4.20 (dd, 1H, J=4.8, 10 Hz), 2.54 (s, 1H), 4.68 (m, 1H), 5.32–5.44 (m, 2H), 5.68 (d, 1H, J=4.8), 5.96 (m, 1H), 6.78 (d, 1H, J=10 Hz).

EXAMPLE C2

Benzyl 6-beta-[S-1-Acetoxy-2-oxo-2-(phenyl)ethyl]penicillanate

At 0°, S-epimer title product of Example B2 (100 mg., 0.0026 mol) in 2 ml. pyridine containing 0.1 ml. DMAP was treated with 1 ml. acetic anhydride and allowed to warm over 1 hour with stirring, quenched into 2 ml. of chilled saturated NaHCO$_3$ extracted with 2×5 ml. ethyl acetate, dried and stripped to yield title product as a solid foam, 110 mg.; tlc Rf 0.85 (1:1 ethyl acetate:hexane); 1.44 (s, 3H), 1.68 (s, 3H), 2.12 (s, 3H), 4.21 (dd, 1H, J=4.5, 8.5 Hz), 5.22 (s, 1H), 5.57 (d, 1H, J=4.5 Hz), 6.34 (d, 1H), J=8.5 Hz), 7.30–8.06 (m, 10H); i.r. (CHCl$_3$) cm$^{-1}$: 2970 (m), 1780 (s), 1745 (s), 1695 (s), 1450 (m), 1230 (s), 765 (s).

EXAMPLE C3

Benzyl 6-beta-[R-1-Acetoxy-2-oxo-2-(phenyl)ethyl]penicillanate

By the method of the preceding Example, R-epimer title product of Example B2 (200 mg.) was converted to present title product, 220 mg. as an oil, tlc Rf 0.70 (1:1 ethyl acetate:hexane), $^1$H-nmr 1.42 (s, 3H), 1.66 (s, 3H), 2.12 (s, 3H), 4.21 (dd, 1H, J=4.5, 9.5 Hz), 5.21 (s, 2H), 5.54 (d, 1H, J=4.5 Hz), 6.34 (d, 1H, J=9.5 Hz), 7.32–8.10 (m, 10H); i.r. (neat) cm$^{-1}$: 2985 (m), 1780 (s), 1748 (s), 1692 (s), 1600 (w), 1450 (w), 1375 (m), 1230 (s).

METHOD D—DEPROTECTION OF ALLYL ESTERS

EXAMPLE D1

Potassium 6-beta-[S-(1-Hydroxy-2-oxo-2-(phenyl)ethyl]penicillanate

The major, more polar (S) title product of Example B1 (0.56 g., 1.5 mmols) was dissolved in 25 ml. ethyl acetate, treated in sequence with tetrakis(triphenylphosphine)palladium (0.086 g., 0.075 mmol), triphenylphosphine (0.086 g., 0.33 mmols) and finally with potassium 2-ethylhexanoate in ethyl acetate (2.98 ml. of 0.5M, 1.5 mmols), stirred for 2 hours and filtered to recover present crude title product. The latter was dissolved in 30 ml. H$_2$O, washed 2×30 ml. ethyl acetate, and freeze dried to yield purified title product, 324 mg.; $^1$H-nmr (D$_2$O) 1.34 (s, 3H), 1.50 (s, 3H), 3.98 (dd, 1H, J=4.2, 9.9 Hz), 4.15 (s, 1H), 5.40 (d, 1H, J=4.2 Hz), 5.44 (d, 1H, J=9.9 Hz), 7.43–7.89 (m, 5 Hz); i.r. (KBr) cm$^{-1}$ 3449 (b), 2965 (w), 1785 (s), 1760 (s), 1595 (m), 1620 (s), 1380 (m), 1240 (m).

EXAMPLE D2

Sodium 6-beta-[R-1-Hydroxy-2-oxo-2-(phenyl)ethyl]penicillanate

To the minor, less polar (R) title product of Example B1 (150 mg., 0.0004 mol) in 6 ml. of ethyl acetate was added in sequence tetrakis(triphenylphosphine)palladium (20 mg.), triphenylphosphine (20 mg.) and 0.8 ml. (0.0004 mol) of 0.5M potassium 2-ethylhexanoate in ethyl acetate. After stirring 1 hour, the mixture was diluted with ether, precipitating gummy solids. The whole was extracted with an equal volume of water; the aqueous layer was separated, acidifed with dilute HCl, and washed with an equal volume of ethyl acetate; and the ethyl acetate layer was evaporated. The resulting free acid was dissolved in water by neutralization with NaHCO$_3$, and the solution washed with ethyl acetate and finally freeze dried to yield title product as a glassy solid, 30 mg.; $^1$H-nmr (D$_2$O): 1.39 (s, 3H), 1.54 (s, 3H), 4.05 (s, 1H), 4.06 (dd, 2H, J=4.2, 10 Hz), 5.38 (d, 1H, J=4.2 Hz), 5.50 (d, 1H, J=10 Hz), 7.40–7.88 (m, 5H).

EXAMPLE D3

Potassium 6-beta-[S-1-Acetoxy-2-oxo-2-(phenyl)ethyl]penicillanate

Title product of Example Cl (100 mg., 0.00024 mol) was dissolved in 5 ml. ethyl acetate. Tetrakis(triphenylphosphine)palladium (15 mg.) triphenylphosphine (15 mg.) were added and the mixture stirred for 30 minutes. Potassium 2-ethylhexanoate in ethyl acetate (250 ml. of 0.5M) was then added and the mixture stirred 2 hours, and extracted with a half volume of water. With some difficulty, because of emulsion problems, the aqueous layer was separated and freeze dried to yield title product as a gummy solid, 70 mg.; $^1$H-nmr (D$_2$O) 1.40 (s, 3H), 1.58 (s, 3H), 2.02 (s, 3H), 4.18 (dd, 1H, J=4.2, 9.5 Hz), 4.20 (s, 1H), 5.48 (d, 1H, J=4.2 Hz), 6.42 (d, 1H, J=9.5 Hz), 7.40–7.96 (m, 5H).

EXAMPLE D4

Potassium 6-beta-(S-1-Hydroxy-2-oxo propyl)penicillanate

Title product of Example B3 (75 mg., 0.24 mmol) was dissolved in 2.5 ml. of ethyl acetate and treated in sequence with tetrakis(triphenylphosphine)palladium (14 mg., 0.053 mmol) and potassium 2-ethylhexanoate (0.5 ml. of 0.5M, 0.25 mmol). After 5 minutes of stirring, material began to precipitate from the resulting solution. After stirring 2.5 hours, crude, hygroscopic title product was recovered by filtration (130 mg.). The latter was taken up in 5 ml. H$_2$O, extracted with 5 ml. ethyl acetate, and the aqueous phase freeze dried to yield solid title product, 48 mg.; tlc Rf 0.01 (1:1 ethyl acetate:hexane); $^1$H-nmr (D$_2$O) 1.41 (s, 3H), 1.55 (s, 3H0, 2.23 (s, 3H), 3.84 (dd, 1H, J=3.9, 9.6 Hz), 4.16 (s, 1H), 4.62 (d, 1H), J=9.6 Hz), 5.43 (d, 1H, J=3.9 Hz); i.r. (KBr) cm$^{-1}$ 3500 (b), 2985 (m), 1775 (s), 1760 (s), 1605 (s), 1395 (m), 1200 (s), 1060 (m).

EXAMPLE D5

Potassium 6-beta-[R-1-Hydroxy-2-oxopropyl)-penicillinate

According to the method of the preceding Example, title product of Example B4 (0.14 g., 0.0045 mole) was converted to instant title product. Since the crude precipitate was tacky and did not filter well, the reaction mixture was diluted with 5 ml. ethyl acetate and 10 ml. H$_2$O. The aqueous and freeze dried to yield title product as hygroscopic foam, 140 mg.; $^1$H-nmr (D$_2$O) 1.41 (s, 3H), 1.58 (s, 3H), 2.26 (s, 3H), 3.92 (dd, 1H, J=3.6, 9.6 Hz), 4.12 (s, 1H), 5.34 (d, 1H, 3.6 Hz); i.r. (KBr) cm$^{-1}$ 3450 (b), 2995 (w), 1760 (s), 1610 (s), 1400 (s), 1320 (m).

EXAMPLE D6

Potassium 6-beta-[R-1-Hydroxy-2-oxo-2-(2-furyl)ethylpenicillanate

By the method of Example 1, except to add the potassium ethyl hexanoate 15 minutes later than the other reagents, the 1p R-epimer title product of Example B5 (80 mg.) was converted to present freeze dried title product, 65 mg.; $^1$H-nmr (D$_2$O) 1.52 (s, 3H), 1.69 (s, 3H), 4.13 (dd, 1H), 4.18 (s, 1H), 5.38 (d, 1H), 5.52 (d, 1H), 6.72 (m, 1H), 7.62 (d, 1H), 7.89 (m, 1H); i.r. (KBr) cm$^{-1}$ 3480 (b), 1760 (s), 1670 (s), 1610 (s), 1470 (m), 1390 (m), 1320 (m).

EXAMPLE D7

Potassium 6-beta-[S-1-Hydroxy-2-oxo-2-(2-furyl)ethyl]penicillanate

By the method of Example D6, the mp, S-epimer title product of Example B5 (125 mg.) was converted to present freeze dried title product, 97 mg.; $^1$H-nmr (D$_2$O): 1.45 (s, 3H), 1.62 (s, 3H), 4.11 (dd, 1H), 4.24 (s, 1H), 5.28 (d, 1H), 5.47 (d, 1H), 6.73 (m, 1H), 7.68 (m, 1H), 7.89 (m, 1H); i.r. (KBr) cm$^{-1}$ 3475 (b), 1785 (s), 1685 (s), 1610 (s), 1470 (m), 1390 (m), 1320 (m).

EXAMPLE D8

Potassium 6-beta-[S-1-Hydroxy-2-oxo-2-(4-methoxyphenyl)ethyl]-penicillante

By the method of Example D6, the S-title product of Example B6 (221 mg.) was converted to instant title product, 174 mg.; $^1$H-nmr (D$_2$O) 1.44 (s, 3H), 1.60 (s, 3H), 3.88 (s, 3H), 4.14 (dd, 1H), 4.23 (s, 1H), 5.50 (m, 2H), 7.05 (d, 2H), 8.00 (d, 2H); (KBr) cm$^{-1}$: 3450 (b) 2995 (w), 1785 (s), 1770 (m), 1685 (m), 1610 (s), 1395 (m), 1320 (m), 1275 (m), 1180 (m).

EXAMPLE D9

Potassium 6-beta-[R-1-Hydroxy-2-oxo-2-(4-methoxyphenyl)ethyl]penicillanate

By the method of Example D6, the R- title product of Example B6 (124 mg.) was converted to instant title product, 93 mg.; $^1$H-nmr (D$_2$O) 1.51 (s, 3H), 1.67 (s, 3H), 3.90 (s, 3H), 4.15 (m, 1H), 4.16 (s, 1H), 5.47 (d, 1H), 5.58 (d, 1H), 7.15 (d, 2H), 8.01 (d, 1H); ir (KBr) cm$^{-1}$ 3420 (b), 2995 (w), 1770 (s), 1680 (m), 1610 (s), 1400 (m), 1365 (m), 1180 (m).

EXAMPLE D10

Potassium 6-beta-[S-1-Hydroxy-2-oxo-2-(2-thienyl)ethyl]penicillanate

Title product of Example B7 (130 mg.) was reacted according to the method of Example D1. At the end of the reaction period the reaction mixture was diluted with 10 ml. of ethyl acetate and 20 ml. of water. The aqueous layer was separated, washed 2×20 ml. fresh ethyl acetate and freeze dried to yield title product, in excess of 20 mg.; ir (KBr) cm$^1$ 3480 (b), 2985 (w), 1790 (s), 1770 (s), 1670 (m), 1610 (s), 1390 (m); $^1$H-nmr (D$_2$O) 1.63 (s, 3H), 4.11 (dd, 1H), 4.28 (s, 1H), 5.39 (d, 1H), 5.50 (d, 1H), 7.30 (dd, 1H), 7.98 (m, 1H), 8.11 (dd, 1H).

EXAMPLE D11

Potassium 6-beta-[R-1-Hydroxy-2-oxo-2-(2-thienyl)ethyl]penicillanate

By the method of the preceding Example, title product of Example B8 (300 mg.) was converted to instant, freeze dried, title product, in excess of 20 gm.; ir (KBr) cm$^{-1}$: 3420 (b), 2985 (w), 1785 (s), 1765 (s), 1605 (s), 1415 (m); $^1$H-nmr (D$_2$O) 1.56 (s, 3H), 1.72 (s, 3H), 4.22 (dd, 1H), 4.23 (s, 1H), 5.46 (d, 1H), 5.58 (s, 1H), 7.32 (m, 1H), 8.06 (m, 2H).

EXAMPLE D12

Potassium 6-beta-[S-1-Hydroxy-2-oxo-2-(phenyl)ethyl]penicillanate 1-beta-Oxide According to the method of the preceding Example, the beta-oxide of Example F1 (80 mg., 0.2 mmole) was converted to freeze dried title product, in excess of 20 mg.; ir (KBr) cm$^{-1}$ 3450 (b), 2995 (w), 1780 (s), (s), 1680 (s), 1620 (s), 1445 (w), 1390 (m), 1330 (m), 1060 (m); $^1$H-nmr (D$_2$O) 1.28 (s, 3H), 1.60 (s, 3H), 4.14 (dd, 1H), 4.34 (s, 1H), 5.35 (d, 1H), 5.89 (d, 1H), 7.52–8.01 (m, 5H).

EXAMPLE D13

Potassium 6-beta-[S-1-Hydroxy-2-(phenyl)-ethyl]penicillanate 1-alpha-Oxide

According to the method of Example D11, the alphaoxide of Example F1 (0.1 g.) was convert to freeze dried title product; ir (KBr) cm$^{-1}$ 3420 (b), 2990 (w), 1775 (s), 1685 (m), 1620 (s), 1400 (m), 1040 (m); $^1$H-nmr (D$_2$O): 1.34 (s, 3H), 1.65 (s, 3H), 4.28 (s, 1H), 4.42 (dd, 1H), 4.90 (d, 1H), 4.81 (d, 1H), 7.55–8.04

EXAMPLE D14

Potassium 6-beta-[S-1-Hydroxy-2-oxo-2-(phenyl)ethyl]penicillanate 1,1-Dioxide According to the method of Example D11, the title product of Example F2 (0.028 g.) was converted to instant, freeze dried title product, in excess of 20 mg.; $^1$H-nmr (D$_2$O) 1.45 (s, 3H), 1.55 (s, 3H), 4.25 (dd, 1H), 4.35 (s, 1H), 5.31 (d, 1H), 5.95 (d, 2H), 7.58–8.10 (m, 5H).

EXAMPLE D15

Potassium 6-beta-[S-1-Hydroxy-2-oxo-2-(1-naphthyl)ethyl]penicillanate

By the procedure of Example D1, the more polar, S-epimer of Example B9 (0.40 g., 0.94 mmol) was converted to an ethyl acetate solution of title product. The reaction mixture was diluted with 30 ml. of water and the aqueous layer separated, washed 5×20 ml. fresh ethyl acetate and freeze dried to yield title product as a powder, 300 mg.; $^1$H-nmr 1.35 (s, 3H), 1.58 (s, 3H), 4.09 (dd, 1H), 4.21 (s, 1H), 5.28 (d, 1H), 5.60 (s, 1H), 7.58–8.20 (m, 7H); ir (KBr) cm$^{-1}$ 3815 (s, b), 2985 (w), 1740 (s), 1720 s), 1600 (s), 1400 (m), 1315 (w).

EXAMPLE D16

Potassium 6-beta-(S-1-Hydroxy-2-oxo-3-phenylpropyl)penicillanate

Title product of Example G1 (116 mg., 0.28 mmol) was dissolved in 6 ml. of ethyl acetate. Added in sequence were tetrakis(triphenylphosphine)palladium (10 mg.), triphenylphosphine (10 mg.) and potassium ethylhexanoate (0.57 ml. of 0.5M in ethyl acetate, 0.28 mmol). After stirring 30 minutes, the mixture was filtered and the cake washed 4×10 ml. ethyl acetate. The filtercake was taken up in 15 ml. $H_2O$, washed 3×15 ml. of fresh ethyl acetate, and freeze dried to yield title product as a white, fluffy powder, 61 mg.; $^1$H-nmr 1.45 (s, 3H), 1.57 (s, 3H), 3.92 (dd, 1H), 4.07 (s, 2H), 4.20 (s, 1H), 4.78 (d, 1H), 5.45 (d, 1H), 7.23 (d, 2H), 7.36 (m, 3H).

EXAMPLE D17

Potassium 6-beta-[S-1-Hydroxy-2-oxo-3-(2-thienyl)propyl]penicillanate

To title product of Example G2 (0.255 g., 0.64 mmol) dissolved in 8 ml. ethyl acetate were added in sequence tetrakis(triphenylphosphine)palladium (15 mg.), triphenylphosphine (15 mg.) and potassium 2-ethylhexanoate (1.28 ml. of 0.5M in ethyl acetate, 0.64 mol). After 30 minutes, the reaction mixture was filtered, recovering palladium catalyst, but the precipitated, colloid-like product passing through the filter paper. The filtrate was extracted with 30 ml. $H_2O$. The aqueous phase was separated, backwashed 4×20 ml. fresh ethyl acetate and freeze dried to yield crude title product, 243 mg. The latter was triturated with ethyl acetate to obtain purified title product, 159 mg.; $^1$H-nmr ($D_2O/CD_3CN$) 1.81 (s, 3H), 1.94 (s, 3H), 4.20 (dd, 1H), 4.52 (s, 1H), 4.62 (s, 2H), 5.09 (d, 1H), 5.80 (d, 1H), 7.31 (m, 1H), 7.40 (m, 1H), 7.73 (m, 1).

EXAMPLE D18

Potassium 6-beta-[S-1-Hydroxy-2-oxo-2-(4-methoxyphenyl)ethyl]penicillanate 1-alpha-Oxide By the method of Example D16, the 1-alpha-oxide title product of Example F3 (50 mg., 0.12 mmol) was converted to above title product, 48 mg.; $^1$H-nmr ($D_2O$) 1.27 (s, 3H), 1.63 (s, 3H), 3.94 (s, 3H), 4.16 (dd, 1H), 4.36 (s, 1H), 5.37 (d, 1H), 5.86 (d, 1H), 7.12 (d, 2H), 8.05 (d, 2H).

EXAMPLE D19

Potassium 6-beta-[S-1-Hydroxy-2-oxo-2-(4-methoxyphenyl)ethyl]penicillanate 1-beta-Oxide By the method of Example D16, the 1-beta-oxide title product of Example F3 (50 mg., 0.12 mmol) was converted to above title product, 53 mg.; $^1$H-nmr ($D_2O$) 1.35 (s, 3H), 1.65 (s, 3H), 3.94 (s, 3H), 4.29 (s, 1H), 4.41 (dd, 1H), 4.91 (d, 1H), 5.78 (d, 1H), 7.13 (d, 2H), 8.05 (d, 2H).

EXAMPLE D20

Potassium 6-beta-[R-1-Hydroxy-2-oxo-(4-methoxyphenyl)ethyl]penicillanate 1-beta-Oxide By the method of Example D15, title product of Example F4 (50 mg., 0.12 mmol) was converted to above title product, 40 mg.; $^1$H-nmr ($D_2O$) 1.33 (s, 3H), 1.72 (s, 3H), 3.93 (s, 3H), 4.34 (s, 1H), 4.42 (dd, 1H), 5.20 (d, 1H), 5.85 (d, 1H), 7.10 (d, 2H), 8.01 (d, 2H).

EXAMPLE D21

Potassium 6-beta[S-1-Hydroxy-2-oxo-2-(4-dimethylaminophenyl)ethyl]penicillanate

By the method of Example D16, the S-title product of Example B12 (0.20 g., 0.48 mmol) was converted to instant title product, 0.14 g.; $^1$H-nmr ($D_2O$) 1.45 (s, 3H), 1.63 (s, 3H), 3.07 (s, 6H), 4.08 (dd, 1H), 4.27 (s, 1H), 5.46 (d, 1H), 5.51 (d, 1H), 6.82 (d, 2H), 7.94 (d, 2H); ir (KBr) $cm^{-1}$: 3433 (b), 2975 (w), 1780 (s), 1655 (s), 1601 (s), 1375 (m), 1197 (m).

EXAMPLE D22

Potassium 6-beta-[R-1-Hydroxy-2-oxo-2-(4-dimethylaminophenyl)ethyl]penicillanate By the method of Example 16, the R-title product of Example B12 (0.20 g., 0.48 mmol) was converted to instant title product, 0.13 g.; $^1$H-nmr ($D_2O$) 1.54 (s, 3H), 1.69 (s, 3H), 3.05 (s, 6H), 4.15 (dd, 1H), 4.19 (s, 1H), 5.50 (d, 1H), 5.60 (d, 1H), 6.77 (d, 2H), 7.89 (d, 2H); ir (KBr) $cm^{-1}$: 3460 (b), 2988 (w), 1756 (m), 1603 (s), 1193 (w).

EXAMPLE D23

Sodium 6-beta-[S-1-Hydroxy-2-oxo-2-(4-fluorophenyl)ethyl]penicillanate

The S-title product of Example B13 (2.16 g.; 5.49 mmol) was dissolved in 20 ml. $CH_2Cl_2$ and purged with $N_2$. Added in sequence were triphenylphosphine (220 mg.), sodium ethylhexanoate (3.95 ml. of 1.391M in ethyl acetate, 5.49 mmol) and tetrakis(triphenylphosphine)palladium (220 mg.). After 1 hour, title product was recovered by filtration, with 4:1 ethyl acetate: $CH_2Cl_2$ and finally ether wash, 2.08 g.; $^1$H-nmr ($D_2O$) 1.45 (s, 3H), 1.61 (s, 3H), 4.08 (q, 1H), 4.25 (s, 1H), 5.516 (d, 1H), 5.523 (d, 1H), 7.28 (m, 2H), 8.08 m, 2H); ir (KBr) $cm^{-1}$ 1770, 1754, 1688, 1602.

EXAMPLE D24

Sodium 6-beta-[R-1-Hydroxy-2-oxo-2-(4-fluorophenyl)ethyl]penicillanate

By the method of the preceding Example, R-title product of Example B13 (1.06 g., 2.69 mmol) was converted to a $CH_2Cl_2$ solution of instant title product. (An equal volume of ethyl acetate was added and $CH_2Cl_2$ stripped, but product remained in solution.) The mixture was stripped of solvent and the residual oil triturated with hexane and then 1:1 ethyl acetate: hexane to yield crude title product as a filterable solid, 0.79 g. The latter was taken into ethyl acetate and water (5 ml. of each). The pH was adjusted from 8.1 to 2.8 and the layers separated. The aqueous layer was extracted with 5 ml. fresh ethyl acetate, and the organic layers were combined and stripped to yield 6-beta-[R-1-hydroxy-2-oxo-2-(4-fluorophenyl)ethyl]penicillanic acid, 0.513 g. (1.45 mmols). The latter was taken up in 5 ml. ethyl acetate. Sodium ethylhexanoate (1.04 ml. of 1.391N in ethyl acetate 1.45 mmols) was added, and title product precipitated by the addition of three volumes of hexane, 0.43 g.; $^1$H-nmr (D$_2$O) 1.52 (s, 3H), 1.67 (s, 3H), 4.19 (s,1H), 4.20 (q, 1H), 5.49 (d, 1H), 5.61 (d, 1H), 7.29 (m, 2H), 8.08 (m, 2H); ir (KBr) cm$^{-1}$ 1757, 1685, 1602, 1372.

EXAMPLE D25

Potassium 6-beta-[S-1-Hydroxy-2-oxo-2-(4-(propenyloxy)phenyl)ethyl]penicillanate By the method of Example D16, title product of Example B14 (65 mg., 0.15 mmol) was converted to instant title product, 52 mg.; $^1$H-nmr (D$_2$O): 1.45 (s, 3H), 1.62 (s, 3H), 1.68 (dd, 3H), 4.05 (dd, 1H), 4.25 (s, 1H), 5.14 (m, 1H), 5.52 (2d, 2H), 6.52 (m, 1H), 7.12 (d, 2H), 8.02 (d, 2H); ir (KBr) cm$^{-1}$ 3450 (b), 2985 (w), 1785 (s), 1770 (s), 1690 (s), 1610 (s), 1395 (m), 1280 (m).

EXAMPLE D26

Potassium 6-beta-[R-1-Hydroxy-2-oxo-2-(4-(propenyloxyphenyl))ethyl]penicillanate By the method of Example D16, except that an equal volume of ether was added to the reaction to initially precipitate the product, title product of Example B15 (62.5 mg., 0.145 mmol) was converted to instant title product, 41 mg.; $^1$H-nmr (D$_2$O): 1.52 (s, 3H), 1.65 (m, 6H), 4.18 (m, 2H), 5.15 (m, 1H), 5.49 (d, 1H), 5.58 (d, 1H), 6.54 (m, 1H), 7.13 (d, 2H), 8.00 (d, 2H); ir (KBr) cm$^{-1}$ 3450 (b), 1760 (s), 1680 (s), 1610 (s), 1400 (m).

EXAMPLE D27

Potassium 6-beta-[S-1-Hydroxy-2-(4-hydroxyphenyl)-2-oxoethyl]penicillanate

By the method of Example D16, title product of Example G3 (25 mg., 0.064 mmol) was converted to instant title product, 8.5 mg., 1H-nmr (D$_2$O): 1.42 (s, 3H), 1.62 (s, 3H), 4.05 (dd, 1H), 4.23 (s, 1H), 5.46 (d, 1H), 5.50 (d, 1H), 6.82 (d, 2H), 7.95 (d, 2H).

EXAMPLE D28

Potassium 6-beta-[S-2-(3-Thienyl)-2-oxo-1-hydroxyethyl]penicillanate

Title product of Example B16 (1.50 g., 0.0039 mol) was dissolved in 25 ml. ethyl acetate. Added in sequence were palladium tetrakis-(triphenylphosphine) (100 mg., 0.087 mmol) and triphenylphosphine (100 mg., 0.39 mmol) and the mixture stirred 3 minutes. Finally potassium 2-ethylhexanoate (7.86 ml. of 0.5M in ethyl acetate, 0.0039 mol) was added by syringe over 2 minutes. After stirring 2.5 hours, solids were recovered by filtration and repulped in ethyl acetate to yield title product, 0.92 g.; mp 233°-234° (dec); ms: parent 263, base 100; $^1$H-nmr (D$_2$O) delta (300 MHz); 1.45 (d, 3H), 1.65 (d, 3H), 4.1 (m, 1H), 4.3 (s, 1H), 5.4 (d, 1H), 5.5 (d, 1H), 7.6 (m, 1H), 8.6 (s, 1H).

EXAMPLE D29

Sodium 6-beta-[S-2-(1-Methyl-2-pyrrolyl)-2-oxo-1-hydroxyethyl]penicillanate

The more polar, S-epimer product of Example B17 (1.15 g., 3.04 mmol) in 12 ml. ethyl acetate and 5 ml. CH$_2$Cl$_2$ was reacted with palladium tetrakis(triphenylphosphine) 120 mg.), triphenylphosphine (120 mg.) and sodium ethylhexanoate (2.2 ml. of 1.39M in 12:5 ethyl acetate:CH$_2$Cl$_2$) according to the preceding Example. After the 2.5 hour reaction period, CH$_2$Cl$_2$ was stripped and replaced with ethyl acetate. Title product was recovered by filtration, with ethyl acetate and finally ether wash, 0.99 g.; ir (KBr) 1752, 1643 and 1605 cm$^{-1}$; $^1$H-nmr (D$_2$O) delta: 1.43 (s, 3H), 1.61 (s, 3H), 3.87 (s, 3H), 4.07 (dd, 1H, J=4 Hz, 9.4 Hz), 4.23 (s, 1H), 5.28 (d, 1H, J=9.4 Hz), 5.40 (d, 1H, J=4 Hz), 6.28 (m, 1H), 7.18 (m, 1H), 7.4 (m, 1H).

EXAMPLE D30

Sodium 6-beta-[R-2-(1-Methyl-2-pyrrolyl)-2-oxo-1-hydroxyethyl]penicillanate

The less polar, R-epimer product of Example B17 (1.21 g., 0.0032 mol) was converted by the method of the preceding Example, to crude title product, 0.84 g. The latter was taken up in 10 ml. of water and 10 ml. of ethyl acetate and filtered. The aqueous layer was separated, extracted with another 10 ml. of fresh ethyl acetate, the pH adjusted from 8.3 to 7.5 with dilute HCl, re-extracted with 10 ml. fresh ethyl acetate, adjusted to pH 3.0 with dilute HCl, and the free acid form of title product extracted into 2×10 ml. further ethyl acetate. The acidic ethyl acetate extracts were combined, dried over Na$_2$SO$_4$ and stripped to yield 6-beta-[R-2-(1-methyl-2-pyrrolyl)-2-oxo-1-hydroxyethyl]penicillanic acid, 0.65 g. (1.8 mmol). The latter was taken up in 6 ml. ethyl acetate, 1.3 ml. of 1.39N sodium ethylhexanoate in ethyl acetate (1.8 mmol) was added, followed by 10 ml. of ether, and precipitated title product was recovered by filtration, 0.346 g.; ir (KBr) 1766, 1636, 1616 cm$^{-1}$; $^1$H-nmr (D$_2$O) delta: 1.53 (s, 3H), 1.67 (s, 3H), 3.91 (s, 3H), 4.12 (dd, 1H, J=4,10 Hz), 4.18 (s, 1H), 5.35 (d, 1H), J=10 Hz), 5.51 (d, 1H, J=4 Hz), 6.26 (m, 1H), 7.21 (m, 1H), 7.25 (m, 1H).

EXAMPLE D31

Sodium 6-beta-[S-2-(1-Benzyl-2-pyrrolyl)-2-oxo-1-hydroxyethyl]penicillanate

According to the method of Example D29, more polar S- title product of Example B18 (2.68 g., 0.0059 mol) was converted to instant title product, 1.8 g.; $^1$H-nmr (D$_2$O) delta: 1.35 (s, 3H), 1.55 (s, 3H), 3.81 (dd, 1H, J=4.3, 10.2 Hz), 4.14 (s, 1H), 4.92 (d, 1H, J=4.3 Hz), 5.2 (d, 1H, J=10.2 Hz), 5.48 (ABq, 2H, J=15.4 Hz), 6.34 (m, 1H), 7.02 (m, 1H), 7.34 (m, 6H); ir (KBr) 1758, 1642, 1607 cm$^{-1}$.

EXAMPLE D32

Sodium 6-beta-[R-2-(1-Benzylpyrrolyl)-1-hydroxy-2-oxoethyl]penicillanate

By the method of the preceding Example, less polar R-title product of Example B18 (1.17 g., 2.57 mmols)

was converted to instant title product 0.50 g., $^1$H-nmr (D$_2$O) 1.49 (s, 3H), 1.65 (s, 3H), 3.98 (dd, 1H), J=4.2, 9.1 Hz), 4.14 (s, 1H), 5.25 (d, 1H, J=4.2 Hz), 5.33 (d, 1H, J=9.1 Hz), 5.56 (ABq, 2H, J=15.6 Hz), 6.36 (m, 1H), 7.07 (m, 2H), 7.34 (m, 5H); ir (KBr) 1761, 1640, 1611 cm$^{-1}$.

EXAMPLE D33

Potassium 6-beta-[S-2-(2-Methoxyphenyl)-1-hydroxy-2-oxoethyl]-penicillanate

By the procedure of Example D28, the more polar S-title product of Example B19 (3.38 g., 0.0083 mol) was converted to instant title product, 2.50 g.; mp 199°-201° (dec); $^1$H-nmr (D$_2$O) 1.45 (s, 3H), 1.65 (s, 3H), 3.95 (s, 3H), 3.95-4.05 (m, 1H), 4.25 (s, 1H), 5.45 (d, 1H), 5.55 (d, 1H), 7.1-7.25 (m, 2H), 7.6-7.7 (m, 2H).

EXAMPLE D34

Potassium 6-beta-[R-2-(2-Methoxyphenyl)-1-hydroxy-2-oxoethyl]-penicillanate

By the procedure of Example D28, the less polar R-title product of Example B19 (1.18 g., 0.0029 mol) was converted to instant title product, 0.50 g.; mp 184°-186°; $^1$H-nmr (D$_2$O) 1.5 (s, 3H), 1.65 (s, 3H), 3.95 (s, 3H), 4.05-4.1 (dd, 1H), 4.15 (s, 1H), 5.4 (d, 1H), 5.7 (d, 1H), 7.1-7.25 (m, 2H), 7.6-7.7 (m, 2H).

EXAMPLE D35

Sodium 6-beta-(S-1-Hydroxy-3,3-dimethyl-2-oxobutyl)penicillanate

More polar, S-title product of Example B20 (2.61 g., 0.0073 mol) was dissolved in a mixture of 25 ml. of ethyl acetate and 10 ml. CH$_2$Cl$_2$. Sodium ethylhexanoate (5.80 ml. of 1.25M in ethyl acetate 0.0072 mol), (C$_6$H$_5$)$_3$P (260 mg) and Pd[(C$_6$H$_5$)$_3$P]$_4$ (260 mg.) were added sequentially and the mixture stirred for 3 hours, diluted with 20 ml. ethyl acetate, and present title product recovered by filtration, 1.48 g.; ir (KBr) 1770, 1705, 1597 cm$^{-1}$; $^1$H-nmr (D$_2$O) 1.24 (s, 9H), 1.47 (s, 3H), 1.62 (s, 3H), 3.93 (dd, 1H, J=4.35, 9.88), 4.22 (s, 1H), 5.06 (d, H, J=9.88), 5.42 (d, 1H, J=4.35).

EXAMPLE D36

Sodium 6-beta-(R-1-Hydroxy-3,3-dimethyl-2-oxobutyl)penicillanate

Less polar, R-title product of Example B20 (0.67 g., 0.0019 mol) was converted to present title product according to the preceding Example. Following dilution of the mixture with ethyl acetate, the CH$_2$Cl$_2$ was stripped away, an equal volume of water was added and the pH was adjusted to 8.5 with dilute NaOH. The aqueous phase was separated, adjusted to pH 7.5 with dilute HCl, extracted 2x equal volume 1:1 ether:hexane, adjusted to pH 2.5 and extracted with 2x equal volume of ethyl acetate. The latter ethyl acetate extracts were combined layered with one half volume of water and the pH adjusted to 7.5 with dilute NaOH. The aqueous layer was separated and freeze dried to produce present title product, 0.392 g.; ir (KBr) 1768, 1694, 1606 cm$^1$; $^1$H-nmr (D$_2$O) 1.19 (s, 9H), 1.52 (s, 3H), 1.65 (s, 3H), 4.16 (dd, 1H, J=9.88, 4.03), 4.17 (s, 1H), 5.08 (d, 1H, J=9.88), 5.48 (d, 1H, J=4.03).

EXAMPLE D37

Sodium 6-beta-[S-1-Hydroxy-2-(N-methyl-2-indolyl)-2-oxoethyl]penicillanate

The more polar, S-title product of Example B21 (5.46 g., 0.0013 mol) was converted to present title product according to the method of Example D35; 4.27 g.; ir (KBr), 1760, 1657, 1602 cm$^{-1}$; $^1$H-nmr (D$_2$O, 250 MHz), 1.34 (s, 3H), 1.51 (s, 3H), 3.67 (s, 3H), 4.06 (dd, 1H, J=4.4, 9.87), 4.20 (s, 1H), 5.34 (d, 1H, J=9.87), 5.40 (d, 1H, J=4.4), 7.27 (m, 5H).

EXAMPLE D38

Sodium 6-beta-[R-1-Hydroxy-2-(N-methyl-2-indolyl)-2-oxoethyl]penicillanate

The less polar, R-title product of Example B21 (1.25 g., 0.0029 mol) was converted to present title product, initially formed as gummy solids. Solvents were stripped and the residue repeatedly triturated with ethyl acetate until title product was obtained as filterable solids, 0.818 g.; ir 1760, 1659, 1606 cm$^{-1}$; $^1$H-nmr (D$_2$O, 250 MHz), 1.49 (s, 3H), 1.57 (s, 3H), 3.71 (s, 3H), 4.10 (s, 1H), 4.12 (m, 1H, dd obscured), 5.38 (d, 1H, J=9.60), 5.50 (d, 1H, J=4.03).

EXAMPLE D39

Sodium 6-beta-[S-1-Hydroxy-2-(1-methyl-2-imidazolyl)-2-oxoethyl]penicillanate

By the method of Example D35, the product of Example B22 (39 mg., 0.1 mmol) was converted to present title product, 16 mg.; $^1$H-nmr (D$_2$O) 1.44 (s, 3H), 1.61 (s, 3H), 3.97 (s, 3H), 4.14 (dd, 1H, J=9.6, 4.5), 4.24 (s, 1H), 5.45 (d, 1H, J=4.5), 5.58 (d, 1H, J=9.6), 7.22 (s, 1H), 7.42 (s, 1H).

EXAMPLE D40

Potassium 6-beta-[S-2-(2-Benzothienyl)-1-hydroxy-2-oxoethyl]-penicillanate

The product of Example B23 (0.90 g., 0.0021 mol) was dissolved in 12 ml. ethyl acetate. Added sequentially, each over 3-5 minutes, were Pd[(C$_6$H$_5$)$_3$P]$_4$ (48 mg.), (C$_6$H$_5$)$_3$P (55 mg.) and potassium ethyl hexanoate (4.17 ml. of 0.5M in ethyl acetate, 0.0021 mol). After stirring 4 hours, solids were recovered by filtration. These were repulped in 6 ml. ethyl acetate to yield purified title product, 0.74 g.; mp 211°-213° (decomposition); $^1$H-nmr (CDCl$_3$ with a few drops CD$_3$CN to achieve solution; 300 MHz) 1.55 (s, 3H), 1.75 (s, 3H), 4.15 (q, 1H), 4.4 (s, 1H), 5.65 (d, 1H), 7.6-7.8 (m, 2H), 8.1-8.2 (dd, 2H), 8.6 (s, 1H).

EXAMPLE D41

Potassium 6-beta-[S-1-Hydroxy-2-oxo-2-(2-phenyl-4-thiazolyl)ethyl]penicillanate

By the method of the preceding Example, the product of Example B24 (0.78 g.) was converted to present title product, 0.68 g.; mp 199°-201° (decomposition); $^1$H-nmr (300 MHz, D$_2$O) 1.45 (s, 3H), 1.6 (s, 3H), 4.1 (m, 1H), 4.3 (s, 1H), 5.4 (d, 1H), 5.5 (d, 1H), 7.3-7.5 (m, 3H), 7.65-7.75 (m, 2H), 8.4 (s, 1H).

EXAMPLE D42

Potassium
6-beta-[S-1-Hydroxy-2-(4-methylphenyl)-2-oxoethyl]-penicillanate

By the method of Example D40, the product of Example B25 (1.06 g., 0.0027 mol) was converted to present title product. In the final stage, the material filtered from ethyl acetate was taken up in 50 ml. of $H_2O$ and freeze dried to yield 0.79 g.; mp 229°–231° (decomposition); $^1$H-nmr (300 MHz, $D_2O$) 1.4 (s, 3H), 1.55 (s, 3H), 2.35 (s, 3H), 4.0 (q, 1H), 4.2 (s, 1H), 5.45 (2d, 2H), 7.35 (d, 2H), 7.85 (d, 2H).

EXAMPLE D43

Potassium
6-beta-[S-1-Hydroxy-2-(4-methoxycarbonylphenyl)-2-oxoethyl]penicillanate The product of Example B26 (0.39 g., 0.0009 mol) was converted to freeze-dried title product according to the preceding Example, 0.31 g.; $^1$H-nmr ($D_2O$, 300MHz) 1.45 (s, 3H), 1.65 (s, 3H), 3.95 (s, 3H), 4.1 (q, 1H), 4.25 (s, 1H), 5.5 (dd, 2H), 8.05–8.15 (dd, 4H).

EXAMPLE D44

Potassium
6-beta-[S-2-(4-cyanophenyl)-1-hydroxy-2-oxoethyl]-penicillanate

The product of Example B27 (0.75 g., 0.0019 mol) was converted to freeze-dried title product according to Example D42, 0.71 g.; m.p. 196°–198°.

EXAMPLE D45

Potassium
6-beta-(S-1-Hydroxy-2-oxo-3-methyl-3-phenoxybutyl)-penicillanate

The product of Example B28 (1.13 g., 2.52 mmol) was converted to title product according to Example D40, 0.77 g., solid, converted to freeze-dried product by dissolving in water and freeze-drying, 0.55 g.; m.p. 132°–135° C., $^1$H-nmr ($D_2O$) delta (ppm) 1.35 (s, 3H), 1.45 (s, 3H), 1.5 (s, 3H), 3.9 (q, 1H), 4.1 (s, 1H), 4.5 (s, 2H), 5.0 (d, 1H), 5.35 (d, 1H), 7.3–7.4 (m, 5H).

EXAMPLE D46

Potassium
6-beta-[S-1-Hydroxy-2-oxo-3,3-(spirocyclohexyl)-butyl]penicillanate

By the method of Example D42, the title product of Example B29 (1.59 g., 4.02 mmol) was converted to present freeze-dried title product, 1.41 g.; m.p. 249°–251° C. $^1$H-nmr ($D_2O$, 250MHz) 1.35 (s, 3H), 1.4–1.75 (m, 10H), 1.6 (s, 3H), 1.75 (s, 3H), 2.05–2.3 (br m, 1H), 4.0–4.1 (q, 1H), 4.3 (s, 1H), 5.5–5.15 (d, 1H), 5.6 (d, 1H).

EXAMPLE D47

Potassium
6-beta-[S-1-Hydroxy-2-oxo-2-(1-adamantyl)ethyl]-penicillanate

By the method of Example D42, the product of Example B30 (2.28 g., 5.26 mmol) was converted to present title product, 2.0 g.; m.p. 265°–267° (decomposition); $^1$H-nmr ($D_2O/CD_3CN$; 300MHz) 1.6 (s, 3H), 1.75 (s, 3H), 1.85–2.2 (multiplets, 15H), 4.05 (q, 1H), 4.3 (s, 1H), 5.15 (d, 1H), 5.5 (d, 1H).

EXAMPLE D48

Potassium
6-beta-[S-1-Hydroxy-2-oxo-2-(4-(hydroxymethyl)-phenyl)ethyl]penicillanate By the method of Example D40, the product of Example G4 (0.20 g., 0.493 mmol) was converted to title product, 0.176 g.; solid; $^1$H-nmr (300MHz) 1.45 (s, 3H), 1.6 (s, 3H), 4.05 (q, 1H), 4.25 (s, 1H), 4.7 (s, 2H), 5.5 (d, 1H), 5.55 (d, 1H), 7.5 (d, 2H), 8.0 (d, 2H).

EXAMPLE D49

Potassium
6-beta-[S-1-Hydroxy-2-oxo-2-(4-(1-hydroxy-1-methylethyl)phenyl)ethyl]penicillanate By the method of Example D40, the product of Example B32 (0.40 g., 0.92 mmol) was converted to present title product, 0.29 g.; m.p. 198°–199° C.; $^1$H-nmr ($D_2O$, 300MHz) 1.4 (s, 3H), 1.55 (s, 6H), 1.6 (s, 3H), 4.05 (q, 1H), 4.25 (s, 1H), 5.5 (d, 1H), 5.55 (d, 1H), 7.6 (d, 2H), 7.95 (d, 2H).

EXAMPLE D50

Potassium
6-beta-[S-1-Hydroxy-2-oxo-2-(4-(chloromethyl)phenyl)ethyl]penicillanate By the method of Example D40, the title product of Example B33 (0.125 g., 0.295 mmol) was converted to present title product, 0.11 g.; $^1$H-nmr ($D_2O$, 300MHz) 1.45 (s, 3H), 1.6 (s, 3H), 4.05 (q, 1H), 4.25 (s, 1H), 4.7 (s, 2H), 5.5 (overlapping doublets, 2H), 7.6 (d, 2H), 7.95 (d, 2H).

EXAMPLE D51

Sodium
6-beta-[S-1-Hydroxy-2-(N-methyl-3-indolyl)-2-oxoethyl]penicillanate

By the method of Example D35, S-title product of Example B34 (3.37 g., 7.86 mmol) was converted to present title product, 1.9 g.; $^1$H-nmr 1.38 (s, 3H), 1.57 (s, 3H), 3.64 (s, 3H), 4.05 (dd, 1H, J=4.0, 10Hz), 4.22 (s, 1H), 5.21 (d, 1H, J=10Hz), 5.39 (d, 1H, J=4.0Hz), 7.23 (m, 3H), 8.05 (m, 1H), 8.17 (s, 1H); ir (KBr) 1752, 1632, 1611 cm$^{-1}$.

EXAMPLE D52

Sodium
6-beta-[R-1-Hydroxy-2-(N-methyl-3-indolyl)-2-oxoethyl]penicillanate

By the method of Example D35, R-title product of Example B34 (3.65 g., 8.52 mmol) was converted to present title product, 2.96 g. This product was further purified by dissolving in 25 ml. each of water and ethyl acetate, adjusted to pH 8.5 with dilute NaOH with vigorous stirring, separating the layers, washing the aqueous layer with 1×25 ml. fresh ethyl acetate and 1×25 ml. 1:1 hexane:ether, adjusting the aqueous layer to 2.5 with dilute HCl, extracting the product into fresh ethyl acetate, extracting the product back into water at pH 8.0 and freeze-drying the aqueous, 1.93 g.; $^1$H-nmr 1.52 (s, 3H), 1.68 (s, 3H), 3.68 (s, 3H), 4.15 (m, 1H, obscured unresolved dd), 4.18 (s, 1H), 5.22 (d, 1H, J=10Hz), 5.48 (d, 1H, J=4.0Hz), 7.30 (m, 3H), 8.07 (m, 2H); ir (KBr) 1757, 1637, 1608 cm$^{-1}$.

EXAMPLE D53

Potassium 6-beta-[S-3-(Benzyloxycarbonylamino)-1-hydroxy-3-methyl-2-oxobutyl]penicillanate By the method of Example D40, but using 1:1 ethyl acetate:ether as solvent, the product of Example B35 (0.10 g., 0.2 mmol) was converted to present title product, 0.058 g.; $^1$H-nmr (D$_2$O) 1.42 (s, 3H), 1.43 (s, 3H), 1.48 (s, 3H), 1.53 (s, 3H), 3.90 (br s, 1H), 4.15 (s, 1H), 4.91 (d, 1H, J=6Hz), 5.08 (m, 2H), 5.36 (br s, 1H), 7.40 (s, 5H).

EXAMPLE D54

Potassium 6-beta-[S-1-Hydroxy-2-oxo-2-(4-(benzyloxycarbonylamino)phenyl)ethyl]penicillanate By the method of Example D53, the product of Example B36 (0.5 g., 0.95 mmol) was converted to present title product to present title product, 0.24 g.; $^1$H-nmr (D$_2$O) 1.59 (s, 3H), 1.75 (s, 3H), 4.16 (m, 1H), 4.37 (s, 1H), 5.28 (s, 2H), 5.60 (m, 2H), 7.46 (s, 1H), 7.64 (d, 2H, J=6Hz), 8.08 (d, 2H, J=6Hz); tlc Rf 0.45 (17:2:1 CHCl$_3$:CH$_3$OH:CH$_3$CO$_2$H).

EXAMPLE D55

Potassium 6-beta-6-[S-1-Hydroxy-2-oxo-2-(2-ethoxy-1-naphthyl)ethyl]penicillanate By the method of Example D53, the product of Example B37 (0.59 g., 1.2 mmol) was converted to present title product, 0.48 g.; $^1$H-nmr (D$_2$O) 1.19 (s, 3H), 1.27 (t, 3H, J=4Hz), 1.44 (s, 3H), 4.01 (m, 3H), 4.12 (s, 1H), 4.94 (d, 1H, J=3Hz), 5.42 (d, 1H, J=8Hz), 7.03 (d, 1H, J=4Hz), 7.24 (t, 1H, J=4Hz), 7.40 (t, 1H, J=4Hz), 7.52 (d, 1H, J=4Hz), 7.61 (d, 1H, J=4Hz), 7.67 (d, 1H, J=4Hz).

EXAMPLE D56

Potassium 6-beta-[S-1-Hydroxy-2-oxo-2(3-hydroxyphenyl)ethyl]penicillanate

By the method of Example D40, the product of Example B38 (44 mg., 0.112 mol) was converted to present title product, 31 mg.; $^1$H-nmr (D$_2$O) 1.47 (s, 1H), 1.64 (s, 3H), 4.08 (dd, 1H, J=4 and 8Hz), 4.27 (s, 1H), 5.51 (d, 1H, J=4Hz), 5.54 (d, 1H, J=8Hz), 7.18 (m, 1H), 7.49 (m, 3H).

EXAMPLE D57

Potassium 6-beta-[S-1-Hydroxy-2-oxo-2-(3-quinolyl)ethyl]penicillanate

By the method of Example D40, the product of Example B39 (41 mg., 0.095 mol) was converted to present title product, 31 mg.; $^1$H-nmr (D$_2$O) 1.50 (s, 3H), 1.67 (s, 3H), 4.15 (dd, 1H, J=4 and 8Hz), 4.30 (s, 1H), 5.60 (d, 1H, J=4Hz), 5.62 (d, 1H, J=8Hz), 7.67 (m, 1H), 7.94 (m, 3H), 8.87 (s, 1H), 9.11 (s, 1H); substantially identical with the product of Example D27.

EXAMPLE D58

Potassium 6-beta-[S-1-Hydroxy-2-oxo-2-(4-hydroxyphenyl)ethyl]penicillanate

By the method of Example D45, the product of Example B40 (0.11 g.) was converted to freeze-dried title product, 0.065 g.; $^1$H-nmr (D$_2$O) 1.46 (s, 3H), 1.64 (s, 3H), 4.07 (dd, 1H, J=4Hz, 4Hz), 4.26 (s, 1H), 5.47 (d, 1H, J=4Hz), 5.52 (d, 1H, J=8Hz), 6.88 (d, 2H, J=8Hz), 7.95 (d, 2H, J=8Hz).

EXAMPLE D59

Potassium 6-beta-[S-1-Hydroxy-2-oxo-2-(2-naphthyl)ethyl]penicillanate

By the method of Example D45, the product of Example B41 (1.08 g., 2.5 mmol) was converted to freeze-dried title product, 0.78 g.; $^1$H-nmr (D$_2$O) 1.43 (s, 3H), 1.62 (s, 3H), 4.13 (dd, 1H, J=4Hz, 4Hz), 4.26 (s, 1H), 5.01 (d, 1H, J=4Hz), 5.70 (d, 1H, J=10Hz), 7.67 (m, 2H), 7.98 (m, 4H), 8.62 (s, 1H).

METHOD E - HYDROGENOLYSIS

EXAMPLE E1

Sodium 6-beta-[R-1-Acetoxy-2-oxo-2-(phenyl)ethyl]penicillanate

Title product of Example C3 (150 mg.) and NaHCO$_3$ (0.8 equivalents) in 10 ml. 1:1 H$_2$O:CH$_3$OH was hydrogenated at atmospheric pressure over 250 mg. of prehydrogenated 10% Pd/C until uptake of hydrogen had ceased. The catalyst was recovered by filtration, the methanol stripped, and the aqueous residue extracted with ether and freeze dried to yield title product as a hydroscopic solid, 70 mg.; $^1$H-nmr (D$_2$O): 1.46 (s, 3H), 1.60 (s, 3H), 2.11 (s, 3H), 4.12 (s, 1H), 4.28 (dd, 1H, J=3.6, 9.6Hz), 5.44 (d, 1H, J=3.6Hz), 6.32 (d, 1H, J=9.6Hz), 7.56-8.01 (m, 5H).

By the same method substituting KHCO$_3$ for NaHCO$_3$, the title product of Example C2 is converted to the title product of Example D3.

EXAMPLE E2

6-beta-(S-3-Amino-1-hydroxy-3-methyl-2-oxobutyl)penicillanic Acid

5% Pd/diatomaceous earth (0.20 g. of 50% water wet) was slurried in 30 ml. 1:1 CH$_3$OH:H$_2$O, the pH adjusted to 4.5 with dilute HCl, and the mixture prehydrogenated for 15 minutes at atmospheric pressure. The product of Example D53 (0.10 g., 0.2 mmol) was taken up in 5 ml. CH$_3$OH, the pH adjusted to 4.5 with dilute HCl, the resulting solution added to the hydrogenated catalyst slurry, and the mixture hydrogenated at atmospheric pressure for 40 minutes. The catalyst was recovered by filtration, the filtrate stripped of THF and the aqueous residue freeze-dried to yield 0.085 g. of crude product. The latter was taken up in 15 ml. each of H$_2$O and ethyl acetate and the pH adjusted to 2.5. The aqueous phase was separated, extracted 3×15 ml. fresh ethyl acetate, adjusted to pH 5.15 and freeze-dried to yield purified title product, 0.035 g.; $^1$H-nmr (D$_2$O) 1.55 (s, 3H), 1.64 (s, 3H), 1.70 (s, 3H), 1.73 (s, 3H), 4.07 (dd, 1H, J=4 and 6Hz), 5.58 (s, 1H), 5.09 (d, 1H, J=6Hz), 5.56 (d, 1H, J=4Hz).

By methods well known for the acylation of 6-aminopenicillanic acid, the side chain amino group of the present product is acylated to form further useful N-formyl, N-(C$_2$–C$_5$)alkanoyl, N-benzoyl, N-phenoxyacetyl or N-phenylacetyl (optionally substituted on aromatic or aliphatic carbon with hydroxy or amino) derivatives.

EXAMPLE E3

Potassium 6-beta-[S-1-Hydroxy-2-oxo-2-(4-aminophenyl)ethyl]-penicillanate

5% Pd/C (0.10 g.) was prereduced with hydrogen at atmospheric pressure in 30 ml. 1:1 H$_2$O:CH$_3$OH for 15 minutes. The product of Example D54 (0.10 g.) was added and the mixture hydrogenated 2 hours at atmospheric pressure. Catalyst was recovered by filtration over diatomaceous earth, the filtrate was stripped of methanol and the aqueous residue freeze-dried to yield present title product, 0.066 g.; tlc Rf 0.28 (17:2:1 CHCl$_3$:CH$_3$OH:CH$_3$CO$_2$H); $^1$H-nmr (D$_2$O) 1.40 (s, 3H), 1.57 (s, 3H), 4.01 (m, 1H), 4.21 (s, 1H), 5.42 (m, 2H), 6.76 (d, 2H, J=6Hz), 7.82 (d, 2H, J=6Hz).

By methods well known in the art, as routinely employed in the acylation of 6-aminopenicillanic acid, the present product is acylated to form N-acyl derivatives, such as those enumerated in the preceding Example.

METHOD F - OXIDATION TO SULFOXIDE OR SULFONE

EXAMPLE F1

Allyl 6-beta-[S-1-Hydroxy-2-oxo-2-(phenyl)ethyl]penicillanate 1-alpha- and 1-beta-Oxide Under N$_2$, the S-epimer of Example B1 (0.43 g., 1.15 mmol) was dissolved in 4.3 ml. of CH$_2$Cl$_2$ and cooled to 0°. m-Chloroperbenzoic acid (85%, 0.227 g., 1.15 mmol) was added and the reaction maintained at 0° for 1.5 hours, then quenched with 4.3 ml. of saturated NaHCO$_3$ and 8.6 ml. of CH$_2$Cl$_2$. The aqueous layer was separated, washed 2×16 ml. saturated NaHCO$_3$ and 1×16 ml. brine, dried and evaporated to yield mixed title products as a solid foam, 420 mg., which was chromatographed on silica gel with 1:1 ethyl acetate:hexane as eluant to yield:

1-beta-oxide (lp), 100 mg.; tlc Rf 0.5 (1:1 ethyl acetate:hexane); ir (CHCl$_3$) cm$^{-1}$: 3400 (b), 2990 (w), 1790 (s), 1755 (s), 1685 (s), 1600 (w), 1585 (w), 1450 (m), 1375 (m), 1270 (s), 1050 (s); $^1$H-nmr: 1.22 (s, 3H), 1.65 (s, 3H), 4.09 (dd, 1H), 4.72 (s, 1H), 4.72 (m, 2H), 5.07 (d, 1H), 5.40 (m, 2H):, 5.95 (m, 1H), 6.10 (d, 1H), 7.39–8.08 (m, 5H).

1-alpha-oxide (mp), 130 mg; tlc Rf 0.15 (1:1 ethyl acetate:hexane); ir (CHCl$_3$) cm$^{-1}$: 3450 (b), 2990 (w), 1795 (s), 1755 (s), 1695 (s), 1600 (w), 1450 (w), 1270 (s); $^1$H-nmr 1.42 (s, 3H), 1.67 (s, 3H), 4.30 (m, 2H), 4.43 (s, 1H), 4.65 (m, 2H), 4.90 (d, 1H), 5.32 (m, 2H), 5.60 (dd, 1H), 5.9 (m, 1H), 7.51–8.02 (m, 5H).

EXAMPLE F2

Allyl 6-beta-[S-1-Hydroxy-2-oxo-2-(phenyl)ethyl]penicillanate 1,1-Dioxide

Using 2.2 molar equivalents of m-chloroperbenzoic acid, title product of Example B1 (0.25 g.) was converted to instant, chromatographed title product, 119 mg.; tlc Rf 0.8 (1:1 ethyl acetate:hexane); ir (CHCl$_3$) cm$^{-1}$: 3495 (b), 2998 (w), 1795 (s), 1770 (s), 1680 (s), 1605 (w), 1325 (m), 1200 (m); $^1$H-nmr: 1.44 (s, 3H), 1.58 (s, 3H), 3.22 (d, 1H), 4.15 (dd, 1H), 4.50 (s, 1H), 4.74 (m, 2H), 4.98 (d, 1H), 5.38 (m, 2H), 5.95 (m, 1H), 6.05 (dd, 1H), 7.45–8.10 (m, 5H).

EXAMPLE F3

Allyl 6-beta-[S-1-Hydroxy-2-oxo-2-(4-methoxyphenyl)ethyl]-penicillanate 1-alpha- and 1-beta-Oxide Under N$_2$, more polar, S-title product of Example B6 (0.329 g., 0.81 mmol) was dissolved in 10 ml. CH$_2$Cl$_2$ and treated with m-chloroperbenzoic acid (85%, 0.16 g., 0.81 mmol). After 40 minutes, the reaction mixture was diluted with 30 ml. fresh CH$_2$Cl$_2$, washed 2×20 ml. saturated NaHCO$_3$, dried over MgSO$_4$ and stripped to an oil, 310 mg. The latter was chromatographed on 35 g. silica gel using 1:1 ethyl acetate:hexane as eluant to yield title products as follows:

1-alpha-oxide (lp) 99 mg.; $^1$H-nmr; 1.23 (s, 3H), 1.65 (s, 3H), 3.58 (d, 1H), 3.85 (s, 3H), 4.06 (dd, 1H), 4.70 (s, 3H), 4.71 (d, 2H), 5.14 (d, 1H), 5.37 (m, 2H), 5.93 (m, 1H), 6.03 (dd, 1H), 6.90 (d, 2H), 8.05 (d, 2H).

1-beta-oxide (mp), 128 mg.; $^1$H-nmr; 1.42 (s, 3H), 1.65 (s, 3H), 3.90 (s, 3H), 4.30 (dd, 1H), 4.35 (d, 1H), 4.44 (s, 1H), 4.67 (d, 2H), 4.90 (d, 1H), 5.34 (m, 2H), 5.55 (dd, 1H), 5.91 (m, 1H), 7.00 (d, 2H), 7.96 (d, 2H).

EXAMPLE F4

Allyl 6-beta-[R-1-Hydroxy-2-oxo-2-(4-methoxyphenyl)ethyl]penicillanate 1-beta-Oxide Less polar R-title product of Example B6 (0.248 g., 0.61 mmol) was oxidized according to the preceding Example to yield crude product, 231 mg. The above title product (the more polar of the two 1-oxides) was isolated by chromatography on 20 g. silica gel with 1:1 hexane:ethyl acetate as eluant. Yield, 110.5 mg.; $^1$H-nmr; 1.26 (s, 3H), 1.70 (s, 3H), 3.85 (s, 3H), 4.04 (dd, 1H), 4.66 (d, 1H), 4.67 (s, 1H), 5.09 (d, 1H), 5.12 (d, 1H), 5.34 (m, 2H), 5.55 (dd, 1H), 5.92 (m, 1H), 6.95 (d, 2H), 8.10 (d, 2H).

METHOD G - ENOL ETHER HYDROLYSIS

EXAMPLE G1

Allyl 6-beta-(S-1-Hydroxy-2-oxo-3-phenylpropyl)penicillanate

Title product of Example B10 (either or both epimers, 0.127 g., 0276 mmol) was taken up in 8.28 ml. THF and stirred in an ice-water bath. HCl (0.1N, 276 mmol) was added slowly. The mixture was stirred at 0° for 1 hour, and at ambient temperature for 1.5 hours, then poured into 15 ml. saturated NaHCO$_3$ and extracted 1×15 ml. and 3×10 ml. of ether. The organic extracts were combined, dried and stripped to yield title product as an oil, 105 mg.; $^1$H-nmr; 1.46 (s, 3H), 1.64 (s, 3H), 3.47 (d[OH], 1H), 3.82 (dd, 1H), 3.99 (s, 2H), 4.45 (s, 1H), 4.66 (d, 2H), 4.73 (dd, 1H), 5.35 (m, 2H), 5.50 (d, 1H), 5.92 (m, 1H), 7.24 (m, 2H), 7.31 (m, 3H); ir (KBr) cm$^{-1}$ 3461 (b), 2929 (m), 1769 (s), 1750 (s), 1207 (m); ms (m/e): 91, 114, 200, 269, 298, 304, 389.

EXAMPLE G2

Allyl 6-beta-[S-1-Hydroxy-2-oxo-3-(2-thienyl)propyl]penicillanate

By the procedure of the preceding Example, title product of Example B11 (0.76 g., 0.0016 mol) was converted to instant title product as an oil, 0.74 g., chromatographed on 80 g. silica gel with 1:49 acetone:CHCl$_3$ as eluant to yield purified title product, 0.26 g.; tlc Rf 0.25 (1:49 acetone:CHCl$_3$); $^1$H-nmr; 1.48 (s, 3H), 1.67 (s, 3H), 3.33 (d[OH], 1H), 3.86 (dd, 1H), 4.23 (3, 2H), 4.46 (s, 1H), 4.67 (d, 2H), 4.77 (dd, 1H), 5.34 (m, 2H), 5.53 (d, 1H), 5.94 (m, 1H), 6.98 (m, 2H), 7.24 (m, 1H).

EXAMPLE G3

Allyl 6-beta-[S-1-Hydroxy-2-(4-hydroxyphenyl)-2-oxo]-penicillanate

Title product of Example B14 (98 mg., 0.23 mmol) was dissolved in 3 ml. 10:1 acetone:H$_2$O. With stirring, HgO (63 mg.) and then HgCl$_2$ (63 mg, 0.23 mmol) were added over 3 minutes. After 18 hours, 10 ml. of saturated KI and 10 ml. ethyl acetate were added. The aqueous layer was separated and washed 3×10 ml. fresh ethyl acetate. The four organic layers were combined, dried (MgSO$_4$), stripped to an oil and chromatographed on silica gel using 1:1 ethyl acetate:hexane as eluant to yield purified title product as a colorless oil, 25 mg.; $^1$H-nmr: 1.47 (s, 3H), 1.72 (s, 3H), 4.12 (m, 2H), 4.52 (s, 1H), 4.67 (m, 2H), 5.35 (m, 2H), 5.57 (d, 1H), 5.91 (m, 1H), 6.85 (d, 2H), 7.95 (d, 2H).

EXAMPLE G4

Allyl 6-beta-[S-1-Hydroxy-2-oxo-2-(4-(hydroxymethyl)-phenyl)ethyl]penicillanate

The title product of Example B31 (0.80 g., 1.54 mmol) in 3 ml. THF was cooled to 0°-5°. Glacial acetic acid (0.924 g., 0.881 ml., 15.4 mmol) was added by syringe over 3 minutes, followed by tetrabutyl ammonium fluoride (4.62 ml. of 1M in THF) over 10 minutes. The mixture was stirred 45 minutes at 0°-5° and 2 hours at room temperature, poured into 25 ml. H$_2$O and extracted 3×25 ml. H$_2$O, 2×25 ml. saturated NaHCO$_3$ and 1×25 ml. brine, dried and stripped to yield title product as a solid, 0.45 g.; tlc Rf 0.12 (1:1 hexane:ethyl acetate).

METHOD H - PREPARATION OF IN VIVO HYDROLYZABLE ESTERS

EXAMPLE H1

Pivaloyloxymethyl 6-beta-[S-1-Hydroxy-2-oxo-2-(2-thienyl)ethyl]penicillanate

Tetrabutylammonium hydrogen sulfate (0.374 g., 1.1 mmol) was dissolved in 2.5 ml. H$_2$O. NaHCO$_3$ (92 mg., 1.1 mmol) was added portionwise at a rate which controlled the foaming. Finally, title product of Example D10 (0.42 g., 1.1 mmol) was added. After about 30 minutes of stirring, the solution was extracted 4×5 ml. CHCl$_3$ and the combined extracts were dried and stripped to yield tetrabutylammonium 6-beta-[S-1-hydroxy-2-oxo-2-(2-thienyl)ethyl]penicillanate as a foam (about 350 mg.). Under nitrogen, this tetrabutylammonium salt was dissolved in 2 ml. acetone and chloromethyl pivalate (0.216 ml., 1.1 mmol) was added. After 24 hours, the acetone was stripped and the residue dissolved in 5 ml. ethyl acetate, washed 3×5 ml. water and 1×5 ml. brine, dried and restripped to an oil. The latter was chromatographed on silica gel with 1:1 ethyl acetate:hexane as eluant to yield purified title product as a dry foam, 121 mg.; tlc Rf 0.7 (1:1 ethyl acetate:hexane); $^1$H-nmr: 1.22 (s, 9H), 1.33 (s, 3H), 1.67 (s, 3H), 4.04 (dd, 1H), 4.49 (s, 1H), 6.25 (d, 1H), 5.57 (d, 1H), 5.83 (Abq, 2H), 7.18 (dd, 1H), 7.74 (dd, 1H), 8.07 (dd, 1H).

EXAMPLE H2

Pivaloyloxymethyl 6-beta-[S-1-Hydroxy-2-(N-methyl-2-indolyl)-2-oxoethyl]penicillanate The product of Example D37 (0.616 g., 0.0015 mol) was dissolved in 5 ml. DMF. Chloromethyl pivalate (0.218 ml., 0.0015 mol) and the mixture stirred for 16 hours, then diluted with 10 ml. each of H$_2$O and ethyl acetate, the pH adjusted to 7.0 and the organic layer separated washed 3×5 ml. H$_2$O and 1×5 ml. brine, dried and stripped to an oil, purified by chromatography on 13 g. silica gel with 7:1 CH$_2$Cl$_2$: ethyl acetate as eluant, 0.446 g.; tlc Rf 0.6 (7:1 CH$_2$Cl$_2$: ethyl acetate); $^1$H-nmr 1.22 (s, 9H), 1.49 (s, 3H), 1.71 (s, 3H), 4.08 (s, 3H), 4.12 (dd, 1H, J=4.3, 8.27), 4.50 (s, 1H), 5.39 (d, 1H, J=8.27), 5.54 (d, 1H, J=4.3), 5.82 (ABq, 2H, J=5.1), 7.46 (m, 5H).

EXAMPLE H3

Pivaloyloxymethyl 6-beta-[S-1-Hydroxy-2-(N-methyl-2-pyrrolyl)-2-oxoethyl]penicillanate By the method of the preceding Example, except to use 9:1 CH$_2$Cl$_2$: ethyl acetate as eluant on chromatography, the product of Example D29 (0.25 g., 0.007 mol) was converted to present title product, 118 mg.; $^1$H-nmr (250 MHz) 1.21 (s, 9H), 1.48 (s, 3H), 1.68 (s, 3H), 3.40 (br d, 1H, J=5.53), 3.94 (s, 3H), 4.03 (dd, 1H, J=4.67, 7.7), 4.47 (s, 1H), 5.17 (br dd, 1H, J=5.53, 7.7), 5.48 (d, 1H, J=4.67), 5.80 (ABq, 2H, J=5.45), 6.19 (m, 1H), 6.90 (m, 1H), 7.20 (m, 1H).

EXAMPLE H4

Pivaloyloxymethyl 6-beta-[S-1-Hydroxy-2-(4-methylphenyl)-2-oxoethyl]-penicillanate By the method of Example H1, title product of Example D42 (2.0 g., 0.0052 mol) was converted to present title product as an oil (2.15 g.) which was chromatographed on silica gel with 5:2 hexane:ethyl acetate as eluant form purified title product as a solid foam, 1.55 g.; mp 111°-113°; $^1$H-nmr (300 MHz) 1.15 (s, 9H), 1.4 (s, 3H), 1.65 (s, 3H), 2.35 (s, 3H), 3.95 (q, 1H), 4.4 (s, 1H), 5.35 (d, 1H), 5.45 (d, 1H), 5.75 (dd, 2H), 7.2 (d, 2H), 7.8 (d, 2H).

PREPARATION 1

Allyl 6,6-Dibromopenicillanate

Under nitrogen, 6,6-dibromopenicillanic acid (20.0 g., 55.7 mmol) was dissolved in 60 ml. DMF and cooled to 0° C. Triethylamine (7.74 ml.), NaHCO$_3$ (0.5 g.) and allyl bromide (4.5 ml.) were added sequentially to the cold solution. The reaction mixture was warmed, stirred 20 hours at ambient temperature, poured into 600 ml. ice and water, and extracted with 600 ml. ether. The organic extract was washed with brine, dried and evaporated to yield title product as a syrup, 18.0 g., tlc Rf 0.9 (1:1 ethyl acetate:hexane); $^1$H-nmr: 1.46 (s, 3H), 1.59 (s, 3H), 4.53 (s, 1H), 4.62 (m, 2H), 5.38 (m, 2H), 5.76 (s, 1H), 5.92 (m, 1H).

PREPARATION 2

Methyl 2-(2-Furyl)-2-oxoethyl Sulfoxide

DMSO (35 ml., dry, distilled from CaH$_2$) and NaH (3.08 g., 0.076 mol as a 60% suspension in oil) was heated under nitrogen until evolution of H$_2$ was complete, cooled to 0° C., and diluted with 35 ml. THF. Methyl furan-2-carboxylate (5 ml., 5.89 g., 0.047 mol) was added, the mixture warmed to ambient temperature, stirred 2 hours, poured into an equal volume of water, and extracted with one half volume of ether. The aqueous layer was adjusted to pH3 with 6N HCl and extracted 3×150 ml. CHCl$_3$. The CHCl$_3$ extracts were combined, dried and evaporated to an oil which crystallized on standing in vacuum. The latter was slurried in minimal 1:1 CHCl$_3$:hexane and recovered by filtration, 2.84 g.; tlc Rf 0.7 (3:1 ethyl acetate: methanol); $^1$H-nmr 2.75 (s, 3H), 4.21 (ABq, 2H), 6.58 (dd, 1H), 7.32 (d, 1H), 7.62 (d, 1H).

PREPARATION 3

2-(2-Furyl)-2-oxo-1-(methylthio)ethanol

A solution of title product of the preceding Preparation (1.0 g.) in 2 ml. DMSO, 0.75 ml. H$_2$O and 0.1 ml. 12N HCl was allowed to stand for 16 hours, by which time product began to crystallize. The mixture was diluted with 10 ml. water and extracted 2×15 ml. CHCl$_3$. The organic layers were combined, dried, evaporated to a syrup and crystallized from CHCl$_3$ and hexane, 0.6 g., tlc Rf 0.9 (3:1 ethyl acetate:methanol; $^1$H-nmr: 2.1 (s, 3H), 4.23 (d, 1H), 5.95 (d, 1H), 6.62 (dd, 1H), 7.42 (dd, 1H), 7.63 (m, 1H).

PREPARATION 4

(2-Furyl)glyoxal

To a solution of title product of the preceding Preparation (8.5 g., 0.049 mol) in 6:1 THF:H$_2$O (60 ml.) was added anhydrous CuSO$_4$ (9.0 g.) and sodium acetate (9.0 g.). A slight exotherm was noted and a bluegreen solution resulted. After one hour, precipitated solids were removed by filtrating with THF wash. The combined filtrate and wash was diluted with water and extracted 6×50 ml. CHCl$_3$ and 2×50 ml. ethyl acetate. All eight extracts were combined, dried and evaporated to yield 5 g. of crude title product, purified by distillation, 3.6 g.; bp 63°/0.5 mm.; tlc Rf 0.25 (1:1 ethyl acetate:hexane).

PREPARATION 5

Methyl 2-(4-Methoxyphenyl-2-oxoethyl Sulfide

Under nitrogen, sodium hydride (12 g., 0.5 mol, 20 g. of 60% suspension in oil) was washed 3×50 ml. hexane, added to dry DMSO (250 ml.) and heated at 67° for 2 hours. The resulting solution was cooled to −12° and methyl anisate (41.54 g., 0.25 mol) in 50 ml. THF added dropwise over 20 minutes. After warming to room temperature and holding for 2 hours, the reaction mixture was quenched into 200 ml. water, extracted with 3×100 ml. ether, acidified to pH 3 with 6NHCl, and extracted with 3×150 ml. CHCl$_3$. The CHCl$_3$ extracts were combined, dried and evaporated to yield title product as a powder, 70.2 g. (slightly wet), $^1$H-nmr: 2.72 (s, 3H), 3.80 (s, 3H), 4.42 (ABq, 2H), 7.01 (d, J=9Hz, 2H), 8.12 (d, J=9Hz, 2H).

PREPARATION 6

2-(4-Methoxyphenyl)-2-oxo-1-(methylthio)ethanol

Title product of the preceding Preparation (70.2 g.) was dissolved in 100 ml. DMSO, diluted with water (750 ml.), and treated with 100 ml. 12N HCl. After stirring 18 hours, title product was recovered by filtration, 39.8 g.; $^1$H-nmr: 2.00 (s, 3H), 3.91 (s, 3H), 4.33 (bs, 1H), 6.15 (s, 1H), 7.01 (d, J=9Hz, 2H), 8.12 (d, J=9Hz, 2H).

PREPARATION 7

(4-Methoxyphenyl)glyoxal Monohydrate

Title product of the preceding Preparation (39.8 g., 0.187 mol) was dissolved with warming in 200 ml. CHCl$_3$. With vigorous stirring Cupric acetate monohydrate (28.15 g., 0.141 mol) was added in one portion. The reaction mixture was stirred for 1 hour, then filtered with 3×75 ml. of CHCl$_3$ wash. The filtrate and CHCl$_3$ washes were combined and extracted with 100 ml. water. The water layer was separated, neutralized with K$_2$CO$_3$ (about 2 g. was required), recombined and equilibrated with the organic layer, reseparated and extracted with 4×30 ml. CHCl$_3$. The equilibrated organic layer and CHCl$_3$ extracts were combined, dried over MgSO$_4$ and evaporated to yield title product as a semisolid, 36.5 g.

PREPARATION 8

Methyl 2-(2-Thienyl)-2-oxoethyl Sulfoxide

Except to extract product into CH$_2$Cl$_2$ at pH 2.8, the method of Preparation 5 was used to covert methyl thiophene-2-carboxylate (27.5 g., 0.193 mol) into instant title product, an oil which was crystallized by slurrying in ether, 195. g.; $^1$H-nmr: 2.75 (s, 3H), 4.30 (s, 2H), 7.05 (m, 1H), 7.80 (m, 2H).

PREPARATION 9

2-(2-Thienyl)-2-oxo-1-(methylthio)ethanol

Title product of the preceding Preparation (19.5 g.) was dissolved in 38 ml. DMSO, 14 ml. water and 1.95 ml. 12N HCl, allowed to stand 18 hours, poured into 500 ml. water, and title product recovered by filtration, 14 g.; $^1$H-nmr: 2.05 (s, 3H), 4.30 (d, 1H), 5.90 (d, 1H), 7.15 (m, 1H), 7.90 (m, 1H).

PREPARATION 10

(2-Thienyl)glyoxal

By the method of Preparation 7, title product of the preceding Preparation (3.3 g.) was converted to the hydrate of instant title product as a liquid, 2.3 g., distilled under vacuum using a short path distillation head to yield title product as a low melting solid, 1.9 g., tlc Rf 0.3 (1:1 ethyl acetate:hexane).

PREPARATION 11

Methyl 2-(1-Naphthyl)-2-oxoethyl Sulfoxide

Except to adjust the pH to 1.5 with concentrated HCl, and to wash the CHCl$_3$ extracts 2×100 ml. saturated NaHCO$_3$ prior to drying, methyl naphthyl-1-carboxylate (25.0 g., 0.134 mol) was converted to instant title product as an oil, 35.5 g.; $^1$H-nmr: 2.85 (s, 3H), 4.58 (s, 3H), 7.4–8.80 (m, 7H).

PREPARATION 12

2-(1-Naphthyl)-2-oxo-1-(methylthio)ethanol

Title product of the preceding Preparation (35.5 g.) was converted to present title product. The water washed wet cake was taken up in CHCl$_3$, separated from the aqueous phase, dried over MgSO$_4$ and stripped to yield purified title product as a powder, 26.8 g.; $^1$H-nmr: 2.05 (s, 3H), 4.68 (d, 1H), 6.25 (d, 2H), 7.4–8.82 (m, 7H).

PREPARATION 13

(1-Naphthyl)glyoxal

By the method of Preparation 7, title product of the preceding Preparation was converted to yield the hydrate of title product as a syrup, 22.4 g. The latter, 10 g., was distilled at 147°/0.4 mm. to yield title product, 5.1 g., as an oil.

PREPARATION 14

Phenylglyoxal

For use in the present syntheses, title product was freshly prepared by cracking N-(2-phenyl-2-oxo-1-hydroxyethyl)benzamide in a bath at 150° C. under high vacuum using a short path distillation head and a tared receiver.

PREPARATION 15

3-[1-(Ethoxy)ethoxy]-1-propene

Allyl alcohol (46.8 ml. 40 g., 0.69 mol) and ethyl vinyl ether (98.8 ml., 74.5 g., 1.033 mols) were stirred together at −12°. dl-Camphorsulfonic acid (150 mg.) was added acid and stirring continued for 3 hours at that temperature. The mixture was then washed 1×100 ml. saturated NaHCO$_3$, 1×100 ml. brine, dried and stripped to yield title product as an oil (100 ml., essentially quantitative yield). $^1$H-nmr 1.14 (t, 3H), 1.29 (d, 3H), 3.56 (dp, 2H), 4.06 (m, 2H), 4.75 (q, 1H), 5.26 (m, 2H), 5.99 (m, 1H).

PREPARATION 16

2-[1-(Ethoxy)ethoxy]acetaldehyde

3-[1-(Ethoxy)ethoxy]-1-propene (40 g., 0.0307 mol) was stirred in 100 ml. methanol at −78° for 5.5 hours as O$_3$ was through the solution. The resulting pale blue solution was purged with H$_2$, dimethyl sulfide (34 ml., 43.4 g., 0.68 mol) was added, and the mixture warmed to room temperature over 45 minutes. K$_2$CO$_3$ (0.2 g.) was added, the reaction mixture stripped of solvent, and the residue diluted with 1:1 water:ether. The aqueous layer was separated, diluted with brine and extracted with fresh ether. The organic layers were combined, dried and stripped to yield title product as an oil, 15.25 g., $^1$H-nmr: 1.24 (t, 3H), 1.37 (d, 3H), 3.50 (s, 2H), 3.61 (m, 2H), 4.81 (m, 1H), 9.87 (s, 1H).

PREPARATION 17

2-[1-(Ethoxy)ethoxy]-3-phenylpropenal

Benzaldehyde (4.2 ml., 4.41 g., 0.0416 mol) was stirred at 0° in a mixture of 150 ml. CH$_3$OH, 54 ml. H$_2$O and 42 ml. 10% NaOH. Title product of the preceding Example (5.00 g., 0.038 mol) was added slowly and the mixture stirred at ambient temperature for 16 hours, then extracted with 3×200 ml. hexane. The organic layers were combined, dried, and stripped to an oil (4.78 g.) which was chromatographed on 450 g. silica gel with 7:1 hexane:ether as eluant to yield purified title product, 2.75 g., $^1$H-nmr: 1.10 (t, 3H), 1.49 (d, 3H), 3.68 (m, 2H), 5.78 (q, 1H), 6.66 (s, 1H), 7.46 (m, 3H), 8.00 (m, 2H), 9.46 (s, 1H).

PREPARATION 18

2-[1-(Ethoxy)ethoxy]-3-(2-thienyl)propenal

Except to use a reaction time of 36 hours at ambient temperature, and to use toluene as eluant on chromatography, thiophene-2-carbaldehyde (3.1 ml., 3.74 g., 0.083 mol) and 2-[1-(ethoxy)ethoxy]acetaldehyde (4.0 g., 0.030 mol) were converted to instant title product as a yellow solid 1.39 g., crystallized from hexane, 109 mg.; $^1$H-nmr: 1.14 (t, 3H), 1.52 (d, 3H), 3.75 (m, 2H), 6.01 (q, 1H), 6.99 (s, 1H), 7.15 (m, 1H), 7.53 (m, 2H), 9.40 (s, 1H).

PREPARATION 19

Methyl p-Dimethylaminobenzoate p-Dimethylaminobenzoic acid (50 g.) and concentrated H$_2$SO$_4$ (25 ml.) in 350 ml. methanol were refluxed 18 hours. The reaction mixture was cooled, quenched with ice and water (350 ml.), neutralized portionwise with KHCO$_3$ until foaming ceased, and extracted 3×200 ml. CHCl$_3$. The organic layers were combined, washed 1×150 ml. brine, dried (MgSO$_4$) and reduced in volume to yield crystalline title product, 52 g.; $^1$H-nmr: 3.02 (s, 6H), 3.87 (s, 3H), 6.66 (d, J=16Hz, 2H), 7.95 (d, J=16Hz, 2H).

PREPARATION 20

Methyl 2-(4-Dimethylaminophenyl)-2-oxoethyl Sulfoxide

Except to carry out the CHCl$_3$ extraction at pH 5.0, the method of Preparation 5 was employed to convert title product of the preceding Preparation (52.8 g., 0.25 mol) into above title product as white crystals 41.1 g.; tlc Rf 0.5 (4:1 ethyl acetate:methanol) $^1$H-nmr: 2.70 (s, 3H), 3.0 (s, 6H), 4.30 (ABq, 2H) 6,67 (d, 2H), 7.85 (d, 2H).

PREPARATION 21

2-(4-Dimethylaminophenyl)-2-oxo-1-(methylthio)ethanol

Except that the pH was adjusted to 8.2 with 4N NaOH prior to initial recovery, the method of Preparation 6 was used to convert title product of the preceding Preparation (41.1 g., 0.18 mol) to present title. The resulting water washed, wet cake was taken up in excess CHCl$_3$ and separated from the aqueous phase. The organic phase was stripped to yield title product, 40.2 g., used without characterization in the next step.

PREPARATION 22

(4-Dimethylaminophenyl)glyoxal Monohydrate

By the method of Preparation 7, title product of the preceding Preparation (19.17 g., 0.085 mol) was converted to instant title product, 11.6 g., used without characterization in the procedure of Example A10.

PREPARATION 23

Methyl 2-(4-Fluorophenyl)-2-oxoethyl Sulfoxide

Except to CH$_2$Cl$_2$ for extraction, to backwash the combined extracts 1×100 ml. saturated NaHCO$_3$, the method of Preparation 5 was used to convert ethyl p-fluorobenzoate (20 g., 0.12 mol) to instant title product, crystallized by trituration with ether, 13.7 g.; mp 94.5°–96°; $^1$H-nmr: 2.75 (s, 3H), 4.33 (s, 2H), 7.15 (m, 2H), 8.02 (m, 2H).

PREPARATION 24

2-(4-Fluorophenyl)-2-oxo-1-(methylthio)ethanol

Title product of the preceding Preparation (15.2 g., 0.076 mol) was dissolved in 26.5 ml. DMSO and diluted with 9.9 ml. H$_2$O. Concentrated HCl (1.35 ml.) was added and the mixture stirred 20 hours, then poured into an equal volume of water and extracted 4×50 ml. CH$_2$Cl$_2$. The organic layers were combined, backwashed 1×50 ml. H$_2$O, dried and stripped to yield instant title product as an oil which crystallized on standing, 14.3 g.; $^1$H-nmr: 2.20 (s, 3H), 4.31 (d, 1H), 6.03 (d, 1H), 7.12 (m, 2H), 8.05 (m, 2H).

PREPARATION 25

(4-Fluorophenyl)glyoxal

By the method of Preparation 7, title product of the preceding Preparation (14.3 g.) was converted to (4-fluorophenyl)glyoxal hydrate, dehydrated to the instant title product by vacuum distillation, 6.0 g.; bp 77°–78°/4.5 mm.; $^1$H-nmr: 7.15 (m, 2H), 8.23 (m, 2H), 9.60 (s, 1H).

PREPARATION 26

Methyl 4-(Allyloxy)benzoate

NaH (60% in oil, 10 g., 0.25 mol) was washed 3×100 ml. hexane in place. 350 ml. DMF was then added, the mixture stirred under N$_2$, and methyl 4-hydroxybenzoate (38.0 g., 0.25 mol) added portionwise over 20 minutes as H$_2$ evolved. Allyl bromide (21.6 ml., 0.25 mol) was then added via syringe over 5 minutes. After 40 minutes additional stirring, the reaction mixture was poured into 400 ml. ice and water and 150 ml. ether was added. The layers were separated and the aqueous layer extracted 4×150 ml. fresh ether and 1×100 ml. hexane. The organic layers were combined, washed 2×150 ml. saturated NaHCO$_3$, dried over MgSO$_4$, and stripped to yield title product, 47.6 g.; 3.89 (s, 3H), 4.60 (m, 2H), 5.46 (m, 2H), 6.1 (m, 1H), 6.99 (d, 2H), 8.10 (d, 2H).

PREPARATION 27

Methyl 2-[4-(Propenyloxy)phenyl]-2-oxoethyl Sulfoxide

By the method of Preparation B5, title product of the preceding Preparation (47.6 g., 0.25 mol) was converted to instant title product, initially isolated as a semisolid which was crystallized from CHCl$_3$-hexane, 29.6 g.; $^1$H-nmr: 1.69 (dd, 3H), 2.70 (s, 3H), 4.40 (ABq, 2H), 5.10 (m, 1H), 6.60 (m, 1H), 7.10 (d, 2H), 8.05 (d, 2H). It was noted that the allyl group rearranged to a propenyl group during this process.

PREPARATION 28

2-[4-(Propenyloxy)phenyl]-2-oxo-1-(methylthio)ethanol

By the method of Preparation 6 title product of the preceding Preparation (29.6 g., 0.124 mol) was converted to instant title product, initially dispersed as an oil in the reaction mixture. Methanol just sufficient to dissolve the oil was added, followed by dropwise addition of water to the cloud point. The instant title product crystallized on standing 8.4 g.; $^1$H-nmr: 1.8 (dd, 3H), 2.1 (s, 3H), 4.70 (m, 1H), 5.2 (m, 1H), 6.25 (m, 1H), 7.2 (d, 2H), 8.2 (d, 2H).

PREPARATION 29

[4-(Propenyloxy)phenyl]glyoxal

According to the method of Preparation 25, title product of the preceding Preparation (4.8 g., 0.020 mol) was converted to instant title product, 2.78 g.; bp 180°/3 torr.

PREPARATION 30

(3-Thienyl)glyoxal

3-Acetylthiophene (20.0 g., 0.159 mol) and SeO$_2$ (19.4 g., 0.175 mol) were dissolved 100 ml. dioxane and 8 ml. H$_2$O by warming to 35°, then heated at reflux 16 hours. The reaction mixture was cooled, filtered and the filtrate stripped to a sludge (the hydrate of title product in crude form). The latter was distilled at reduced pressure to yield title product contaminated with about 10% starting material, 8.53 g.; tlc (5:3 hexane:ethyl acetate) Rf 0.27 (title product) and 0.59 (3-acetylthiophene). The latter was chromatographed on silica gel with 5:3 hexane:ethyl acetate as eluant. Clean product fractions were combined stripped to a solid, triturated with hexane, filtered and the solids (5.60 g.) sublimed to yield purified title product, 3.20 g.; tlc Rf 0.27 as above; sublimation point 70°/1 mm; ms: parent 141, base 111.

PREPARATION 31

Methyl 1-Methylpyrrole-2-carboxylate

To 1-methylpyrrole-2-carboxylic acid (28.66 g., 0.229 mol) in 75 ml. DMF at 0° was added N-ethyl diisopropylamine (39.4 ml., 0.229 mol) followed by CH$_3$I (14.27 ml., 0.229 mol). The reaction mixture was stirred 16 hours at room temperature, diluted with equal volumes each of ethyl acetate and water, the pH adjusted from 3.4 to 8.5, and the layers separated. The aqueous layer was washed 1×100 ml. fresh ethyl combined, washed 2×100 ml. H$_2$O and 1×100 ml. brine, dried over Na$_2$SO$_4$ and stripped to yield title product as an oil, 24.83 g.; $^1$H-nmr (CDCl$_3$) delta 3.75 (s, 3H), 3.87 (s, 3H), 5.97 (m, 1H), 6.62 (m, 1H), 6.78 (m, 1H).

PREPARATION 32

Methyl 2-(1-Methyl-2-pyrrolyl)-2-oxoethyl Sulfoxide

By the procedure of Preparation 5, using CH$_2$Cl$_2$ for extraction, title product of the preceding Preparation (24.83 g., 0.178 mol) was converted to instant title product, an oil which crystallized on standing in the refrigerator, 21.64 g.; mp 74°–76°; $^1$H-nmr (CDCl$_3$) delta: 2.73 (s, 3H), 3.92 (s, 3H), 4.10 (ABq, J=13Hz, 2H), 6.12 (m, 1H), 6.82 (m, 1H), 6.97 (m, 1H).

PREPARATION 33

1-Methyl-2-[2-hydroxy-2-(methylthio)acetyl]pyrrole

Title product of the preceding Preparation (21.63, 0.117 mol) was stirred with DMSO (40.9 ml.), H$_2$O (14.56 ml.) and 8N HCl (2.078 ml., 0.26 mol) for 16 hours, poured into equal volumes each of water and CH$_2$Cl$_2$, the pH adjusted to 8.5 with dilute NaOH and the layers separated. The aqueous layer was washed 3×50 ml. CH$_2$Cl$_2$. The organic layers were combined, washed 2 25 ml. H$_2$O, dried over Na$_2$SO$_4$ and stripped to yield title product, 16.62 g.; $^1$H-nmr (CDCl$_3$) delta: 2.17 (s, 3H), 3.95 (s, 3H), 5.80 (s, 1H), 6.10 (m, 1H), 6.83 (m, 1H), 7.05 (m, 1H).

PREPARATION 34

(1-Methyl-2-pyrrolyl)glyoxal)

Title product of the preceding Preparation (16.62 g., 0.090 mol) and cupric acetate hydrate (13.43 g., 0.067 mol) were combined in 80 ml. CHCl$_3$. After stirring 1.5 hours, the mixture was filtered and the filtrate wash 1×40 ml. saturated NaHCO$_3$ and 1×40 ml. H$_2$O, dried over Na$_2$SO$_4$, stripped and the residue distilled to yield title product, 2.03 g.; bp $^1$H-nmr (CDCl$_3$) delta: 3.98 (s, 1H), 6.18 80°-84°/2.4 mm; (m, 1H), 6.95 (m, 1H), 7.45 (m, 1H), 9.60 (s, 1H).

PREPARATION 35

Methyl Pyrrole-2-carboxylate

To pyrrole-2-carboxylic acid (1.11 g., 0.010 mol) in 5 ml. DMF at 0° was added N-(ethyl)diisopropylamine (1.806 ml., 0.0105 mol) followed by methyl iodide (0.654 ml., 0.0105 mol). The mixture was stirred 18 hours at room temperature, diluted with 10 ml. ethyl acetate and 10 ml. H$_2$O, the pH adjusted to 8.5, and the organic layer separated, washed 1×10 ml. H$_2$O, dried over Na$_2$SO$_4$, and stripped with CHCl$_3$ chase to yield title product as a gummy solid containing 10% DMF, 0.93 g.; $^1$H-nmr (CDCl$_3$) delta (narrow product peaks only): 3.80 (s, 3H), 6.15 (m, 1H), 6.83 (m, 2H).

PREPARATION 36

Methyl 1-Benzylpyrrole-2-carboxylate

Title product of the preceding Example (19.87 g., 0.159 mol) was dissolved in 200 ml. THF at 0°. NaH (7.622 g. of 50% in oil, 0.159 mol) was added portionwise so as to control foaming, followed by benzyl bromide (18.9 ml., 0.159 mol) and NaI (0.6 g.). The reaction was stirred 9 days at room temperature, then poured to equal volumes each of ethyl acetate and H$_2$O, the pH adjusted to 8.5 with dilute HCl, the aqueous layer separated and extracted with 200 ml. ethyl acetate, the organic layers combined and washed 2×100 ml. of H$_2$O, dried over Na$_2$SO$_4$, stripped and the residue chromatographed on silica gel (1:1 CH$_2$Cl$_2$:hexane as eluant) to yield purified title product, 22 g.; tlc Rf 0.3 (1:1 CH$_2$Cl$_2$:hexane); $^1$H-nmr (CDCl$_3$) delta: 3.80 (s, 3H), 5.60 (s, 2H), 6.20 (m, 1H), 7.13 (m, 7H).

PREPARATION 37

Methyl 2-(1-Benzyl-2-pyrrolyl)-2-oxoethyl Sulfoxide

Sodium hydride (9.95 g. of 50% in oil, 0.207 mol) was washed twice with hexane, warmed at 70° in DMSO 80 ml.) until hydrogen evolution had ceased (1 to 1.5 hours), cooled to −15° and diluted with 80 ml. THF. Maintaining −5 to +5°, title product of the preceding Preparation (22.31 g., 0.104 mol) was added portionwise. The reaction mixture was then stirred at room temperature 0.5 hour, poured into 160 ml. ice water, extracted 2×100 150 ml. ether, adjusted to pH with dilute HCl, and extracted 5×150 ml. CH$_2$Cl$_2$. The CH$_2$Cl$_2$ extracts were combined, washed 1×200 ml. saturated NaHCO$_3$, dried over Na$_2$SO$_4$ and stripped to yield title product, 19.36 g.; mp 95°-97°; tlc Rf 0.2 (ethyl acetate); $^1$H-nmr (CDCl$_3$) delta: 2.6 (s, 3H), 4.17 (ABq, 2H, J=13 Hz), 5.58 (s, 2H), 6.30 (m, 1H, 7.20 (m, 7H).

PREPARATION 38

1-Benzyl-2-[2-hydroxy-2-(methylthio)acetyl]pyrrole

By the method of Preparation 33, title product of the preceding Preparation (19.4 g., 0.074) was converted to instant title product, 19.2 g.; $^1$H-nmr (CDCl$_3$) delta: 1.83 (s, 1H), 5.48 (s, 2H), 5.75 (s, 1H), 6.15 (m, 1H), 7.03 (m, 7H).

PREPARATION 39

(1-Benzyl-2-pyrrolyl)glyoxal

By the method of Preparation 34, title product of the preceding Preparation was reacted to yield distilled title product, 9.1 g.; bp 134°-140°/0.3 mm; $^1$H-nmr (CDCl$_3$) delta: 5.60 (s, 2H), 6.20 (m, 1H), 7.10 (m, 6H), 7.48 (m, 1H), 9.50 (s, 1H).

PREPARATION 40

(2-Methoxyphenyl)glyoxal

SeO$_2$ (12.4 g., 0.112 mol) was dissolved in 75 ml. of 95% ethanol by warming to 55°. o-Methoxyacetophenone (15.3 g., 0.102 mol) was added in one portion and the mixture refluxed 21 hours. The reaction mixture was treated with activated carbon, filtered over diatomaceous earth, and the filtrate stripped to yield to an oil, 23.2 g. The latter was distilled to yield purified title product, 8.4 g., bp 94°-96°/0.5 mm, which solidified on cooling.

PREPARATION 41

(t-Butyl)glyoxal

SeO$_2$ (23.18 g., 0.21 mol) was dissolved by warming in C$_2$H$_5$OH (60 ml.) containing H$_2$O (3.76 g., 0.21 mol). t-Butylmethyl ketone (24.8 ml., 0.20 mol) was added and the mixture refluxed for 20 hours, cooled, filtered over diatomaceous earth, and stripped with toluene chase. The residue was distributed between 50 ml. each of CHCl$_3$ and H$_2$O (the pH was 2.6). The organic layer was separated, extracted 1×50 saturated NaHCO$_3$, 1×50 ml. H$_2$O and 1×50 ml. brine, dried by passing over a column of Na$_2$SO$_4$ and stripped to an oil. The latter was taken up in 50 ml. toluene, stirred for 5 hours with 4A-type molecular sieves, filtered, stripped and the residue distilled and redistilled to yield title product, 7.85 g.; bp 109°-111° C.; $^1$H-nmr 1.27 (s, 9H), 9.27 (s, 1H).

PREPARATION 42

(N-Methyl-2-indolyl)glyoxal

By the method of Preparations 4 to 6, methyl N-methylindole-2-carboxylate was converted, 2-(N-methyl-2-indolyl)-2-oxo-1-(methylthio)ethanol. The latter (31.21 g., 0.13 mol) was converted to present title product according to Preparation 7, except that the combined filtrate and CHCl$_3$ washes was simply washed 1×120 ml. saturated NaHCO$_3$ and 1×120 ml. H$_2$O, dried and stripped to an oil which was chromatographed on silica gel with 4:1 CH$_2$Cl$_2$:ethyl acetate as eluant to yield purified hydrate of title product as an oil. On distillation (bp 130°/0.65) title product was obtained as a solid, 10.5 g.; $^1$H-nmr 4.06 (s, 3H), 7.45 (m, 5H), 9.57 (s, 1H).

(N-Methyl-3-indolyl)glyoxal was prepared by the same methods. The hydrate showed $^1$H-nmr 4.03 (s, 3H), 7.28 (m, 5H). The hydrate was converted to the anhydrous form by heating at 140° and 1.2 mm for 1 hour. It showed $^1$H-nmr 4.06 (s, 3H), 7.45 (m, 5H), and 9.57 (s, 1H).

PREPARATION 43

2-(Dimethoxyacetyl)benzothiophene

A solution of benzothiophene (7.11 g., 0.053 mol) in 120 ml. dry THF was cooled to 0°. Butyl lithium (35.3 ml. of 1.5 M in hexane, 0.053 mol) was added dropwise, maintaining 0°-5°, and the mixture then warmed to ambient temperature for 1.25 hours, cooled to −75° C. and N-(dimethoxyacetyl)morpholine (10.0 g., 0.053 mol) in 50 ml. dry THF added dropwise maintaining −75° to −70°. The reaction was quenched by adding to 300 ml. saturated NH$_4$Cl and 300 ml. ether. The organic layer was separated, washed with brine, dried over MgSO$_4$ and stripped to an oil, 14 g., which was distilled to yield purified title product, 8.00 g.; bp 137°–139°/0.25 mm.; tlc Rf 0.23 (6:1 hexane:ethyl acetate), 0.47 (2:1 hexane:ethyl acetate); $^1$H-nmr 3.6 (s, 6H), 5.2 (s, 1H), 7.3–7.6 (m, 2H), 7.8–8.05 (m, 2H), 8.4 (s, 1H), tlc Rf 0.31 (4:1 hexane:ethyl acetate), 0.47 (2:1 hexane:ethyl acetate).

PREPARATION 44

(2-Benzothienyl)glyoxal

The product of the preceding Example (8.0 g.) was heated to 85° for 2 hours in 130 ml. 6N HCl, then cooled, and extracted 2×100 ml. ethyl acetate. The organic layers were combined, washed 3×100 ml. saturated NaHCO$_3$ and 1×100 ml. brine, dried over MgSO$_4$ and stripped to yield 7.3 g. of hydrated title product which was dehydrated by heating (and melting) under high vacuum at 110° C. to yield about 6.5 g. of title product.

PREPARATION 45

(1-Methyl-2-imidazolyl)glyoxal

By the method of Preparation 41, 1-methyl-2-acetylimidazole was converted to present title product. The hydrate (200 mg.) was sublimed from a bath at 100°-110° C. at 0.2 mm to yield 97 mg. of title product; $^1$H-nmr 4.03 (s, 3H), 7.32 (s, 1H), 7.63 (s, 1H), 10.33 (s, 1H),; tlc Rf 0.16 (2:1 hexane:ethyl acetate).

PREPARATION 46

(2-Phenyl-4-thiazolyl)glyoxal

4-Acetyl-2-phenylthiazole (16.9 g., 0.083 mol) was dissolved in a mixture of 165 ml. CH$_3$CO$_2$H and 65 ml. H$_2$O by warming to 50°. SeO$_2$ (19.4 g., 0.175 mol) was added and the mixture refluxed for 3 hours, then decolorized with activated carbon, filtered, the filtrate concentrated to an oil, the residue taken up in 600 ml. ethyl acetate, washed 2×300 ml. saturated NaHCO$_3$ and 1×300 ml. brine, and stripped to solids (crude hydrate), 16.2 g. The latter (6 g.) was heated to melting (155°) in vacuo for 10 minutes and cooled to yield title product as a glass; $^1$H-nmr 7.4–7.7 (m, 3H), 7.9–8.2 (m, 2H), 8.8 (s, 1H), 9.9 (s, 1H).

PREPARATION 47

4-(Dimethoxyacetyl)toluene

By the method of Preparation 43, 4-iodotoluene (11.5 g, 0.053 mol) was converted to distilled title product, 6.05 g.; bp 78°-80°/0.2 mm; $^1$H-nmr 2.45 (s, 3H), 3.5 (s, 6H), 5.2 (s, 1H), 7.2–7.3 (d, 2H), 8.0–8.1 (d, 2H).

PREPARATION 48

(4-Methylphenyl)glyoxal Hydrate

By the method of Preparation 44, the product of the preceding Preparation (5.9 g.) was converted to title product, 3.8 g., dehydrated by distillation just before use in the next step (Example A22).

PREPARATION 49

Methyl 4-Acetylbenzoate

4-Acetylbenzoic acid (12.7 g., 0.077 mol) was dissolved in 750 ml. methanol. Concentrated H$_2$SO$_4$ (1.6 ml.) was added and the mixture heated at 70° for 8 hours, cooled, stripped solids, taken up in 400 ml. ether, washed 3×150 ml. saturated NaHCO$_3$ and 1×150 ml. brine, dried over MgSO$_4$ and stripped to yield title product, 12.9 g.; tlc Rf 0.46 (2:1 hexane:ethyl acetate).

PREPARATION 50

(4-Methoxycarbonylphenyl)glyoxal Hydrate

The product of the preceding Example (12.4 g., 0.070 mol) and SeO$_2$ (19.3 g., 0.174 mol) were refluxed (about 110° C.) in a mixture of 100 ml. dioxane and 14 ml. H$_2$O for 16.5 hours. The hot solution was filtered over diatomaceous earth and the filtrate stripped to a mushy solid, which was crystallized from 500 ml. hot 3:7 THF:H$_2$O to yield purified title product, 9.06 g.; mp 127°–131° C.

PREPARATION 51

(4-Cyanophenyl)glyoxal Hydrate

By the method of the preceding Preparation, 4-cyanoacetophenone (15.0 g., 0.103 mol) was converted to crude title product. The latter was taken up in hot ethyl acetate, filtered, the filtrate stripped and title product crystallized from hot water saturated with benzene, 13.9 g.

PREPARATION 52

Methyl 2-Benzyloxy-2-methylpropionate

2-Benzyloxy-2-methylpropionic acid (4.4 g., 0.0023 mol) was dissolved in 50 ml. of methanol treated with acetyl chloride (1.61 ml., 1.78 g., 0.0023 mol), stirred for 16 hours, stripped to an oil, taken up in 75 ml. ethyl acetate, washed 1×50 ml. saturated NaHCO$_3$ and 1×50 ml. brine, dried over MgSO$_4$ and stripped to yield purified title product as a second oil, 4.22 g.; $^1$H-nmr 1.5 (s, 6H), 3.8 (s, 3H), 4.5 (s, 2H), 7.3–7.5 (m, 5H).

PREPARATION 53

Methyl 3-Benzyloxy-3-methyl-2-oxobutyl Sulfoxide

By the method of Preparation 2, the product of the preceding Preparation (4.2 g., 0.020 mol) was converted to present title product as an oil, 5.0 g.; $^1$H-nmr 1.5 (s), 2.6 (s), 3.9–4.5 (q), 4.5 (s), 7.3–7.5 (s).

PREPARATION 54

(3-Benzyloxy-3-methyl-1-methylthio-1-butanol

By the method of Preparation 3, the product of the preceding Preparation (5.0 g., 0.02 mol) was converted to present title product (4.0 g.; $^1$H-nmr (300 MHz) 1.45 (s, 3H), 1.65 (s, 3H), 1.95 (s, 3H), 4.45–4.65 (q, 2H), 7.35 (m).

PREPARATION 55

(1-Benzyloxy-1-methylthyl)glyoxal

By the method of Preparation 4, the product of the preceding Preparation (3.5 g., 0.014 mol) was converted to the hydrate of title product as an oil (2.7 g.), distilled in Kugelrohr apparatus at 125°/4 mm to produce 1.5 g. of title product; $^1$H-nmr (300 MHz) 1.6 (s, 6H), 4.5 (s, 2H), 7.4 (m, 5H), 9.6 (s, 1H).

PREPARATION 56

(1-Methylcyclohexyl)glyoxal

By the methods of Preparation 52 to 55, 1-methylcyclohexylcarboxylic acid (30.0 g., 0.211 mol) was converted to title product, 12 g.; distilled at 125° C./5mm; $^1$H-nmr (300 MHz) 9.2 (s, 1H), 1.2 (s, 3H), 1.2–1.6 (m, 10H).

PREPARATION 57

1-Adamantyl (Ethylthio)methyl Ketone

Ethyl mercaptan (5.76 ml., 4.83 g., 0.078 mol) in 250 ml. THF was cooled to −70°. n-Butyllithium (50 ml. of 1.55M in hexane, 0.078 mol) was added over 10 minutes at that temperature. The mixture was then allowed to warm to 10°, recooled to −70°, and 1-adamantyl bromomethyl ketone (20 g., 0.078 mol) in 125 ml. THF added over. The mixture was stirred 15 minutes at −70° C., stripped to one fifth volume, diluted to 600 ml. with ether, washed 2×200 ml. saturated NH$_4$Cl, 3×150 ml. H$_2$O and 1×200 ml. brine, dried over MgSO$_4$ and stripped to yield title product as an oil, 18.5 g. $^1$H-nmr (300 MHz) 1.2 (t, 3H), 1.6–2.1 (m, 15H), 2.5 (q, 2H), 3.35 (s, 2H).

PREPARATION 58

Ethyl (1-Adamantylcarbonyl)methyl Sulfoxide

The product of the preceding Preparation (18 g., 0.078 mol) was dissolved in 300 ml. CH$_2$Cl$_2$ and cooled to 0°. m-Chloroperbenzoic acid (16.2 g., 0.078 mol) as added as a slurry in 100 ml. CH$_2$Cl$_2$. After stirring 1.5 hours at 0°, the reaction mixture was extracted 1×150 ml. saturated NaHCO$_3$. The aqueous layer was back extracted with 100 ml. fresh CH$_2$Cl$_2$. The organic layers were combined, washed 3×100 ml. brine, dried over MgSO$_4$ and stripped to title product as an oil, 19.5 g.; $^1$H-nmr (300 MHz) 1.3 (t, 3H), 1.55–1.80 (br m), 2.0 (br s), 2.7 (m), 3.8 (dd).

PREPARATION 59

(1-Adamantyl)glyoxal

By the method of Preparations 54–55, the product of the preceding Preparation was converted to (1-adamantyl)glyoxal hydrate, 16.0 g., oil; $^1$H-nmr (300 MHz) showed the expected 1-adamantyl peaks, the diffuse OH peaks not being detected.

The hydrate (6.0 g.) was converted to crystalline title product (4.0 g.) by distillation in vacuo in a Kugelrohr apparatus; $^1$H-nmr (300 MHz) showed the expected 1-adamantyl and aldehyde hydrogen peaks.

PREPARATION 60

4-(2-Methyl-1,3-dioxol-2-yl)phenyl Bromide

To 4-Bromoacetophenone (50.0 g., 0.25 mol) in 500 ml. benzene was added ethylene glycol (21.7 ml., 24.2 g., 0.39 mol) followed by BF$_3$ etherate (3.69 ml., 4.26 g., 0.03 mol). The mixture was heated at reflux with a Dean-Stark trap, cooled, washed 1×350 ml. saturated NaHCO$_3$, dried and stripped to yield title product as an oil which crystallized on standing 60.2 g., recrystallized from pentane (chilled in an acetone-dry ice bath) 43.6 g.; $^1$H-nmr 1.6 (s, 3H), 3.75 (m, 2H), 4.0 (m, 2H), 7.3 (d, 2H), 7.45 (d, 2H).

PREPARATION 61

4-(Hydroxymethyl)acetophenone

The product of the preceding Preparation (25 g., 0.103 mol) in 550 ml. THF was cooled to −78°. n-Butyllithium (66.5 ml. of 1.55M in hexane, 0.103 mol) was added over 45 minutes, maintaining a temperature of −75 to −78°. Excess paraformaldehyde was heated to 175° and gaseous formaldehyde bubbled into the cold reaction mixture by nitrogen sweep. The reaction was monitored by tlc (3:1 hexane:ethyl acetate) and continued until conversion of starting material (Rf 0.59) to product (Rf 0.19) was largely complete. The reaction mixture was then quenched with acetic acid (0.103 mol) at −78°, warmed to room temperature, diluted with 500 ml. H$_2$O and 750 ml. ethyl acetate. The organic layer was separated, washed 3×600 ml. H$_2$O, dried over MgSO$_4$ and stripped to yield intermediate ethylene glycol ketal of title product, 20 g. The latter was stirred with 80 ml. 1N HCl for 2.5 hours, stripped to an oil, taken up in 300 ml. ethyl acetate, washed 3×150 ml. saturated NaHCO$_3$ and 1×150 ml. brine, dried over MgSO$_4$, restripped to an oil (8.0 g.) and chromatographed on silica gel with 1:1 hexane:ethyl acetate as eluant to yield title product as a white solid 5.46 g.; tlc Rf 0.29 (1:1 hexane:ethyl acetate).

PREPARATION 62

[4-(t-butyltrimethylsiloxymethylphenyl)]glyoxal

To a solution of the product of the preceding Preparation (4.43 g., 0.0295 mol) in 55 ml. DMF was added imidazole (4.02 g., 0.059 mol) followed by t-butyldimethylsilyl chloride (6.67 g., 0.0443 mol). After stirring 3 hours, the reaction mixture was stripped, the residue distributed between 100 ml. each of water and ethyl acetate, the layers separated, and the aqueous layer extracted 1×50 ml. fresh ethyl acetate. The organic layers were combined, washed 3×50 ml. H$_2$O and 1×50 ml. brine, dried and stripped to yield intermediate 4-(t-butyltrimethylsiloxymethyl)acetophenone as an oil, 7.66 g. The latter and SeO$_2$ (9.66 g.) were heated at 110° in 100 ml. dioxane for 6 hours, filtered over diatomaceous earth, stripped to an oil, taken up in 200 ml. CH$_2$Cl$_2$, refiltered and stripped to yield title product as an oil, 7 g., tlc Rf 0.30 (2:1 hexane:ethyl acetate).

PREPARATION 63

4-(1-Hydroxy-1-methylethyl)acetophenone

By the methods of Preparation 60, replacing excess formaldehyde with three equivalents of acetone, 4-(2-methyl-1,3-dioxol-2-yl)phenyl bromide (5.0 g., 0.021 mol) was converted to present title product, 2.5 g.; oil which crystallized on standing in vacuo; $^1$H-nmr (300 MHz) 1.55 (s, 6H), 2.5 (s, 3H), 7.5 (d, 2H), 7.85 (d, 2H).

PREPARATION 64

[4-(1-Hydroxy-1-methylethyl)phenyl]glyoxal

Product of the preceding Preparation (2.0 g., 0.011 mol) and SeO$_2$ (3.1 g., 0.028 mol) were combined in 12.5 ml. dioxane and 1.0 ml. H$_2$O and heated at 100° C. for 4 hours. The mixture was cooled, filtered over diatomaceous earth, the filtrate stripped to an oil, and the oil chromatographed on silica gel with 1:1 hexane:ethyl acetate as eluant to yield hydrate of title product as an oil, 1.25 g. The hydrate 1.2 g., was distilled in a Kugelrohr apparatus (130°/0.2 mm) to yield title product, 1.0 g.; $^1$H-nmr 1.6–1.7 (2s, 6H), 7.6–8.1 (2d, 4H), 9.6 (s, 1H).

PREPARATION 65

4-(2-Methyl-1,3-dioxol-2-yl)benzyl Chloride

Methyl 4-acetylbenzoate (20.5 g., Preparation 49) was converted to its ethylene glycol ketal [25.5 g.; $^1$H-nmr 2.65 (s, 3H), 3.8 (m, 2H), 3.9 (s, 3H), 4.1 (m, 2H), 7.55 (d, 2H), 8.0 (d, 2H)] according to the method of Preparation 60. The ketal (25.5 g., 0.115 mol) was reduced in toluene (300 ml.) with sodium bis(2-methoxyethoxy)aluminum hydride (40.6 ml. of 3.4M in toluene, 0.138 mol) to yield, after H$_2$O quench, basification with 1N NaOH, extraction into ethyl acetate and stripping, the intermediate benzyl alcohol, 21.8 g., [oil; identical with the intermediate of Preparation 61; $^1$H-nmr 1.6 (s, 3H), 2.8 (br t, 1H), 3.8 (m, 2H), 4.0 (m, 2H), 4.7 (d, 2H), 7.2–7.6 (q, 4H)]. The alcohol (21.8 g., 0.112 mol) and pyridine (9.06 ml., 8.86 g., 0.112 mol) were combined in 200 ml. CHCl$_3$. SOCl$_2$ (8.20 ml., 13.4 g., 0.112 mol) in 60 ml. CHCl$_3$ was added dropwise over 15 minutes. After stirring for 4 hours, the reaction mixture was stripped, the residue was taken up in 350 ml. ethyl acetate, and pyridine salts removed by filtration. The filtrate was washed 2×150 ml. H$_2$O, 1×150 ml. saturated NaHCO$_3$ and 1×150 ml. brine, dried and stripped to yield title product as an oil, 23.0 g.; $^1$H-nmr 1.6 (s, 3H), 3.7 (m, 2H), 4.0 (m, 2H), 4.55 (s, 2H), 7.3 (d, 2H), 7.4 (d, 2H).

PREPARATION 66

[4-(Chloromethyl)phenyl]glyoxal

According to the methods of Preparations 61 and 64, the product of the preceding Example (22.8 g.) was hydrolyzed to the acetophenone (16.5 g.) and reacted with SeO$_2$ to form the hydrate of title product, 9 g., distilled in vacuo in a Kugelrohr apparatus to yield title product as an oil, 4.0 g.

PREPARATION 67

3-(Benzyloxycarbonylamino)-3-methyl-2-butanone

3-Amino-3-methyl-2-butanone hydrochloride hydrate [J. Org. Chem. 49, 1209 (1984)] (10.6 g., 0.076 mol was dissolved in 700 ml. 1:1 THF:H$_2$O and the pH adjusted to 6.8 with dilute NaOH. Benzylchloroformate (11.93 ml., 0.084 ml.) was added dropwise, maintaining pH 6.8–7.0 by the simultaneous dropwise addition of dilute NaOH. The pH was so maintained until it stabilized. The reaction mixture was extracted 4×100 ml. CHCl$_3$. The organic extracts were combined, filtered and stripped to yield title product as an oil, 9.26.

PREPARATION 68

[1-(Benzyloxycarbonylamino)-1-methylethyl]glyoxal

The entire product of the preceding Example (9.26 g., 0.04 mol) was dissolved in 70 ml. dioxane and 8 ml. H$_2$O. SeO$_2$ (4.36 g., 0.04 mol) was added with stirring and, after 15 minutes heat at 90° for 7 hours, at which time like amount of SeO$_2$ was added and the stirred mixture heated at 90° for an additional 18 hours. The reaction mixture was cooled, filtered over sand and diatomaceous earth, and the filtrate dried over MgSO$_4$, stripped, the residue triturated with ethyl acetate. The triturate was stripped and the residue chromatographed on silica gel with 3:2 hexane:ethyl acetate as eluant to yield title product as an oil, 4.62 g.; $^1$H-nmr 1.46 (s, 6H), 5.02 (s, 2H), 5.56 (br s, 1H), 7.25 (m, 5H), 9.15 (s, 1H).

PREPARATION 69

[4-(Benzyloxycarbonylamino)phenyl]glyoxal

By the method of the preceding Preparation, using 3:17 ethyl acetate as eluant on chromatography; 4-(benzyloxycarbonylamino)acetophenone (20 g., 0.074 mol) was converted to the hydrate of title product, 18.7 g., as a solid, dehydrated by heating at 140°/0.25 torr; $^1$H-nmr 5.17 (s, 2H), 7.34 (s, 5H), 7.51 (d, 2H, J=6 Hz), 8.52 (d, 2H, J=6 Hz), 9.57 (s, 1H).

PREPARATION 70

(3-Hydroxyphenyl)glyoxal

Using 1:1 hexane:ethyl acetate as eluant, the method of Preparation 68 was employed to convert 3-hydroxyacetophenone (15.0 g., 0.11 mol) to present title product, 7.4 g.; $^1$H-nmr (DMSO-d$_6$) 7.09 (m, 2H), 7.43 (m, 3H), 9.75 (br m, 1H).

PREPARATION 71

3-(Dimethoxyacetyl)quinoline

3-Bromoquinoline (3.29 ml., 0.032 mol) was dissolved in 300 ml. THF and cooled to −78°. n-Butyllithium (13.6 ml. of 2.5M in hexane, 0.034 ml.) was added slowly and the mixture stirred 15 minutes at −75° to −78°. N-(Dimethoxyacetyl)morpholine (5.98 g., 0.032 mol) in 10 ml. THF was then added and stirring continued for 1.75 hours at the same temperature. The reaction was then quenched into 300 ml. saturated NH$_4$Cl. The aqueous layer was separated and extracted 4×100 ml. ether. The organic layers were combined, dried over MgSO$_4$O, stripped to yield title product, 7.0 g., bp 120°–123°/0.125 torr.

PREPARATION 72

(3-Quinolyl)glyoxal

Product of the preceding Preparation (3.17 g., 0.014 mol) was heated in 20 ml. 6N HCl at 45° for 3.5 hours, then cooled and extracted 3×50 ml. ether and 3×50 ml. ethyl acetate. The organic extracts were combined and stripped to yield 1.40 g. of the hydrate of title product; $^1$H-nmr 5.75 (t, 1H, J=4 Hz), 7.15 (d, 2H, J=4 Hz), 7.76 (t, 1H, J=4 Hz), 7.91 (t, 1H, J=4 Hz), 8.12 (d, 1H, J=4 Hz), 8.24 (d, 1H, J=4 Hz), 9.12 (s, 1H), 9.45 (s, 1H). The anhydrous title product was obtained by heating at 145°/0.20 torr.

PREPARATION 73

(4-Hydroxyphenyl)glyoxal

4-Hydroxyacetophenone (15 g., 0.11 mol) was dissolved in 70 ml. dioxane and 8.3 ml. H$_2$O. SeO$_2$ (12.2 g., 0.11 mol) was added and the mixture heated at 80° for 18 hours, then filtered over diatomaceous earth. The filtrate was stripped, taken up in 150 ml. H$_2$O, heated on a steam bath, decolorized with activated carbon, cooled to refrigerator temperature, and hydrate of title product recovered by filtration, 5.72 g. Anhydrous title product was obtained by Kugelrohr distillation; $^1$H-nmr 5.97 (s, 1H), 6.97 (d, 2H, J=6 Hz), 8.22 (d, 2H, J=6 Hz), 9.68 (s, 1H).

PREPARATION 74

(2-Naphthyl)glyoxal

2-Acetonaphthalene (15 g., 0.088 mol) and $SeO_2$ (9.78 g., 0.088 mol) were refluxed at 82° for 14 hours. Fresh $SeO_2$ (4.89 g., 0.044 mol) was added and reflux continued for 18 hours more. The reaction was cooled, filtered over diatomaceous earth, the filtrate reduced to an oil, chromatographed on silica gel with 3:1 hexane:ethyl acetate as eluant to yield 5.3 g. of hydrate, and distilled in a Kugelrohr apparatus to yield 3.3 g. of title product as an oil; $^1$H-nmr 7.66 (m, 2H), 8.05 (m, 4H), 8.91 (s, 1H), 9.81 (s, 1H).

We claim:

1. A compound having the formula

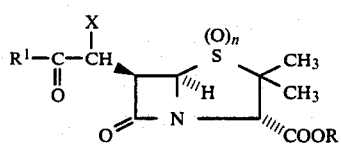

wherein n is 0, 1 or 2;

X is OH or $OCOR^2$, wherein $R^2$ is hydrogen or $(C_1-C_4)$alkyl;

R is hydrogen, a radical group forming an ester hydrolyzable under physiological conditions, or an acyloxymethyl or 1-(acyloxy)ethyl radical derived from a conventional beta-lactam antibiotic; and $R^1$ is $(C_1-C_7)$alkyl, $(C_5-C_7)$cycloalkyl, $(C_6-C_{12})$cycloalkylalkyl, $(C_6-C_{12})$alkylcycloalkyl, adamantyl, phenyl, $(C_7-C_{12})$phenylalkyl, $(C_7-C_{12})$alkylphenyl, $(C_7-C_{12})$phenoxyalkyl, naphthyl, furyl $(C_5-C_{10})$furylalkyl, benzofuranyl, benzofuranylmethyl, thienyl, $(C_5-C_{10})$thienylalkyl, benzothienyl, benzothienylmethyl, $(C_5-C_8)$-N-alkylpyrrolyl, N-phenylpyrrolyl, $(C_{11}-C_{12})$-N-(phenylalkyl)pyrrolyl, $(C_6-C_{12})$-N-alkylpyrrolylalkyl, $(C_9-C_{12})$-N-alkylindolyl, $(C_9-C_{12})$-N-alkylindolylmethyl, $(C_9-C_{12})$-N-alkylisoindolyl, $(C_9-C_{12})$-N-alkylisoindolylmethyl, indolizinyl, indolizinylmethyl, oxazolyl, $(C_4-C_9)$oxazolylalkyl, benzoxazolyl, benzoxazolylmethyl, isoxazolyl, $(C_4-C_9)$isoxazolylalkyl, benzisoxazolyl, benzisoxazolylmethyl, thiazolyl, $(C_4-C_9)$thiazolylalkyl, benzothiazolyl, benzothiazolylmethyl, isothiazolyl, $(C_4-C_9)$isothiazolylalkyl, benzothiazolyl, benzothiazolylmethyl, $(C_4-C_7)$-N-alkylpyrazolyl, $(C_5-C_{11})$-N-alkylpyrazolylalkyl, $(C_8-C_{11})$-N-alkylindazolyl, $(C_8-C_{11})$-N-alkylindazolylmethyl, $(C_4-C_7)$-N-alkylimidazolyl, $(C_5-C_{11})$-N-alkylimidazolylalkyl, $(C_8-C_{11})$-N-alkylbenzimidazolyl, $(C_8-C_{11})$-N-alkylbenzimidazolylmethyl, pyridyl, $(C_6-C_{11})$-pyridylalkyl, quinolyl, quinolylmethyl, isoquinolyl, isoquinolylmethyl, pyrazinyl, $(C_5-C_{10})$pyrazinylalkyl, quinoxalinyl, quinoxalinylmethyl, pyrimidinyl, $(C_5-C_{10})$-pyrimidinylalkyl, quinazolinyl, quinazolinylmethyl, pyridazinyl, $(C_5-C_{10})$pyridazinylalkyl, phthalazinyl, phthalazinylmethyl, cinnolinyl or cinnolinylmethyl;

or one of said groups mono- or disubstituted on aliphatic, aromatic or heterocyclic carbon with fluoro, chloro, bromo, $(C_1-C_4)$alkyl, phenyl, hydroxy, $(C_1-C_4)$alkoxy, phenoxy, benzyloxy, $(C_2-C_5)$alkoxycarbonyloxy, $(C_2-C_4)$alkenyloxy, formyloxy, $(C_2-C_5)$alkanoyloxy, $(C_2-C_5)$alkoxycarbonyl, $(C_1-C_4)$alkanesulfonamido, cyano, carbamoyl, $(C_2-C_5)$alkylcarbamoyl, di[$(C_1-C_4)$alkyl]carbamoyl, aminosulfonyl, $(C_1-C_4)$alkylaminosulfonyl or di[$(C_1-C_4)$alkyl]aminosulfonyl, or

where $R^{10}$ and $R^{11}$ are taken separately and $R^{10}$ is hydrogen, $(C_1-C_4)$alkyl, phenyl or benzyl, and $R^{11}$ is hydrogen, $(C_1-C_4)$alkyl, phenyl, benzyl, formyl, $(C_2-C_5)$alkanoyl, benzoyl, phenoxyacetyl, phenylacetyl or phenylacetyl substituted on aromtic carbon with hydroxy or amino; or $R^{10}$ and $R^{11}$ are taken together with the nitrogen to which they are attached to form a pyrrolidine, piperidine, perhydroazepine, morpholine, piperazine, N-[$(C_1-C_4)$alkyl]piperazine or N-[$(C_2-C_5)$alkanoyl]piperazine ring; where said disubstituents may be the same or different; with the provisos that no tetrahedral carbon is simultaneously bonded to a nitrogen or oxygen atom and a fluoro, chloro, bromo or second nitrogen or oxygen atom; and that no nitrogen is quaternary;

a pharmaceutically acceptable cationic salt when the compound contains a carboxylic acid group;

a pharmaceutically acceptable acid addition salt when the compound contains a basic nitrogen atom.

2. A compound of claim 1 wherein X is hydroxy and $R^1$ is alkyl, aminoalkyl, benzyloxyalkyl, cycloalkyl, adamantyl, phenyl, alkylphenyl, hydroxyalkylphenyl, chloroalkylphenyl, alkoxyphenyl, alkoxycarbonylphenyl, cyanophenyl, fluorophenyl, alkenyloxyphenyl, hydroxyphenyl, aminophenyl, dialkylaminophenyl, naphthyl, alkoxynaphthyl, furyl, thienyl, benzothienyl, benzyl, thenyl, furfuryl, phenylthiazolyl, N-alkylimidazolyl, quinolinyl, isoquinolinyl, N-(phenylalkyl)pyrrolyl, N-alkylpyrrolyl, or N-alkylindolyl.

3. A compound of claim 1 wherein n is 0.

4. A compound of claim 2 wherein n is 0.

5. A compound of claim 4 wherein $R^1$ is methyl, t-butyl, 1-benzyloxy-1-methylethyl, 1-methylcyclohexyl, 1-adamantyl, 1-amino-1-methylethyl, phenyl, 4-methylphenyl, 4-(hydroxymethyl)phenyl, 4-(1-hydroxy-1-methylethyl)phenyl, 4-(chloromethyl)phenyl, 4-methoxyphenyl, 2-methoxyphenyl, 4-propenyloxyphenyl, 4-methoxycarbonylphenyl, 4-cyanophenyl, 4-fluorophenyl, 3-hydroxyphenyl, 4-hydroxyphenyl, 4-aminophenyl 4-(dimethylamino)phenyl, 1-naphthyl, 2-ethoxy-1-naphthyl, 2-naphthyl, 2-furyl, 2-thienyl, 3-thienyl, 2-benzothienyl, benzyl, 2-thenyl, 3-methyl-2-imidazolyl, 2-phenyl-4-thiazolyl, N-methyl-2-pyrrolyl, N-benzyl-2-pyrrolyl, N-methyl-2-indolyl, N-methyl-3-indolyl, 3-quinolyl, or 1-isoquinolyl.

6. A compound of claim 1 wherein the X-substituted carbon of the sidechain is in the S-configuration:

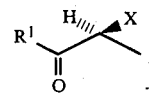

7. A compound of claim 4 wherein the X-substituted carbon of the sidechain is in the S-configuration.

8. A compound of claim 5 wherein R is hydrogen and the X-substituted carbon of the sidechain is in the S-configuration.

9. The compound of claim 8 wherein $R^1$ is phenyl.

10. The compound of claim 8 wherein $R^1$ is 4-hydroxyphenyl.

11. The compound of claim 8 wherein $R^1$ is thienyl.

12. The compound of claim 8 wherein $R^1$ is benzyl.

13. The compound of claim 8 wherein $R^1$ is thenyl.

14. A compound of claim 1 wherein n is 1 or 2, and X is hydroxy.

15. A compound of claim 14 wherein R is hydrogen and $R^1$ is phenyl or 4-methoxyphenyl.

16. A compound of claim 15 wherein the X-substituted carbon of the sidechain is in the configuration:

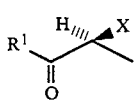

17. The compound of claim 16 wherein $R^1$ is phenyl, n is 1 and the 1-oxide is in the alpha-configuration.

18. The compound of claim 16 wherein $R^1$ is phenyl, n is 1 and the 1-oxide is in the beta-configuration.

19. A compound of claim 1 wherein R is a radical group forming an ester hydrolyzable under physiological conditions.

20. A compound of claim 4 wherein R is a radical group forming an ester hydrolyzable under physiological conditions.

21. A compound of claim 5 wherein R is a radical group hydrolyzable under physiological conditions and the X-substituted carbon of the sidechain is in the S-configuration.

22. A compound of claim 21 wherein R is:
(5-methyl-1,3-dioxol-2-on-4-yl)methyl;
1H-isobenzofuran-3-on-1-yl;
gamma-butyrolacton-4-yl;
—$CHR^3OCOR^4$; or
—$CHR^3OCOOR^5$;
wherein $R^3$ is hydrogen or methyl; $R^4$ is ($C_1$-$C_6$)alkyl, ($C_1$-$C_6$)carboxyalkyl, carboxycyclohexyl or carboxyphenyl; and $R^5$ is ($C_1$-$C_6$)alkyl.

23. A compound of claim 22 wherein R is 1-(ethoxycarbonyloxy)ethyl.

24. A compound of claim 22 wherein R is pivaloyloxymethyl.

25. The compound of claim 24 wherein $R^1$ is 2-thienyl.

26. A compound of claim 1 wherein R is an acyloxy radical derived from a conventional beta-lactam antibiotic.

27. A compound of claim 4 wherein R is an acyloxy radical derived from a conventional beta-lactam antibiotic.

28. A compound of claim 5 wherein R is an acyloxymethyl radical derived from a conventional beta-lactam antibiotic and the X-substituted carbon of the sidechain is in the S-configuration.

29. A compound of claim 28 wherein R is an acyloxy methyl radical of the formula

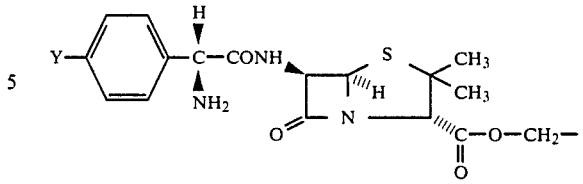

wherein Y is hydrogen, hydroxy, ($C_2$-$C_7$)alkanoyloxy, ($C_2$-$C_7$)alkoxycarbonyloxy, benzoyloxy monosubstituted with ($C_1$-$C_4$)alkyl, ($C_1$-$C_4$)alkoxy or halo.

30. A compound of claim 29 wherein Y is hydrogen.

31. A compound of claim 29 wherein Y is hydroxy.

32. The compound of claim 30 wherein $R^1$ is 2-thienyl.

33. A pharmaceutical composition for treating bacterial infections which comprises, in a weight ratio of 10:1 to 1:3, a conventional beta-lactam antibiotic and a compound of claim 1 wherein R is hydrogen or a radical group forming an ester which is hydrolyzable under physiological conditions.

34. A pharmaceutical composition for treating bacterial infections which comprises, in a weight ratio of 10:1 to 1:3, a conventional beta-lactam antibiotic and a compound of claim 4 wherein R is hydrogen or a radical group forming an ester which is hydrolyzable under physiological conditions.

35. A pharmaceutical composition for treating bacterial infections which comprises in a weight ratio of 10:1 to 1:3, a conventional beta-lactam antibiotic and a compound of claim 5 wherein R is hydrogen or a radical group forming an ester which is hydrolyzable under physiological conditions and the X-substituted carbon in the sidechain is in the S-configuration.

36. A pharmaceutical composition of claim 35 wherein the beta-lactam antibiotic is
amoxicillin,
ampicillin,
apalcillin,
azlocillin,
azthreonam,
bacampicillin,
carbenicillin,
carbenicillin indanyl,
carbenicillin phenyl,
cefaclor,
cefadroxil,
cefaloram,
cefamandole,
cefamandole nafate,
cefaparole,
cefatrizine,
cefazolin,
cefbuperazone,
cefmenoxime,
cefonicid,
cefodizime,
cefoperazone,
ceforanide,
cefotaxime,
cefotiam,
cefoxitin,
cefpimazole,
cefpiramide,
cefpirome,
cefsulodin, ceftazidime,
ceftizoxime,
ceftriaxone,
cefuroxime,
cephacetrile,
cephalexin,
cephaloglycin,
cephaloridine,
cephalothin,
cephapirin,
cephradine,
cyclacillin,
epicillin,
furazlocillin
hetacillin,
lenampicillin,
levopropylcillin,
mecillinam,
mezlocillin,
penicillin G,
penicillin V,
phenethicillin,
piperacillin,
pivampicillin,
sarmoxicillin,
sarpicillin,
suncillin,
talampicillin,
ticarcillin; or
7-[D-(2-[4-carboxy-5-imidazolecarboxamido])-2-phenylacetamido]-3-[4-sulfonatoethyl)pyridinium]-3-cephem-4-carboxylic acid;
or a pharmaceutically-acceptable salt thereof.

37. A pharmaceutical composition of claim 36 wherein the beta-lactam antibiotic is ampicillin, hetacillin, pivampicillin, bacampicillin, talampicillin or lenampicillin.

38. A pharmaceutical composition of claim 36 wherein the beta-lactam antibiotic is amoxicillin, sarmoxicillin or sarpicillin.

39. A pharmaceutical composition of claim 36 wherein the beta-lactam antibiotic is cefoperazone.

40. A method of treating a bacterial infection in a mammal which comprises administering to said mammal an antibacterially effective amount of a pharmaceutical composition of claim 33.

41. A method of treating a bacterial infection in a mammal which comprises administering to said mammal an antibacterially effective amount of a pharmaceutical composition of claim 34.

42. A method of treating a bacterial infection in a mammal which comprises administering to said mammal an antibacterially effective amount of a pharmaceutical composition of claim 35.

43. A method of treating a bacterial infection in a mammal which comprises administering to said mammal an antibacterially effective amount of a pharmaceutical composition of claim 36.

44. A method of treating a bacterial infection in a mammal which comprises administering to said mammal an antibacterial effective amount of a pharmaceutical composition of claim 37.

45. A method of treating a bacterial infection in a mammal which comprises administering to said mammal an antibacterially effective amount of a pharmaceutical composition of claim 38.

46. A method of treating a bacterial infection in a mammal which comprises administering to said mammal an antibacterially effective amount of a pharmaceutical composition of claim 39.

47. A pharmaceutical composition comprising an antibacterial amount of a compound of claim 1.

48. A pharmaceutical composition comprising an antibacterial amount of a compound of claim 4.

49. A pharmaceutical composition comprising an antibacterial amount of a compound of claim 8.

50. A pharmaceutical composition comprising an antibacterial amount of a compound of claim 22.

51. A pharmaceutical composition comprising an antibacterial amount of a compound of claim 29.

52. A method of treating a bacterial infection in a mammal which comprises administering to said mammal an antibacterial amount of a compound of claim 1.

53. A method of treating a bacterial infection in a mammal which comprises administering to said mammal an antibacterial amount of a compound of claim 4.

54. A method of treating a bacterial infection in a mammal which comprises administering to said mammal an antibacterial amount of a compound of claim 8.

55. A method of treating a bacterial infection in a mammal which comprises administering to said mammal an antibacterial amount of a compound of claim 22.

56. A method of treating a bacterial infection in a mammal which comprises administering to said mammal an antibacterial amount of a compound of claim 29.

* * * * *